United States Patent
Link et al.

(10) Patent No.: US 10,633,652 B2
(45) Date of Patent: *Apr. 28, 2020

(54) MICROFLUIDIC DEVICES AND METHODS OF USE IN THE FORMATION AND CONTROL OF NANOREACTORS

(71) Applicant: Bio-Rad Laboratories, Inc., Hercules, CA (US)

(72) Inventors: Darren Roy Link, Lexington, MA (US); Laurent Boitard, Guilford, CT (US); Jeffrey Branciforte, Cromwell, CT (US); Yves Charles, Waterbury, CT (US); Gilbert Feke, West Simsbury, CT (US); John Q. Lu, Guilford, CT (US); David Marran, Durham, CT (US); Ahmadali Tabatabai, Branford, CT (US); Michael Weiner, Guilford, CT (US); Wolfgang Hinz, Guilford, CT (US); Jonathan M. Rothberg, Guilford, CT (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 15/694,108

(22) Filed: Sep. 1, 2017

(65) Prior Publication Data

US 2018/0080020 A1 Mar. 22, 2018

Related U.S. Application Data

(60) Continuation of application No. 15/331,452, filed on Oct. 21, 2016, now Pat. No. 9,752,141, which is a
(Continued)

(51) Int. Cl.
*C12N 15/10* (2006.01)
*B01F 13/00* (2006.01)
(Continued)

(52) U.S. Cl.
CPC ...... *C12N 15/1075* (2013.01); *B01F 13/0071* (2013.01); *B01F 13/0076* (2013.01); *B01J 19/0046* (2013.01); *B01L 3/502784* (2013.01); *B82Y 5/00* (2013.01); *B82Y 30/00* (2013.01); *C07K 1/047* (2013.01); *C12Q 1/686* (2013.01); *C12Q 1/6874* (2013.01); *C12Q 1/6876* (2013.01); *C40B 30/04* (2013.01); *C40B 40/04* (2013.01); *C40B 50/08* (2013.01); *C40B 60/08* (2013.01); *C40B 60/12* (2013.01); *C40B 70/00* (2013.01); *G01N 33/536* (2013.01); *G01N 33/543* (2013.01); *G01N 33/6845* (2013.01); *G01N 33/6854* (2013.01); *B01F 3/0807* (2013.01); *B01J 2219/005* (2013.01); *B01J 2219/0072* (2013.01); *B01J 2219/00286* (2013.01); *B01J 2219/00459* (2013.01); *B01J 2219/00466* (2013.01); *B01J 2219/00468* (2013.01); *B01J 2219/00479* (2013.01); *B01J 2219/00576* (2013.01); *B01J 2219/00599* (2013.01); *B01J 2219/00702* (2013.01); *B01J 2219/00743* (2013.01); *B01L 3/5027* (2013.01); *B01L 3/50273* (2013.01); *B01L 3/502715* (2013.01); *B01L 3/502746* (2013.01); *B01L 3/502761* (2013.01); *B01L 3/502792* (2013.01); *B01L 3/565* (2013.01); *B01L 7/52* (2013.01); *B01L 2200/027* (2013.01); *B01L 2200/0621* (2013.01); *B01L 2200/0647* (2013.01); *B01L 2200/0652* (2013.01); *B01L 2200/0673* (2013.01); *B01L 2300/0816* (2013.01); *B01L 2300/0864* (2013.01);
(Continued)

(58) Field of Classification Search
None
See application file for complete search history.

(56) References Cited

U.S. PATENT DOCUMENTS 9,752,141 B2 * 9/2017 Link .................. C12N 15/1075
2004/0185484 A1 * 9/2004 Costa ................ B01L 3/502707
506/14
2005/0227264 A1 * 10/2005 Nobile .................. B01F 3/0807
435/6.16

FOREIGN PATENT DOCUMENTS

AU 4032078 A 4/1980
AU 6415380 A 5/1981
(Continued)

OTHER PUBLICATIONS

Margulies et al. (Nature 4377057 (2005): 376-380; published online Jul. 31, 2005) (Year: 2005).*
(Continued)

*Primary Examiner* — Tracy Vivlemore
*Assistant Examiner* — Sahana S Kaup
(74) *Attorney, Agent, or Firm* — Brown Rudnick LLP; Thomas C. Meyers

(57) ABSTRACT

The present invention provides novel microfluidic devices and methods that are useful for performing high-throughput screening assays and combinatorial chemistry. The invention provides for aqueous based emulsions containing uniquely labeled cells, enzymes, nucleic acids, etc., wherein the emulsions further comprise primers, labels, probes, and other reactants. An oil based carrier-fluid envelopes the emulsion library on a microfluidic device, such that a continuous channel provides for flow of the immiscible fluids, to accomplish pooling, coalescing, mixing, sorting, detection, etc., of the emulsion library.

18 Claims, 17 Drawing Sheets

Specification includes a Sequence Listing.

Related U.S. Application Data division of application No. 14/248,991, filed on Apr. 9, 2014, now Pat. No. 9,534,216, which is a continuation of application No. 13/759,660, filed on Feb. 5, 2013, now Pat. No. 9,328,344, which is a continuation of application No. 12/087,713, filed as application No. PCT/US2006/021280 on Jun. 1, 2006, now abandoned.

(60) Provisional application No. 60/771,286, filed on Feb. 7, 2006, provisional application No. 60/763,524, filed on Jan. 30, 2006.

(51) Int. Cl.

| | | |
|---|---|---|
| *B01J 19/00* | (2006.01) | |
| *B01L 3/00* | (2006.01) | |
| *B82Y 5/00* | (2011.01) | |
| *B82Y 30/00* | (2011.01) | |
| *C07K 1/04* | (2006.01) | |
| *C40B 30/04* | (2006.01) | |
| *C40B 40/04* | (2006.01) | |
| *C40B 50/08* | (2006.01) | |
| *C40B 60/08* | (2006.01) | |
| *C40B 60/12* | (2006.01) | |
| *C40B 70/00* | (2006.01) | |
| *G01N 33/536* | (2006.01) | |
| *G01N 33/68* | (2006.01) | |
| *C12Q 1/6874* | (2018.01) | |
| *G01N 33/543* | (2006.01) | |
| *C12Q 1/6876* | (2018.01) | |
| *C12Q 1/686* | (2018.01) | |
| *B01F 3/08* | (2006.01) | |
| *G01N 33/542* | (2006.01) | |
| *G01N 21/64* | (2006.01) | |
| *C12Q 1/6816* | (2018.01) | |
| *C12Q 1/6804* | (2018.01) | |
| *C12Q 1/6834* | (2018.01) | |
| *C12Q 1/6825* | (2018.01) | |
| *B01L 7/00* | (2006.01) | |
| *C12Q 1/6869* | (2018.01) | |

(52) U.S. Cl.
CPC ........... *B01L 2300/0867* (2013.01); *B01L 2300/0896* (2013.01); *B01L 2400/0415* (2013.01); *B01L 2400/0424* (2013.01); *B01L 2400/0487* (2013.01); *B01L 2400/084* (2013.01); *C12Q 1/6804* (2013.01); *C12Q 1/6816* (2013.01); *C12Q 1/6825* (2013.01); *C12Q 1/6834* (2013.01); *C12Q 1/6869* (2013.01); *C12Q 2525/161* (2013.01); *C12Q 2561/119* (2013.01); *C12Q 2563/103* (2013.01); *C12Q 2563/107* (2013.01); *C12Q 2563/159* (2013.01); *C12Q 2565/537* (2013.01); *C12Q 2565/629* (2013.01); *C12Q 2600/16* (2013.01); *G01N 21/6428* (2013.01); *G01N 21/6445* (2013.01); *G01N 21/6458* (2013.01); *G01N 33/542* (2013.01); *G01N 2500/10* (2013.01)

(56) References Cited

FOREIGN PATENT DOCUMENTS

| | | | |
|---|---|---|---|
| AU | 1045983 | A | 6/1984 |
| AU | 4222393 | A | 11/1993 |
| AU | 4222593 | A | 11/1993 |
| AU | 4222693 | A | 11/1993 |
| AU | 4222793 | A | 11/1993 |
| AU | 4223593 | A | 11/1993 |
| AU | 677781 | B2 | 5/1997 |
| AU | 3499097 | A | 1/1998 |
| AU | 4955799 | A | 12/1999 |
| AU | 3961100 | A | 10/2000 |
| AU | 4910300 | A | 11/2000 |
| AU | 2004225691 | B2 | 6/2010 |
| CA | 2258481 | A1 | 1/1998 |
| CA | 2520548 | A1 | 10/2004 |
| CH | 563807 | A5 | 7/1975 |
| EP | 0637996 | A1 | 2/1995 |
| EP | 0637997 | A1 | 2/1995 |
| EP | 04782399.2 | | 5/2006 |
| EP | 2017910 | A1 | 1/2009 |
| EP | 13165665.4 | | 11/2013 |
| EP | 13165667.0 | | 11/2013 |
| JP | 2006-211984 | A | 8/2006 |
| WO | 97/38318 | A1 | 10/1997 |
| WO | 02/22869 | | 3/2002 |
| WO | 02/31203 | | 4/2002 |
| WO | 02/47665 | | 6/2002 |
| WO | WO-2005003375 | A2 * | 1/2005 ........ B01L 3/502707 |
| WO | 2005/010145 | A2 | 2/2005 |
| WO | 2007/114794 | A1 | 10/2007 |

OTHER PUBLICATIONS

Margulies 2005 Supplementary methods (Year: 2005).*
Ashutosh Shastry et al, Directing Droplets Using Microstructured Surfaces.
Auroux, Pierre-Alain et al., Micro Total Analysis Systems. 2. Analytical Standard Operations and Applications, Analytical Chemistry, vol. 74, No. 12, 2002, pp. 2637-2652.
Bernath et al, In Vitro Compartmentalization by Double Emulsions: Sorting and Gene Enrichment by Fluorescence Activated Cell Sorting, Anal. Biochem 325:151-157 (2004).
Dankwardt et al. Combinatorial synthesis of small-molecule libraries using 3-amino-5 hydroxybenzoic acid, 1995, vol. 1, pp. 113-120.
Japanese Office Action for Application No. JP 2009-231040 dated Jul. 1, 2014.
Kiss et al. Anal Chem. 2008, vol. 80 p. 8975-8981.
Margulies Supplementary methods (Year: 2005).
Strommenger et al. (Journal of Clinical Microbiology 41.9 (2003): 4089-4094) (Year: 2003).
Japanese Office Action for Application No. JP 2017-222501 dated Jul. 30, 2019 (5 pages).

* cited by examiner

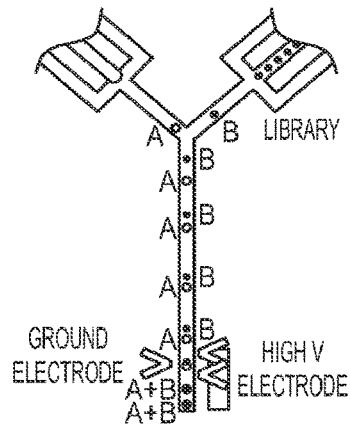 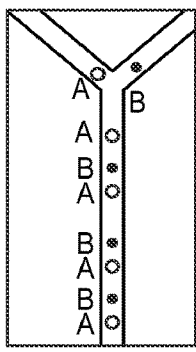 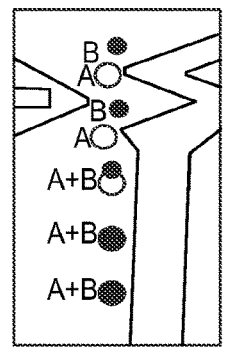 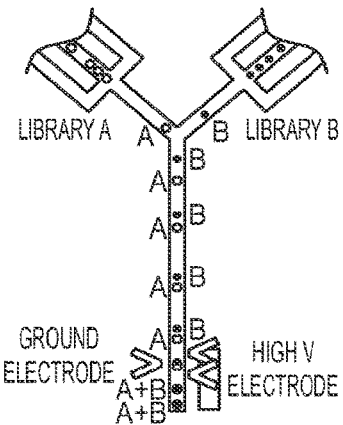
FIG. 16A  FIG. 16B  FIG. 16C  FIG. 16D
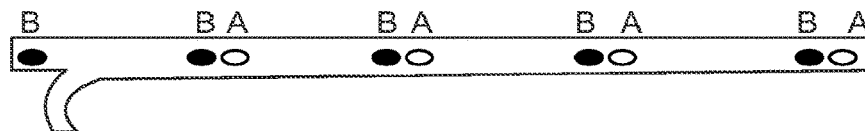
FIG. 16E
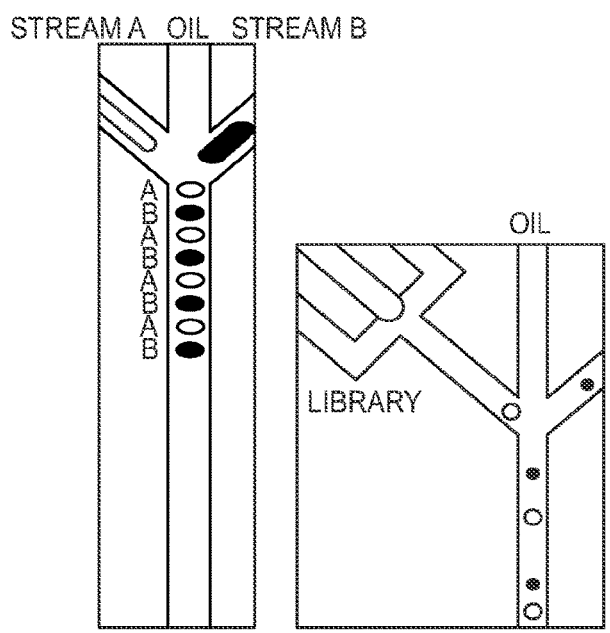 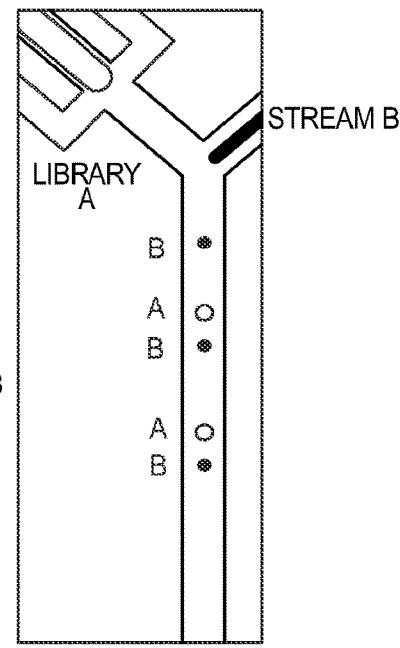
FIG. 17A  FIG. 17B  FIG. 17C

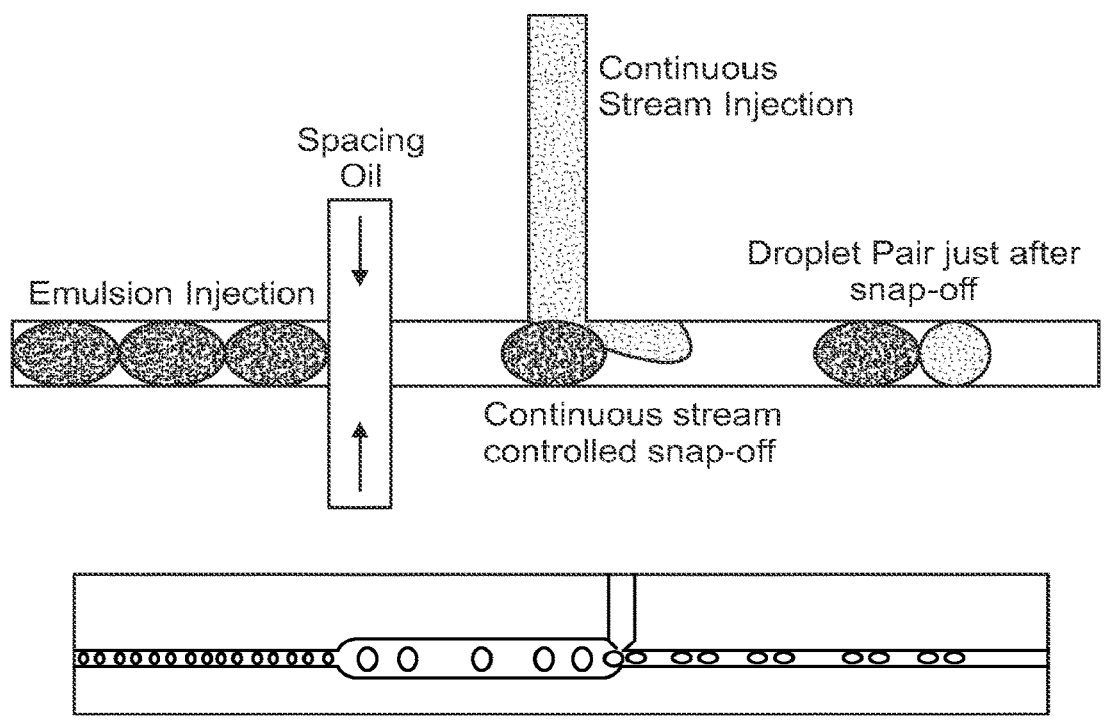
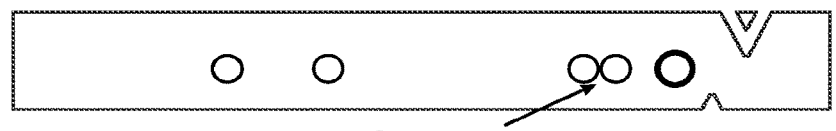
FIG. 17D
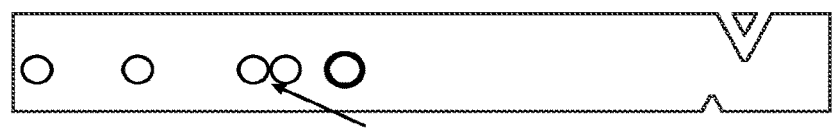
FIG. 18A
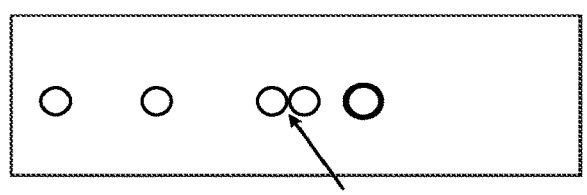
FIG. 18B
FIG. 18C
FIG. 18D

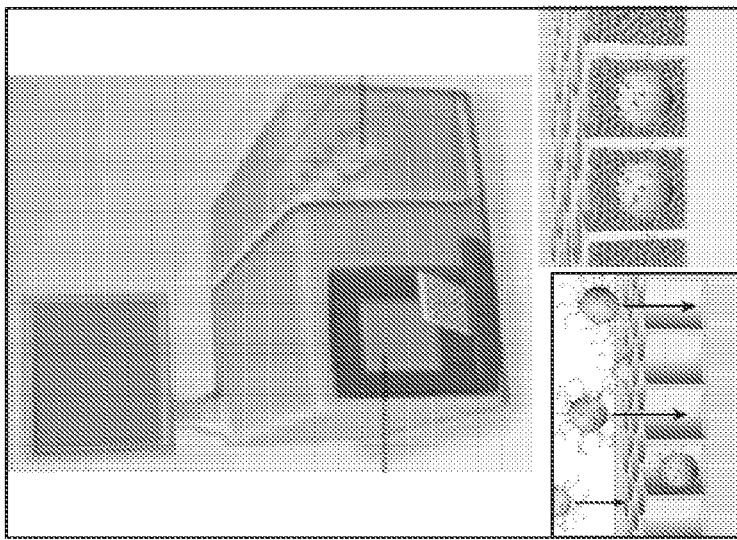
FIG. 19C
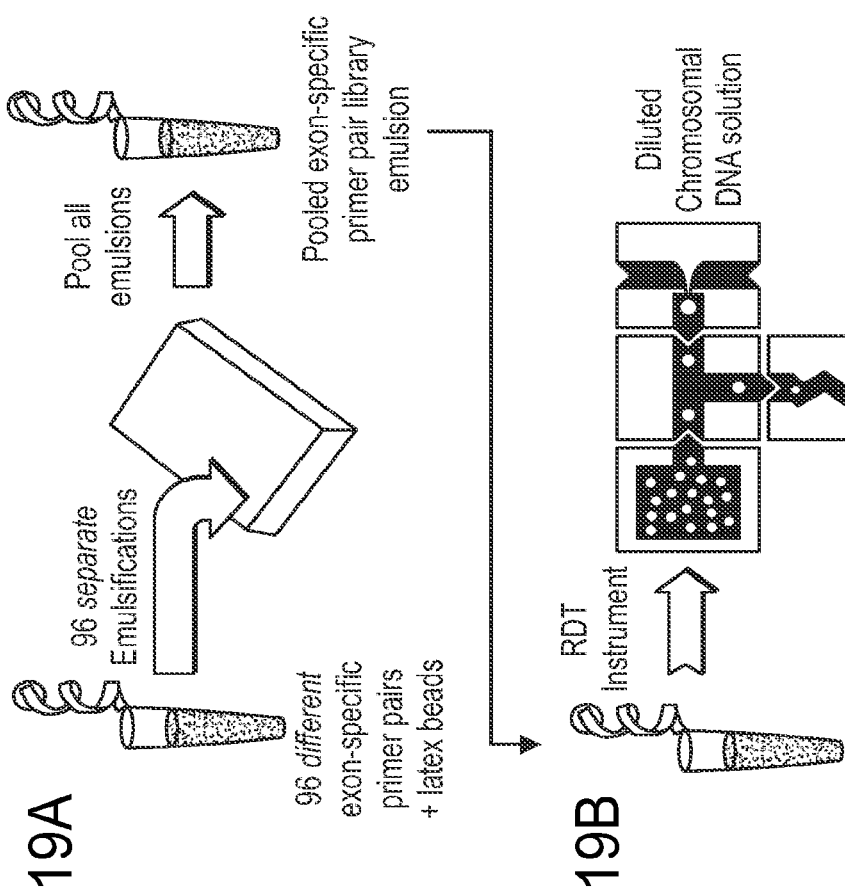
FIG. 19A
FIG. 19B

SEQUENCE LISTING

<160> NUMBER OF SEQ ID NOS: 3

<210> SEQ ID NO 1
<211> LENGTH: 63
<212> TYPE: DNA
<213> ORGANISM: Artificial Sequence
<220> FEATURE:
<223> OTHER INFORMATION: Synthetic sequence

<400> SEQUENCE: 1
atccgcccca gcagctgcca ggcacagccc ctaaactcct gatttatgct gcatccattt      60

```
tgc                                                             63

<210> SEQ ID NO 2
<211> LENGTH: 33
<212> TYPE: DNA
<213> ORGANISM: Artificial Sequence
<220> FEATURE:
<223> OTHER INFORMATION: Synthetic sequence

<400> SEQUENCE: 2
gcaaaatgga tgcagcataa atcaggagtt tag                            33

<210> SEQ ID NO 3
<211> LENGTH: 33
<212> TYPE: DNA
<213> ORGANISM: Artificial Sequence
<220> FEATURE:
<223> OTHER INFORMATION: Synthetic sequence

<400> SEQUENCE: 3
ctaaactcct gatttatgct gcatccattt tgc                            33
```

MICROFLUIDIC DEVICES AND METHODS OF USE IN THE FORMATION AND CONTROL OF NANOREACTORS

RELATED APPLICATIONS

The present application is a continuation of U.S. patent application Ser. No. 15/331,452, filed Oct. 21, 2016, which is a continuation of U.S. patent application Ser. No. 14/248,991, filed Apr. 9, 2014, which is a continuation of U.S. patent application Ser. No. 13/759,660 filed Feb. 5, 2013, which is a continuation of U.S. patent application Ser. No. 12/087,713, filed Jul. 11, 2008, which is a 35 U.S.C. 371 National Phase Application of PCT/US2006/021280, filed Jun. 1, 2006, which is a Continuation-in-Part of PCT/US2006/000931, filed on Jan. 11, 2006. PCT/US2006/021280 also claims priority to, and the benefit of, U.S. Ser. No. 60/763,524 filed Jan. 30, 2006 and 60/771,286, filed Feb. 7, 2006. Each of these applications is incorporated by reference in their entirety.

SEQUENCE LISTING

This application contains a sequence listing which has been submitted in ASCII format via EFS-Web and is hereby incorporated by reference in its entirety. The ASCII-formatted sequence listing, created on Sep. 1, 2017, is named RDT-518-US07-Sequence-Listing, and is 4,096 bytes in size.

FIELD OF INVENTION

The present invention generally relates to systems and methods for the formation and/or control of fluidic species, and articles produced by such systems and methods. More particularly, the present invention relates to the development of high throughput microfluidic devices for precision fluid handling and use of such systems in various biological, chemical, or diagnostic assays.

BACKGROUND

High throughput molecular screening (HTS) is the automated, rapid testing of thousands of distinct small molecules or probes in cellular models of biological mechanisms or disease, or in biochemical or pharmacological assays. Active compounds identified through HTS can provide powerful research tools to elucidate biological processes through chemical genetic approaches, or can form the basis of therapeutics or imaging agent development programs. HTS has experienced revolutionary changes in technology since the advent of molecular biology and combinatorial chemistry, and the incorporation of modern information management systems. Current HTS instrumentation allows screening of hundreds of thousands of compounds in a single day at a rate orders of magnitude greater than was possible a decade ago. However, there are still bottlenecks which currently limit HTS capacity, such as (a) compound collection maintenance, tracking, and disbursement, and (b) rapidity, accuracy, and content of assay instrumentation.

The manipulation of fluids to form fluid streams of desired configuration, discontinuous fluid streams, droplets, particles, dispersions, etc., for purposes of fluid delivery, product manufacture, analysis, and the like, is a relatively well-studied art. For example, highly monodisperse gas bubbles, less than 100 microns in diameter, have been produced using a technique referred to as capillary flow focusing. In this technique, gas is forced out of a capillary tube into a bath of liquid, where the tube is positioned above a small orifice, and the contraction flow of the external liquid through this orifice focuses the gas into a thin jet which subsequently breaks into equal-sized bubbles via a capillary instability. A similar arrangement can be used to produce liquid droplets in air.

Microfluidic systems have been described in a variety of contexts, typically in the context of miniaturized laboratory (e.g., clinical) analysis. Other uses have been described as well. For example, International Patent Application Publication No. WO 01/89788 describes multi-level microfluidic systems that can be used to provide patterns of materials, such as biological materials and cells, on surfaces. Other publications describe microfluidic systems including valves, switches, and other components.

Precision manipulation of streams of fluids with microfluidic devices is revolutionizing many fluid-based technologies. Networks of small channels are a flexible platform for the precision manipulation of small amounts of fluids. The utility of such microfluidic devices depends critically on enabling technologies such as the microfluidic peristaltic pump, electrokinetic pumping, dielectrophoretic pump or electrowetting driven flow. The assembly of such modules into complete systems provides a convenient and robust way to construct microfluidic devices. However, virtually all microfluidic devices are based on flows of steams of fluids; this sets a limit on the smallest volume of reagent that can effectively be used because of the contaminating effects of diffusion and surface adsorption. As the dimensions of small volumes shrink, diffusion becomes the dominant mechanism for mixing leading to dispersion of reactants; moreover, surface adsorption of reactants, while small, can be highly detrimental when the concentrations are low and volumes are small. As a result, current microfluidic technologies cannot be reliably used for applications involving minute quantities of reagent; for example, bioassays on single cells or library searches involving single beads are not easily performed. An alternate approach that overcomes these limitations is the use of aqueous droplets in an immiscible carrier fluid; these provide a well defined, encapsulated microenvironment that eliminates cross contamination or changes in concentration due to diffusion or surface interactions. Droplets provide the ideal microcapsule that can isolate reactive materials, cells, or small particles for further manipulation and study. However, essentially all enabling technology for microfluidic systems developed thus far has focused on single phase fluid flow and there are few equivalent active means to manipulate droplets requiring the development of droplet handling technology. While significant advances have been made in dynamics at the macro- or microfluidic scale, improved techniques and the results of these techniques are still needed. For example, as the scale of these reactors shrinks, contamination effects due to surface adsorption and diffusion limit the smallest quantities that can be used. Confinement of reagents in droplets in an immiscible carrier fluid overcomes these limitations, but demands new fluid-handling technology.

Furthermore, the underlying physics of the influence of electric fields on fluids is well known. The attractive and repulsive forces produced by an electric field on positive or negative charges give rise to the forces on charged fluid elements, the polarization of non-polar molecules, and the torque on polar molecules which aligns them with the field. In a non-uniform field, because the force on the positively charged portion of the distribution is different than the force on the negatively charged portion, polar molecules will also experience a net force toward the region of higher field intensity. In the continuum limit, the result is a pondermotive force in the fluid. In the limit of high droplet surface tension, it is useful to describe the net pondermotive force on a droplet as if it were a rigid sphere:

$$F = qE + 2\pi R(\varepsilon_m) r^3 R(K) \nabla E^2$$

where the first term is the electrophoretic force on the droplet (q is the net droplet charge and E is the electric field), and the second term is the dielectrophoretic force (r is the radius of the sphere, R(K) is the real part of the Clausius-Mossotti factor $$K = (\varepsilon^*_p - \varepsilon^*_m)/(\varepsilon^*_p + 2\varepsilon^*_m)$$

and $\varepsilon^*_p$ and $\varepsilon^*_m$ are the complex permittivities of the droplet and carrier fluid).

Although utility of electrophoretic control of droplets is great, it does have significant limitations. First, the charging of droplets is only effectively accomplished at the nozzle. Second, the discharge path required to eliminate screening effects also discharges the droplets. Third, finite conductivity of the carrier fluid, however small, will eventually discharge the droplets. Therefore, once the droplet is formed, there is essentially only one opportunity to perform any pondermotive function which relies on the droplet's charge density (such as coalescing oppositely charged droplets through their mutual Coulombic attraction, or electrophoretically sorting a droplet), and that function can only be performed as long as sufficient charge has not leaked off of the droplet.

Thus, it would be desirable to develop an electrically addressable emulsification system that combines compartmentalization and electrical manipulation, which allows for multi-step chemical processing, including analysis and sorting, to be initiated in confinement with exquisite timing and metering precision, for use in a variety of chemical, biological, and screening assays, in which the cost and time to perform such assays would be drastically reduced. It would also be desirable to develop a device using dielectrophoretic force (which does not rely on charge density) to manipulate droplets so that more than one electrical pondermotive function can be carried out following a significantly long delay from droplet formation.

SUMMARY OF THE INVENTION

The present invention provides devices having individual fluid handling modules that can be combined into fluid processing systems so as to perform multi-step processing of isolated components, which is essential for searching through molecular libraries for rare interactions with cells, nucleic acids, enzymes, coded microbeads, and other biomaterials. Using principles based on the electrostatic and dieletrophoretic manipulation of charged and neutral droplets 20 to 100 microns in diameter, the microfluidic devices as described herein can inexpensively encapsulate reagents, combine same, analyze, and sort in the range of 1×10 9 droplets per day. The present invention provides a microfluidic device that includes a microfabricated substrate. The substrate can include a plurality of electrically addressable channel bearing microfluidic modules integrally arranged with each other so as to be in fluid communication. The microfabricated substrate can have, for example, (i) one or more inlet modules that have at least one inlet channel adapted to carry a dispersed phase fluid, (ii) at least one main channel adapted to carry a continuous phase fluid, wherein the inlet channel is in fluid communication with the main channel such that the dispersed phase fluid is immiscible with the continuous phase fluid and forms a plurality of droplets in the continuous phase fluid, and (iii) a coalescence module downstream from and in fluid communication with the inlet modules via the main channel, wherein two or more droplets passing there through are coalesced to form a nanoreactor. The microfluidic device of the present invention can further include a sorting module, mixing module, delay module, UV-release module, detection module, collection module, waste module and/or acoustic actuator, and or combinations thereof, in any order. These modules are in fluid communication with the main channel. The flow of the dispersed phase and continuous phase can be pressure driven, for example.

The present invention also provides methods of creating a nanoreactor. The method includes, for example, a) providing a microfabricated substrate having a plurality of electrically addressable channel bearing microfluidic modules integrally arranged on the substrate so as to be in fluid communication with each other, thereby forming at least one main channel adapted to carry at least one continuous phase fluid; b) flowing a first dispersed phase fluid through a first inlet channel into the main channel such that one or more droplets is formed in the continuous phase fluid flowing therein; c) flowing a second dispersed phase fluid through a second inlet channel into the main channel such that one or more droplets is formed in the continuous phase fluid flowing therein; and d) coalescing at least one droplet formed in step (b) with at least one droplet formed in step (c) as the droplets pass through a coalescence module of the microfabricated substrate, thereby producing a nanoreactor. The coalescing step can be achieved by an electric field or passively. The first and second dispersed phase fluids can include a biological or chemical material, which can include, for example, tissues, cells, particles, proteins, antibodies, amino acids, nucleotides, small molecules, and pharmaceuticals. The nanoreactor can further be incubated within a delay module, and then interrogated for a predetermined characteristic within a detection module.

The present invention also includes methods of synthesizing a compound from two or more reactive substructures. In a particular aspect the method includes a) labeling the reactive substructures with a label unique to the substructure; b) emulsifying aqueous solutions of the labeled reactive substructures on a microfluidic device to form droplets; and c) randomly combining the droplets on the microfluidic device to form a compound. The one embodiment, the method further includes d) screening the compound formed in step (c) based on a desirable chemical or biological property exhibited by the compound; and e) identifying the structure of the compound by decoding the label. In another embodiment, steps (a) and (b) are alternatively performed by introducing a preformed labeled emulsion.

In another aspect, the present invention provides methods for identifying a single compound from a library on a microfluidic device. The method can include a) labeling a library of compounds by emulsifying aqueous solutions of the compounds and aqueous solutions of unique liquid labels, whereby each compound is labeled with a unique liquid label; b) pooling the labeled emulsions resulting from step (a); c) coalescing the labeled emulsions with emulsions containing a specific cell or enzyme, thereby forming a nanoreactor; d) screening the nanoreactors for a desirable reaction between the contents of the nanoreactor; and e) decoding the liquid label, thereby identifying a single compound from a library of compounds. In various embodiments of the method, the contents of the nanoreactor can be incubated prior to screening. The screening step can be performed by fluorescent polarization, for example. The liquid label can be a quantum dot (q-dot) or a dye.

In yet another aspect, the present invention includes methods for controlling the quality of a library of emulsified compounds. The method can include, for example, a) providing a library of emulsified compounds; b) emulsifying a q-dot encoded aqueous buffer in an inert fluorocarbon medium, thereby forming droplets; c) incubating the q-dot encoded droplet with the library of emulsified compounds; d) sorting the q-dot encoded droplet away from the library; e) analyzing the q-dot encoded droplet for the presence of any of the compounds emulsified in the library; and f) eliminating the compounds identified in step (e) from the library of emulsified compounds, wherein one or more of steps (a)-(f) are performed on a microfluidic device. In one embodiment, the analyzing step is performed by mass spectroscopy.

In still a further aspect, the present invention provides methods for sorting cells. The method can include a) fusing an affinity-reagent to an enzyme; b) mixing the fusion product of step (a) with a cell population; c) isolating cells attached to the fusion product; d) emulsifying the cells of step (c) in an inert fluorocarbon medium; e) coalescing the cell emulsion of step (d) with an emulsion comprising a substrate corresponding to the enzyme of step (a), thereby forming a nanoreactor; and f) screening the nanoreactor for a desirable reaction between the contents of the nanoreactor, wherein one or more steps of (a)-(f) are performed on a microfluidic device. In one embodiment, the affinity-reagent can be an antibody that is specific for a cell-surface cancer marker. The enzyme can include alk/phos, β-galactosidase, or horseradish peroxidase. The affinity-reagent can be fused to multiple enzymes, and multiple substrates can be emulsified and coalesced with the cell emulsions.

Another aspect of the present invention provides methods for sequencing individual exons from individual chromosomes. The method can include, for example, a) emulsifying specific primer-pairs to an exon with beads that can bind to said primer-pairs; b) pooling the emulsions of step (a) to create a library emulsion; c) providing a separate chromosomal DNA emulsion; d) coalescing the library emulsion of step (b) with the chromosomal emulsion of step (c), thereby forming a nanoreactor; e) amplifying the DNA in the nanoreactor; f) isolating the beads; g) screening for beads containing DNA; and h) sequencing the beads containing DNA, wherein one or more steps of (a)-(h) are performed on a microfluidic device.

BRIEF DESCRIPTION OF DRAWINGS

Non-limiting embodiments of the present invention will be described by way of example with reference to the accompanying drawings, which are schematic and are not intended to be drawn to scale. In the drawings, each identical or nearly identical component illustrated is typically represented by a single numeral. For the purposes of clarity, not every component is labeled in every drawing, nor is every component of each embodiment of the invention shown where illustration is not necessary to allow those of ordinary skill in the art to understand the invention. In the drawings:

FIGS. 16A-E show schematics showing droplets made on-chip (FIG. 16A) being interdigitated with library droplets (FIG. 16B). The droplets are of different size and the smaller droplets B move at a higher velocity than droplets A until they catch up after which they move together. An electric field causes the droplets to coalesce, FIG. 16C. Droplets A and B may both come from libraries (made off-chip) shown in FIG. 16D, or be made on-chip.

FIGS. 17A-D show alternate ways to achieve interdigitation of droplets of different type.

FIG. 18A-D highlight observed passive coalescence of coupled droplet pairs—(A) Tee 0.25 mM FC-1% E5-5% PVP 70-FF1% E5~5% PVP-0.1 mM FC-PBS 70-11172005-nozzles-3.cin; (B) Tee 0.25 mM FC-1% E5-5% PVP 90-FF1% E5-5% PVP-0.1 mM FC-PBS 70-11172005-nozzles-5.cin; (C) Tee 0.25 mM FC-1% E5-5% PVP 90-FF1% E5-5% PVP-0.1 mM FC-PBS 70-11172005-nozzles-prior to coalesce-8.cin; (D) 1% E5-5% PVP-0.25 mM FC-50-1% E5-5% PVP-0.1 mM FC-PBS 50-11172005-overview-1.cin.

FIGS. 19A-C show a schematic diagram of the assembly of modules used for sequencing exons of individual chromosomes. (FIG. 19A) Individual specific primer-pairs to different exons along with a primer-bound bead are each separately emulsified and then pooled to create a library emulsion (a set of 96 exon primer pairs are shown for illustrative purposes); (FIG. 19B) Individual modules are strung together in a sequence of droplet operations. A chromosomal DNA solution is diluted such that a 30 micron drop contains, on average, slightly less than a half-genome's concentration of DNA. Droplets from the pooled emulsion library set of exon-specific primers are combined with droplets containing the diluted solution of chromosomal DNA and used in a bead-based DNA amplification reaction (i.e., PCR); (FIG. 19C) The DNA-containing beads will be randomly placed into a picotiter plate and sequenced using a 454 Corp.'s Life Sciences DNA sequencing instrument.

(FIG. 20A) Genomic DNA is isolated, fragmented, ligated to adapters and separated into single strands (top left). Fragments are bound to beads under conditions that favor one fragment per bead, the beads are captured in the droplets of a PCR-reaction-mixture-in-oil emulsion and PCR amplification occurs within each droplet, resulting in beads each carrying ten million copies of a unique DNA template (top, second from the left). The emulsion is broken, the DNA strands are denatured, and beads carrying single-stranded DNA clones are deposited into wells of a fiber-optic slide (bottom left). Smaller beads carrying immobilized enzymes required for pyrophosphate sequencing are deposited into each well (bottom, second from the left); (FIG. 20B) Microscope photograph of emulsion showing droplets containing a bead and empty droplets. The thin arrow points to a 28-mm bead; the thick arrow points to an approximately 100-mm droplet; (FIG. 20C) Scanning electron micrograph of a portion of a fiber-optic slide, showing fiber-optic cladding and wells before bead deposition; (FIG. 20D) The sequencing instrument consists of the following major subsystems: a fluidic assembly; a flow chamber that includes the well-containing fiber-optic slide; a CCD camera-based imaging assembly; and a computer that provides the necessary user interface and instrument control.

DETAILED DESCRIPTION

Figure 1:
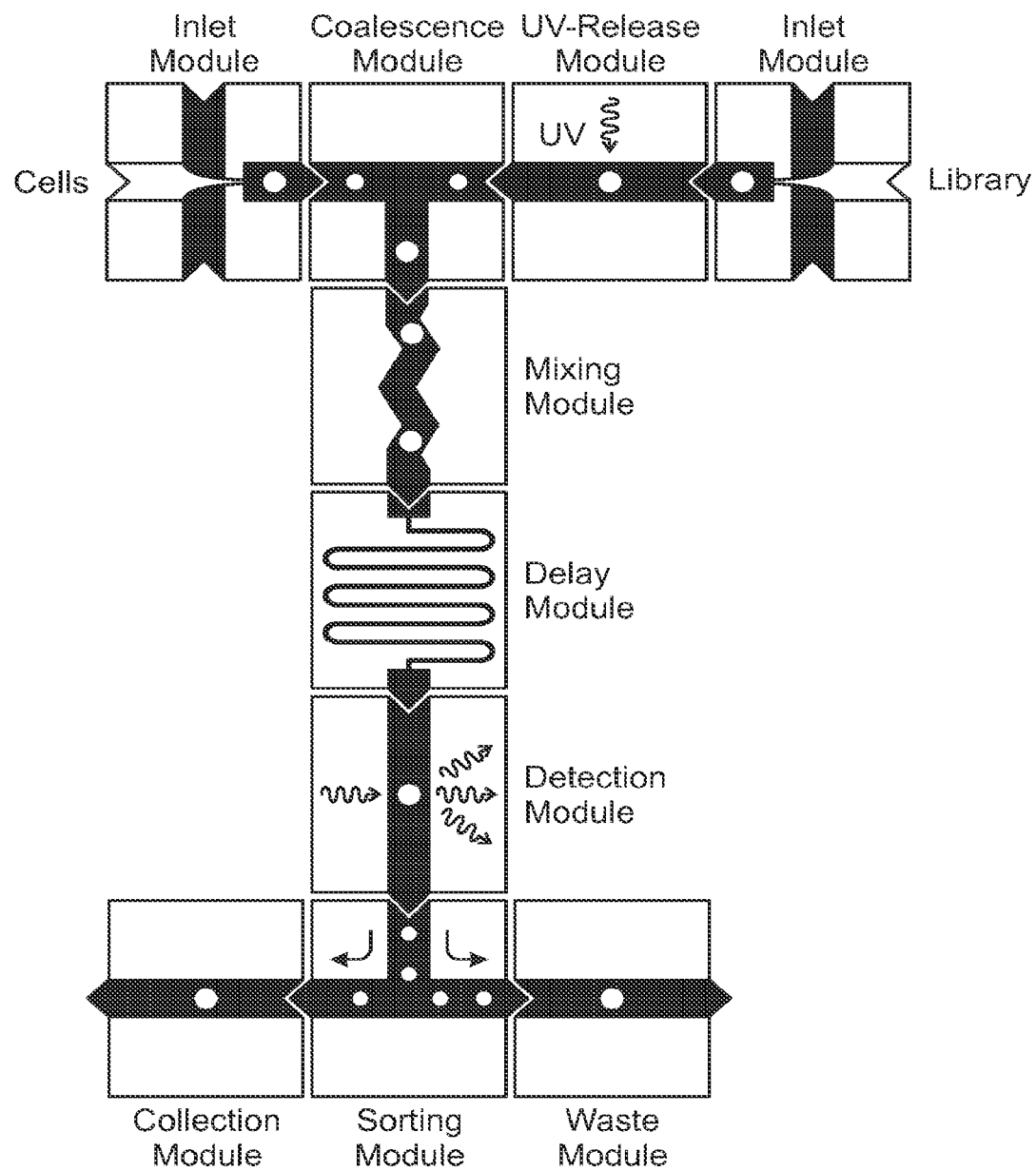
FIG. 1 is an schematic illustrating the interacting modules of a microfluidic device of the present invention.

The microfluidic devices and methods of use described herein are based on the creation and electrical manipulation of aqueous phase droplets completely encapsulated by an inert fluorocarbon oil stream. This combination enables electrically addressable droplet generation, highly efficient droplet coalescence, precision droplet breaking and recharging, and controllable single droplet sorting. Additional passive modules include multi-stream droplet formulations, mixing modules, and precision break-up modules. The integration of these modules is an essential enabling technology for a droplet based, high-throughput microfluidic reactor system. The microfluidic devices of the present invention can use a flow-focusing geometry to form the droplets. For example, a water stream can be infused from one channel through a narrow constriction; counter propagating oil streams (preferably fluorinated oil) hydrodynamically focus the water stream and stabilize its breakup into micron size droplets as it passes through the constriction. In order to form droplets, the viscous forces applied by the oil to the water stream must overcome the water surface tension. The generation rate, spacing and size of the water droplets is controlled by the relative flow rates of the oil and the water streams and nozzle geometry. While this emulsification technology is extremely robust, droplet size and rate are tightly coupled to the fluid flow rates and channel dimensions. Moreover, the timing and phase of the droplet production cannot be controlled. To overcome these limitations, the microfluidic devices of the present invention can incorporate integrated electric fields, thereby creating an electrically addressable emulsification system. In one embodiment, this can be achieved by applying high voltage to the aqueous stream and charge the oil water interface. The water stream behaves as a conductor while the oil is an insulator; electrochemical reactions charge the fluid interface like a capacitor. At snap-off, charge on the interface remains on the droplet. The droplet size decreases with increasing field strength. At low applied voltages the electric field has a negligible effect, and droplet formation is driven exclusively by the competition between surface tension and viscous flow, as described above. The microfluidic, droplet-based reaction-confinement system of the present invention can further include a mixer which combines two or more reagents to initiate a chemical reaction. Multi-component droplets can easily be generated by bringing together streams of materials at the point where droplets are made. However, all but the simplest reactions require multiple steps where new reagents are added during each step. In droplet-based microfluidic devices, this can be best accomplished by combining {i.e. coalescing) different droplets, each containing individual reactants. However, this is particularly difficult to achieve in a microfluidic device because surface tension, surfactant stabilization, and drainage forces all hinder droplet coalescence; moreover, the droplets must cross the stream lines that define their respective flows and must be perfectly synchronized to arrive at a precise location for coalescence. The microfluidic devices of the present invention overcome these difficulties by making use of electrostatic charge, placing charges of opposite sign on each droplet, and applying an electric field to force them to coalesce. By way of non-limiting example, a device according to the present invention can include two separate nozzles that generate droplets with different compositions and opposite charges. The droplets are brought together at the confluence of the two streams. The electrodes used to charge the droplets upon formation also provide the electric field to force the droplets across the stream lines, leading to coalescence. In the absence of an electric field, droplets in the two streams do not in general arrive at the point of confluence at exactly the same time. When they do arrive synchronously the oil layer separating the droplets cannot drain quickly enough to facilitate coalescence and as a result the droplets do not coalesce. In contrast, upon application of an electric field, droplet formation becomes exactly synchronized, ensuring that droplets each reach the point of confluence simultaneously {i.e., paired droplets).

Moreover, since the droplets are oppositely charged they are attracted to one another, which forces them to traverse the fluid stream lines and contact each other, thereby causing them to coalesce. The remarkable synchronization of the droplet formation results from coupling of the break-off of each of the pair of droplets as mediated by the electric field. The use of oppositely charged droplets and an electric field to combine and mix reagents is extremely robust, and 100% of the droplets coalesce with their partner from the opposite stream.

Other embodiments of the microfluidic devices of the present invention can include a droplet sorter. The contents of individual droplets must be probed, and selected droplets sorted into discreet streams. In one embodiment, such sorting in microfluidic devices can be accomplished through the use of mechanical valves. In another embodiment of the present invention, the use of electrostatic charging of droplets provides an alternate means that can be precisely controlled, can be switched at high frequencies, and requires no moving parts. Electrostatic charge on the droplets enables drop-by-drop sorting based on the linear coupling of charge to an external electric field. As an example, a T-junction bifurcation that splits the flow of carrier fluid equally will also randomly split the droplet population equally into the two streams. However, a small electric field applied at the bifurcation precisely dictates which channel the drops enter. Varying the direction of the field varies the direction of the sorted droplets. The large forces that can be imparted on the droplets and the short time required to switch the field make this a fast and robust sorting engine with no moving parts; thus the processing rate is limited only by the rate of droplet generation and electric field switching time, and can easily exceed 20,000 per second.

Accordingly, in one embodiment the present invention provides a microfluidic device comprising a microfabricated substrate comprising at least one inlet channel adapted to carry at least one dispersed phase fluid and at least one main channel adapted to carry a continuous phase fluid, where inlet channel is in fluid communication with the main channel at one or more inlet modules such that the dispersed phase fluid is immiscible with the continuous phase fluid and forms a plurality of droplets in the continuous phase fluid; a coalescence module, where an electric field is applied to cause two or more droplets to coalesce; and c) a detection module including a detection apparatus for evaluating the contents and/or characteristics of the coalesced droplets produced in the coalescence module. The microfabricated substrate can further comprise one or more sorting modules, collection modules, waste modules, branch channels, delay modules, mixing modules and/or UV release modules, or any combinations thereof in any order. FIG. 1.

The present invention also provides methods of creating a nanoreactor. The method includes a) providing a microfabricated substrate comprising at least one inlet channel adapted to carry at least one dispersed phase fluid and at least one main channel adapted to carry a continuous phase fluid, where the inlet channel is in fluid communication with the main channel at one or more inlet modules, and where the dispersed phase fluid is immiscible with the continuous phase fluid; b) flowing a first dispersed phase fluid through a first inlet channel such that the first dispersed phase fluid forms one or more droplets in the continuous phase fluid; c) flowing at least a second dispersed phase fluid through an at least second inlet channel such that the second dispersed phase fluid forms one or more droplets in the continuous phase fluid; and d) coalescing at least one droplet formed in step (b) with at least one droplet formed in step (c) under the influence of an electric field, thereby producing a nanoreactor.

The present invention also provides a method for manipulating a nanoreactor. The method includes providing a nanoreactor as described herein; providing a plurality of electrically addressable channel bearing microfluidic modules integrally arranged with each other on a microfabricated substrate so as to be in fluid communication and providing a control system for manipulating the nanoreactor.

The present invention also provides methods of manipulating biological/chemical material. The method includes a) providing a microfabricated substrate comprising at least one inlet channel adapted to carry at least one dispersed phase fluid and at least one main channel adapted to carry a continuous phase fluid, where the inlet channel is in fluid communication with the main channel at one or more inlet modules, and where the dispersed phase fluid is immiscible with the continuous phase fluid; b) flowing a first dispersed phase fluid comprising a first biological/chemical material through a first inlet channel such that the first dispersed phase fluid resides as one or more droplets in the continuous phase fluid; c) flowing at least a second dispersed phase fluid comprising a second biological/chemical material through a second inlet channel such that the second dispersed phase fluid resides as one or more droplets in the continuous phase fluid; d) slowing or stopping at least one droplet formed in step (b) by exerting a dielectrophoretic force onto the droplet; e) coalescing at least one droplet formed in step (c) with the droplet slowed or stopped in step (d) under the influence of an electric field within a coalescence module, thereby producing a nanoreactor; f) incubating the nanoreactor within a delay module; and g) interrogating the nanoreactor for a predetermined characteristic within a detection module. Slowing or stopping the droplets from step (b) allows pairing of the droplets from step (c) before they move to the location (e) where they are driven to coalesce by an electric field, or passively by passing through a narrowing of the channel.

In step (d), the pairing of droplets from (b) and (c) may be achieved in one of three ways: (i) using the dielectrophoretic force produced by the electric field gradient; (ii) using droplets of two different sizes, which works best when one droplet is comparable to the channel width and one droplet is smaller than the channel width, so that the smaller droplet catches up to the larger droplet; and (iii) the droplet in steps (b) and (c) have different viscosities, and thus, move at different velocities. Preferably, the droplets are of different sizes, and more preferably, the larger droplet has enough volume so that it would have a diameter greater than the channel width if it were spherical.

Methods of soiling biological/chemical material, although frequently desired, is not necessary in order to use the devices or practice the methods of the present invention. In particular, the devices and methods of the invention also include embodiments wherein the biological/chemical material is analyzed and/or identified, but is not sorted. The generation of nanoreactors through the coalescence of two droplets, although frequently desired, is not necessary in order to use the devices or practice the methods of the present invention. In particular, the devices and methods of the invention also include embodiments wherein the biological/chemical material is sorted without a coalescence event.

Substrates

The present invention also provides methods of producing a microfluidic device. The method of producing a microfluidic device comprises one or more of the following steps in any combination: 1) hard lithography, 2) soft lithography, 3) extraction and/or punch though, 4) bonding, 5) channel coating, 6) interconnect assembly, 7) electrode injection and 8) waveguide injection and fiber installation. The foregoing steps are described in more detail herein.

An "analysis unit" is a microfabricated substrate, e.g., a microfabricated chip, having at least one inlet channel, at least one main channel, at least one coalescence module, and at least one detection module. The analysis unit can further contain one or more sorting module. The sorting module can be in fluid communication with branch channels in communication with one or more outlet modules (collection module or waste module). For sorting, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A device according to the invention may comprise a plurality of analysis units.

A variety of channels for sample flow and mixing can be microfabricated on a single chip and can be positioned at any location on the chip as the detection or sorting modules, e.g., for kinetic studies. A plurality of analysis units of the invention may be combined in one device. Microfabrication applied according to the invention eliminates the dead time occurring in conventional gel electrophoresis or flow cytometric kinetic studies, and achieves a better time-resolution. Furthermore, linear arrays of channels on a single chip, i.e., a multiplex system, can simultaneously detect and sort a sample by using an array of photo multiplier tubes (PMT) for parallel analysis of different channels. This arrangement can be used to improve throughput or for successive sample enrichment, and can be adapted to provide a very high throughput to the microfluidic devices that exceeds the capacity permitted by conventional flow sorters. Circulation systems can be used in cooperation with these and other features of the invention. Positive displacement pressure driven flow is a preferred way of controlling fluid flow and electric fields and electric field gradients are a preferred way of manipulating droplets within that flow.

Microfabrication permits other technologies to be integrated or combined with flow cytometry on a single chip, such as PCR, moving cells using optical tweezer/cell trapping, transformation of cells by electroporation, μTAS, and DNA hybridization. Detectors and/or light filters that are used to detect cellular characteristics of the reporters can also be fabricated directly on the chip. Preferably, detectors are off-chip free space optics or off-chip electronics with on-chip leads.

A device of the invention can be microfabricated with a sample solution reservoir or well or other apparatus for introducing a sample to the device, at the inlet module, which is typically in fluid communication with an inlet channel. A reservoir may facilitate introduction of molecules or cells into the device and into the sample inlet channel of each analysis unit. An inlet module may have an opening such as in the floor of the microfabricated chip, to permit entry of the sample into the device. The inlet module may also contain a connector adapted to receive a suitable piece of tubing, such as liquid chromatography or HPLC tubing, through which a sample may be supplied. Such an arrangement facilitates introducing the sample solution under positive pressure in order to achieve a desired infusion rate at the inlet module.

A microfabricated device of the invention is preferably fabricated from a silicon microchip or silicon elastomer. The dimensions of the chip are those of typical microchips, ranging between about 0.5 cm to about 7.5 cm per side and about 1 micron to about 1 cm in thickness. A microfabricated device can be transparent and can be covered with a material having transparent properties, such as a glass coverslip, to permit detection of a reporter, for example, by an optical device such as an optical microscope.

The device of the present invention can comprise inlet and outlet interconnects. The interconnections, including tubes, must be extremely clean and make excellent bonding with the PDMS surface in order to allow proper operation of the device. The difficulty in making a fluidic connection to a microfluidic device is primarily due to the difficulty in transitioning from a macroscopic fluid line into the device while minimizing dead volume. Development of a commercial microfluidic platform requires a simple, reliable fluidic interconnect in order to reduce the chance of operator and error leaks. The curing and manufacturing of the PDMS slab with the tubes already placed on the silicon wafer accomplish these goals.

The template process can include, but is not limited to, the following features. In order to minimize contamination and leakage, process operations that allow for greater reproducibility and reliability are improved. Tubes and interconnects for the PDMS slab can be cured in place. The tubes and interconnects can be placed in position by applying a UV-cured adhesive to allow for holding the tubes in place on the silicone wafer. Once the tubes are placed in position, PDMS can be poured over the wafer and cured. The cured PDMS, along with the tubes in place, can be peeled off of the silicone wafer easily. This process can be applied to fluidics channels as well as other connection channels. Once the adhesive is applied onto the wafer, the process will allow for quick templating of PDMS slabs with exact reproducibility of channel locations and cleanliness. Tubes of any size can be implemented for this process. This process allows for less stress on the interconnection joints and smaller interconnection footprints in the device.

In one embodiment, small interconnects based on creating a face seal between the tubing and the device are used. A grommet may be placed into either a tapered hole or a hole with perpendicular walls. In one embodiment, the raised contact surface between the two sides is formed on the tubing side instead of the device side. In another embodiment, the sealing feature can be molded into the device. In yet another embodiment, a possible interconnect can be molded and bonded on a glass substrate directly from PDMS. In this embodiment, a thin film of PDMS can be simultaneously formed and bonded to the top of the glass slide and permits the use of isolated patterned electrodes and heating elements beneath the fluid channels. If not required, the seals could be made without the top skin. The raised contact surface could also be built into the tubing side. The sealing surface on the tubing side of the connection can be formed directly into the face of the tubing, although a separate piece secured to the tubing assembly/retaining nut may also be used.

The tubing side of the interconnect can be mounted into a retaining block that provides precise registration of the tubing, while the microfluidic device can be positioned accurately in a carrier that the retaining block would align and clamp to. The total dead volume associated with these designs would be critically dependent on how accurately the two mating surfaces could be positioned relative to each other, the maximum force required to maintain the seal would be limited by the exact shape and composition of the sealing materials as well as the rigidity and strength of the device itself. The shapes of the mating surfaces can be tailored to the minimal leakage potential, sealing force required, and potential for mis-alignment. By way of non-limiting example, the single ring used in the fluidic interconnects can be replaced with a series of rings of appropriate cross-sectional shape.

The device of the present invention can comprise a layer, such as a glass slide, which is perforated for functional interconnects, such as fluidic, electrical, and/or optical interconnects, and sealed to the back interface of the device so that the junction of the interconnects to the device is leak-proof. Such a device can allow for application of high pressure to fluid channels without leaking.

A silicon substrate containing the microfabricated flow channels and other components is preferably covered and sealed, most preferably with a transparent cover, e.g., thin glass or quartz, although other clear or opaque cover materials may be used. When external radiation sources or detectors are employed, the detection module is covered with a clear cover material to allow optical access to the cells. For example, anodic bonding to a "PYREX" cover slip can be accomplished by washing both components in an aqueous $H_2SO_4/H_2O_2$ bath, rinsing in water, and then, for example, heating to about 350° C. while applying a voltage of 450 V.

The present invention provides improved methods of bonding PDMS to incompatible media. Normal methods of bonding various materials (plastic, metals, etc) directly to materials such as PDMS, silicone, Teflon, and PEEK using traditional bonding practices (adhesives, epoxies, etc) do not work well due to the poor adhesion of the bonding agent to materials such as PDMS. Normal surface preparation by commercially available surface activators has not worked well in microfluidic device manufacturing. This problem is eliminated by treating the PDMS surface to be bonded with high intensity oxygen or air plasma. The process converts the top layer of PDMS to glass which bonds extremely well with normal adhesives. Tests using this method to bond external fluid lines to PDMS using a UV-cure adhesive (Loctite 352, 363, and others) resulted in a bond that is stronger than the PDMS substrate, resulting in fracture of the PDMS prior to failure of the bond. The present method combines high radiant flux, wavelength selection, and cure exposure time to significantly enhance the bond strength of the adhesive.

Channels

The invention provides microfluidic devices having channels that form the boundary for a fluid. The channels of the device carry a mixture of incompatible or immiscible fluids, such as an oil-water mixture. Droplets of aqueous solution containing a biological/chemical material are dispersed within the oil or other incompatible solvent. Each droplet of this multi-phase mixture can encapsulate one or more molecules, particles, or cells. The droplets are trapped and their boundaries are defined by channel walls, and therefore they do not diffuse and/or mix. Individual particles or molecules can be separately compartmentalized inside individual droplets. These droplets can be analyzed, combined with other droplets (e.g. to react droplet contents) and analyzed, and then sorted. Thus, the invention also provides methods for analyzing, combining, detecting and/or sorting of biological/chemical materials.

The channels present in the device can be made with micron dimensions and the volume of the detection module is precisely controlled. The planar geometry of the device allows the use of high numerical aperture optics, thereby increasing the sensitivity of the system. Because the system is entirely self-contained, there is no aerosol formation, allowing for much safer sorting of biohazardous materials. Materials sorted in the device are compartmentalized within individual droplets of an aqueous solution traveling in a flow of a second, incompatible or immiscible solution. Thus, there is no problem with the material diffusing or exchanging positions, even when sorting or analyzing extremely small particles, molecules, or reagents. In a preferred embodiment, water droplets are extruded into a flow of oil, but any fluid phase may be used as a droplet phase and any other incompatible or immiscible fluid or phase may be used as a barrier phase.

A "channel," as used herein, means a feature on or in a device (e.g., a substrate) that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have an aspect ratio (length to average cross-sectional dimension) of at least 2:1, more typically at least 3:1, 5:1, or 10:1. As used herein, a "cross-sectional dimension," in reference to a fluidic or microfluidic channel, is measured in a direction generally perpendicular to fluid flow within the channel. An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary. Of course, in some cases, larger channels, tubes, etc. can be used to store fluids in bulk and/or deliver a fluid to the channel.

In some embodiments, the dimensions of the channel may be chosen such that fluid is able to freely flow through the channel, for example, if the fluid contains cells. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, etc.

A "main channel" is a channel of the device of the invention which permits the flow of molecules, cells, small molecules or particles past a coalescence module for coalescing one or more droplets, a detection module for detection (identification) or measurement or a droplet and a sorting module, if present, for sorting a droplet based on the detection in the detection module. The coalescence, detection and/or sorting modules can be placed or fabricated into the main channel. The main channel is typically in fluid communication with an inlet channel or inlet module. An "inlet channel" permits the flow of molecules, cells, small molecules or particles into the main channel. One or more inlet channels communicate with one or more means for introducing a sample into the device of the present invention. The inlet channel communicates with the main channel at an inlet module. The main channel is also typically in fluid communication with an outlet module and optionally with branch channels, each of which may have a collection module or waste module. These channels permit the flow of cells out of the main channel.

Channels of the device of the present invention can be formed from silicon elastomer (e.g. RTV), urethane compositions, of from silicon-urethane composites such as those available from Polymer Technology Group (Berkeley, Calif.), e.g. PurSil™ and CarboSil™. The channels may also be coated with additives or agents, such as surfactants, TEFLON, or fluorinated oils such as octadecafluoroctane (98%, Aldrich), Fluorinert (FC-3283; 3M), or fluorononane, any of which can be modified to contain a fluorosurfactant. Fluorinated oils have favorable properties including chemical inertness, high gas permeability, and biocompatibility, which are desirable in microfluidic applications. TEFLON is particularly suitable for silicon elastomer (RTV) channels, which are hydrophobic and advantageously do not absorb water, but they may tend to swell when exposed to an oil phase. Swelling may alter channel dimensions and shape, and may even close off channels, or may affect the integrity of the chip, for example by stressing the seal between the elastomer and a coverslip. Urethane substrates do not tend to swell in oil but are hydrophillic, they may undesirably absorb water, and tend to use higher operating pressures. Hydrophobic coatings may be used to reduce or eliminate water absorption. Absorption or swelling issues may also be addressed by altering or optimizing pressure or droplet frequency (e.g. increasing periodicity to reduce absorption). RTV-urethane hybrids may be used to combine the hydrophobic properties of silicon with the hydrophilic properties of urethane.

The channels of the invention are microfabricated, for example by etching a silicon chip using conventional photolithography techniques, or using a micromachining technology called "soft lithography" as described by Whitesides and Xia, Angewandte Chemie International Edition 37, 550 (1998). These and other microfabrication methods may be used to provide inexpensive miniaturized devices, and in the case of soft lithography, can provide robust devices having beneficial properties such as improved flexibility, stability, and mechanical strength. When optical detection is employed, the invention also provides minimal light scatter from molecule, cell, small molecule or particle suspension and chamber material. Devices according to the invention are relatively inexpensive and easy to set up. They can also be disposable, which greatly relieves many of the concerns of gel electrophoresis (for molecules), and of sterilization and permanent adsorption of particles into the flow chambers and channels of conventional FACS machines.

The channels of the device of the present invention can be of any geometry as described. However, the channels of the device can comprise a specific geometry such that the contents of the channel are manipulated, e.g., sorted, mixed, prevent clogging, etc.

For particles (e.g., cells) or molecules that are in droplets (i.e., deposited by the inlet module) within the flow of the main channel, the channels of the device are preferably rounded, with a diameter between about 2 and 100 microns, preferably about 60 microns, and more preferably about 30 microns at the cross-flow area or droplet extrusion region. This geometry facilitates an orderly flow of droplets in the channels. Similarly, the volume of the detection module in an analysis device is typically in the range of between about 10 femtoliters (fl) and 5000 fl, preferably about 40 or 50 fl to about 1000 or 2000 fl, most preferably on the order of about 200 fl. In preferred embodiments, the channels of the device, and particularly the channels of the inlet connecting to a droplet extrusion region, are between about 2 and 50 microns, most preferably about 30 microns.

A microfluidic device can include a bifurcation geometry designed in such a manner as to minimize fluidic shear forces on droplets during sorting. Known devices describe bifurcation geometries in which significant shear forces affect droplets during sorting. Specifically droplets may experience shear forces when moving under the influence of the sorting force across the width of the input channel prior to encountering the bifurcation, and droplets may experience shear forces at the bifurcation point which are applied in such a manner as to elongate or even tear the droplet apart.

A microfluidic device comprising channels having a bifurcation geometry can minimize these shear forces by (i) including a necked-down segment of the input channel upstream of the bifurcation where the droplet is diagnosed to make the sorting decision, and/or by (ii) including a flaired-out segment of the input channel immediately prior to the bifurcation, and/or by (iii) including a fork on the far wall of the bifurcation. The shear forces are minimized by component (i) because the sorting field is applied while the droplet is in the necked-down segment. Therefore, when the droplet exits the necked-down segment, the droplet is placed on fluid streamlines, which will carry it out the desired branch of the bifurcation. Furthermore, the droplet does not significantly encounter fluid streamlines, which follow the undesired branch of the bifurcation. The shear forces are minimized by component (ii) because the droplet does not significantly impact the far wall of the bifurcation at a point where it would experience fluid streamlines, which follow the undesired branch of the bifurcation. The shear forces are minimized by component (iii) because the fork serves to focus the two sets of fluid streamlines (i.e., the one set which follows one branch of the bifurcation, and the other set which follows the other branch of the bifurcation) away from each other.

A microfluidic device can include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

Channel design can force biological/chemical material moving along the center streamline through flow focus, e.g., using two dilution channels at the entrance of the channel to prevent attachment to the channel surface. This can also be used to prevent the surface attachment by cells.

Droplets at these dimensions tend to conform to the size and shape of the channels, while maintaining their respective volumes. Thus, as droplets move from a wider channel to a narrower channel they become longer and thinner, and vice versa. Droplets can be at least about four times as long as they are wide. This droplet configuration, which can be envisioned as a lozenge shape, flows smoothly and well through the channels. Longer droplets, produced in narrower channels, provides a higher shear, meaning that droplets can more easily be sheared or broken off from a flow, i.e. using less force. Droplets can also tend to adhere to channel surfaces, which can slow or block the flow, or produce turbulence. Droplet adherence is overcome when the droplet is massive enough in relation to the channel size to break free. Thus, droplets of varying size, if present, can combine to form uniform droplets having a so-called critical mass or volume that results in smooth or laminar droplet flow. Droplets that are longer than they are wide, preferably about four times longer than they are wide, generally have the ability to overcome channel adherence and move freely through the microfluidic device. Thus, in an exemplary embodiment with 60 micron channels, a typical free-flowing droplet is about 60 microns wide and 240 microns long. Droplet dimensions and flow characteristics can be influenced as desired, in part by changing the channel dimensions, e.g. the channel width.

The microfabricated devices of this invention most preferably generate round, monodisperse droplets. The droplets can have a diameter that is smaller than the diameter of the microchannel; i.e., preferably 40 to 100 μm when cells are used or 5 to 40 μm when reagents are used. Monodisperse droplets may be particularly preferably, e.g., in high throughput devices and other embodiments where it is desirable to generate droplets at high frequency and of high uniformity.

To prevent material (e.g., cells and other particles or molecules) from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. "TEFLON" is an example of a coating that has suitable surface properties.

The surface of the channels of the microfluidic device can be coated with any anti-wetting or blocking agent for the dispersed phase. The channel can be coated with any protein to prevent adhesion of the biological/chemical sample. For example, in one embodiment the channels are coated with BSA, PEG-silane and/or fluorosilane. For example, 5 mg/ml BSA is sufficient to prevent attachment and prevent clogging. In another embodiment, the channels can be coated with a cyclized transparent optical polymer obtained by copolymerization of perfluoro (alkenyl vinyl ethers), such as the type sold by Asahi Glass Co. under the trademark Cytop. In such an embodiment, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162, which patent is hereby incorporated by reference. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

The microfluidic device can include a syringe (or other glass container) that is treated with a vapor or solution of an appropriate PEG-silane to effect the surface PEG functionalization. The purpose for treating the walls of glass containers (e.g., syringes) with a PEG functionality is to prevent biological adhesion to the inner walls of the container, which frustrates the proper transfer of biological/chemical materials into the microfluidic device of the present invention.

The device of the present invention can comprise one or more fluid channels to inject or remove fluid in between droplets in a droplet stream for the purpose of changing the spacing between droplets.

The invention provides methods of cell manipulation by channel geometry. Most cells, especially mammalian cells intend to attach each other in suspension. The purpose of changing channel geometry is to detach the cell from aggregates and keep them separated from each other before they are encapsulated in the drops. The geometry of channel dimension can be changed to disturb the aggregates and break them apart by various methods, that can include, for example, geometric pinching and/or barricades. With geometric pinching, cells are forced through one or more narrow regions, whose dimension is smaller or comparable to the dimension of a single cell. With a barricade, a series of obstacles/impediments (barricades) are placed in the way of the moving cells to disturb the movement and break up the aggregates of cells.

The present invention provides methods to prevent channel clogging including methods of fluid pinching and surface coating. Some cells and polystyrene beads tend to attach to the PDMS/Glass surface. This is an undesired result as the accumulated beads can clog the channel, especially the narrow region (i.e. nozzle). Channel design and blocking reagent can be used in some embodiments to prevent the beads' attachment to the channel surface and to each other. Non-limiting examples include coating reagents and channel design. A coating reagent, such as BSA (or any other protein), is added to the bead buffer to coat the channel surface as well as the beads' surface. 5 mg/ml BSA has shown to be sufficient to prevent the beads' attachment. No clogging is observed in an experiment with 1 Oum diameter beads in a 30 um wide and 25 um deep nozzle device. With channel design, cells/beads are forced to move along the center streamline through flow focus—Using two dilution channels at the entrance of the beads' channel to prevent beads' attachment to the channel surface. This can also used to prevent the surface attachment by cells.

A typical analysis unit of the invention comprises a main inlet channel that is part of and feeds or communicates directly with a main channel, along with one or more sample inlet channels in communication with the main channel at a inlet module situated downstream from the main inlet. In one embodiment, each different sample inlet channel preferably communicates with the main channel at a different inlet module. In another embodiment, different sample inlet channels can communication with the main channel at the same inlet module. The inlet channel is further connected to a means for introducing a sample to said device. The means can be a well or reservoir. The well or reservoir further include an acoustic actuator. The means can be temperature controlled. The main channel is further connected to a means for collecting a sample from said device. The means can be a well or reservoir. The means can be temperature controlled.

The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

The main channel in turn can communicate with two or more branch channels at the sorting module or "branch point", if present, forming, for example, a T-shape or a Y-shape. Other shapes and channel geometries may be used as desired.

The device of the present invention can comprise one more means for chromatographically sorting the sample prior to droplet formation. The means can be in fluid communication with the inlet channel and/or the inlet module. Preferably, the means is a channel. The sample can be sorted by size, charge, hydrophobicity, atomic mass, etc. The separating can be done isocratic or by generating a gradient chemically, (for example using salt or hydrophobicity), electrically, by pressure, or etc. For size exclusion, the channel can be preloaded with Sepharose. The sample is then loaded at one end, and the droplets are formed at an opposing end. The sample separates by size prior to becoming incorporated within a droplet.

Fluids

The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention.

The flow stream in the main channel is typically, but not necessarily, continuous and may be stopped and started, reversed or changed in speed. Prior to sorting, a liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e. g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar, or turbulent in some cases. The continuous fluidic stream may be, e.g., solid or hollow (i.e., containing a second fluid internally, for example, as in a hollow tube). It is to be understood that wherever "tube" is used herein, the structure can be a hollow, a solid or filled (i.e., not hollow) stream, a stream that includes a central core and a surrounding layer or layers, any of which can be selectively reacted with any others, or solidified, or the like. In some cases, the central core is hollow, and/or fluid may be removed from a hardened surrounding fluid to produce a hollow tube. The continuous phase fluid can be a non-polar solvent. The continuous phase fluid can be a fluorocarbon oil.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. A "droplet," as used herein, is an isolated portion of a first fluid that completely surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. As used herein, a first entity is "surrounded" by a second entity if a closed loop can be drawn or idealized around the first entity through only the second entity. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels. The label can be a DNA tag, dyes or quantum dot, or combinations thereof.

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion maybe a oil in water emulsion. In that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

As used herein, the term "NanoReactor" and its plural encompass the terms "droplet", "microdrop" or "microdroplet" as defined herein, as well as an integrated system for the manipulation and probing of droplets, as described in detail herein. Nanoreactors as described herein can be 0-100 µm (e.g., 5, 10, 15, 20, 25, 30, 35, 40, 45, 50, 55, 60, 65, 70, 75, 80, 85, 90, 95, 100)

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one mat is immiscible with the droplet forming fluid. The fluid passing through the main channel can be a non-polar solvent, most preferably decane (e g., tetradecane or hexadecane), fluorocarbon oil or another oil (for example, mineral oil).

The dispersed phase fluid may also contain biological/chemical material (e.g., molecules, cells, or other particles) for combination, analysis and/or sorting in the device. The droplets of the dispersed phase fluid can contain more than one particle or can contain no more than one particle. For example, where the biological material comprises cells, each droplet preferably contains, on average, no more than one cell. The droplets can be detected and/or sorted according to their contents.

The fluids used in the invention may contain one or more additives, such as agents which reduce surface tensions (surfactants). Surfactants can include Tween, Span, fluorosurfactants, and other agents that are soluble in oil relative to water. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electroosmotic flow control, electrophoresis and dielectrophoresis (Fulwyer, *Science* 156, 910 (1974); Li and Harrison, Analytical Chemistry 69, 1564 (1997); Fiedler, et al. Analytical Chemistry 70, 1909-1915 (1998); U.S. Pat. No. 5,656,155). Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Without being bound by any theory, electro-osmosis is believed to produce motion in a stream containing ions e.g. a liquid such as a buffer, by application of a voltage differential or charge gradient between two or more electrodes. Neutral (uncharged) molecules or cells can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. Where an aqueous phase is combined with an oil phase, aqueous droplets are encapsulated or separated from each other by oil. Typically, the oil phase is not an electrical conductor and may insulate the droplets from the electro-osmotic field. In this example, electro-osmosis may be used to drive the flow of droplets if the oil is modified to carry or react to an electrical field, or if the oil is substituted for another phase that is immiscible in water but which does not insulate the water phase from electrical fields.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or molecules, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. Likewise, the polarizability of droplets also depends upon their size, shape and composition. For example, droplets that contain salts can be polarized. According to formulas provided in Fiedler, et al. *Analytical Chemistry* 70, 1909-1915 (1998), individual manipulation of single droplets requires field differences (mhomogeneities) with dimensions close to the droplets.

Manipulation is also dependent on permittivity (a dielectric property) of the droplets and/or particles with the suspending medium. Thus, polymer particles, living cells show negative dielectrophoresis at high-field frequencies in water. For example, dielectrophoretic forces experienced by a latex sphere in a 0.5 MV/m field (10 V for a 20 micron electrode gap) in water are predicted to be about 0.2 piconewtons (pN) for a 3.4 micron latex sphere to 15 pN for a 15 micron latex sphere (Fiedler, et al. *Analytical Chemistry* 70, 1909-1915 (1998)). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See U.S. Pat. No. 5,454,472.

Radiation pressure can also be used in the invention to deflect and move objects, e.g. droplets and particles (molecules, cells, particles, etc.) contained therein, with focused beams of light such as lasers. Flow can also be obtained and controlled by providing a pressure differential or gradient between one or more channels of a device or in a method of the invention.

Molecules, cells or particles (or droplets containing molecules, cells or particles) can be moved by direct mechanical switching, e.g., with on-off valves or by squeezing the channels. Pressure control may also be used, for example, by raising or lowering an output well to change the pressure inside the channels on the chip. See, e.g., the devices and methods described U.S. Pat. No. 6,540,895. These methods and devices can further be used in combination with the methods and devices described in pending U.S. Patent Application Publication No. 20010029983 and 20050226742. The "pump and valve" drive systems are particularly preferred. They are rapid, efficient, economical, and relatively easy to fabricate and control. Additionally, they do not rely on electrical fields or electrical charges, which may be harder to control and in some cases may potentially affect the droplet contents. Different switching and flow control mechanisms can be combined on one chip or in one device and can work independently or together as desired.

The device can exchange constituents within a droplet through the use of fluid flow in such a way that the droplet, while in a first immiscible fluid, is exposed to a second immiscible fluid such that constituents within the droplet that are immiscible in the first immiscible fluid are soluble in the second immiscible fluid, In one example, an aqueous droplet containing a chemical reaction produces by-products that are soluble in a lipid solvent. The chemical reaction is performed in a water-environment in a silicon-based solvent. After the chemical reaction occurs, the droplet is exposed to an organic-oil based solvent where the chemical byproducts are allowed to diffuse out of the droplet. The resulting droplet is then assayed for cell-killing activity by combining the droplet with live cells. Alternatively, the change in the non-aqueous fluid flow is used to add a particular constituent from the second immerscible fluid to diffuse into the aqueous drop before the droplet is returned to the 100% first immiscible fluid flow.

The concentration (i.e., number) of molecules, cells or particles in a droplet can influence sorting efficiently and therefore is preferably optimized. In particular, the sample concentration should be dilute enough that most of the droplets contain no more than a single molecule, cell or particle, with only a small statistical chance that a droplet will contain two or more molecules, cells or particles. This is to ensure that for the large majority of measurements, the level of reporter measured in each droplet as it passes through the detection module corresponds to a single molecule, cell or particle and not to two or more molecules, cells or particles.

The parameters which govern this relationship are the volume of the droplets and the concentration of molecules, cells or particles in the sample solution. The probability that a droplet will contain two or more molecules, cells or particles ($P_{\leq 2}$) can be expressed as $$P_{\leq 2} = 1 - \{1 + [\text{cell}] \times V\} \times e^{-[\text{cell}] \times V}$$

where "[cell]" is the concentration of molecules, cells or particles in units of number of molecules, cells or particles per cubic micron ($\mu m^3$), and V is the volume of the droplet in units of $\mu m^3$.

It will be appreciated that $P_{\leq 2}$ can be minimized by decreasing the concentration of molecules, cells or particles in the sample solution. However, decreasing the concentration of molecules, cells or particles in the sample solution also results in an increased volume of solution processed through the device and can result in longer run times. Accordingly, it is desirable to minimize to presence of multiple molecules, cells or particles in the droplets (thereby increasing the accuracy of the sorting) and to reduce the volume of sample, thereby permitting a sorted sample in a reasonable time in a reasonable volume containing an acceptable concentration of molecules, cells or particles.

The maximum tolerable $P_{\leq 2}$ depends on the desired "purity" of the sorted sample. The "purity" in this case refers to the fraction of sorted molecules, cells or particles that posses a desired characteristic (e.g., display a particular antigen, are in a specified size range or are a particular type of molecule, cell or particle). The purity of the sorted sample is inversely proportional to $P_{\leq 2}$. For example, in applications where high purity is not needed or desired a relatively high $P_{\leq 2}$ (e.g., $P_{\leq 2}$=0.2) may be acceptable. For most applications, maintaining $P_{\leq 2}$ at or below about 0.1, preferably at or below about 0.01, provides satisfactory results.

A sample solution containing a mixture or population of molecule, cells or particles in a suitable fluid (such as a liquid or buffer described above) is supplied to the sample inlet channel, and droplets of the sample solution are introduced, at the inlet module, into the flow passing through the main channel. The force and direction of flow can be controlled by any desired method for controlling flow, for example, by a pressure differential, by valve action or by electro-osmotic flow (e.g., produced by one or more electrodes or patterned electrically conductive layers at inlet and/or outlet modules). This permits the movement of the cells into one or more desired branch channels or outlet modules.

Both the fluid comprising the droplets and the fluid carrying the droplets (i.e., the aqueous and non-polar fluids) have, preferably, a relatively low Reynolds Number, for example $10^{-2}$. The Reynolds Number represents an inverse relationship between the density and velocity of a fluid and its viscosity in a channel of given length. More viscous, less dense, slower moving fluids over a shorter distance will have a lower Reynolds Number, and are easier to divert, stop, start, or reverse without turbulence. Because of the small sizes and slow velocities, microfabricated fluid systems are often in a low Reynolds number regime (Re<<1). In this regime, inertial effects, which cause turbulence and secondary flows, are negligible; viscous effects dominate the dynamics. These conditions are advantageous for sorting, and are provided by microfabricated devices of the invention. Accordingly the microfabricated devices of the invention are preferably if not exclusively operated at a low or very low Reynold's number.

The device of the present invention can be used to generate droplets whose composition may vary from one droplet to the next droplet due to any number of reasons (chemical reaction, sample preparation, etc). Within the same device, the droplets can be passed through a measurement volume in which the contents can be interrogated using various means (optical or electrical). The result of the measurement can be used to decide which flow path the droplets should take. The means of changing the flow path can be accomplished through mechanical, electrical, optical, or other technique as described herein or well known in the art.

The present invention provides methods for the determination of droplet size and rate information without the need for optical measurements on a microfluidic device. The need to control the timing between multiple events requires the determination of the exact time when a droplet passes a given point. It is also essential to know which channel a droplet enters. This method can significantly reduce the cost and complexity of such measurements.

The fluids used to generate droplets in microfluidic devices are typically immiscible liquids such as oil and water. These two materials generally have very different dielectric constants associated with them. These differences can be exploited to determine droplet rate and size for every drop passing through a small section of a microfluidic device. One method to directly monitor this variation in the dielectric constant measures the change in capacitance over time between a pair of closely spaced electrodes. This change in capacitance can be detected by the change in current measured in these electrodes:

$$i = V \frac{dC}{dt}$$

Where i is the current, V is the voltage applied across the electrodes, and dC/dt is the change in capacitance with time. Alternatively, the capacitance can be measured directly if a time varying voltage is applied to these same electrodes: i=CdV/dt Where C is the measured capacitance, and dV/dt is the change in voltage with time.

As a first approximation, the electrode pair can be determined as a parallel plate capacitor:

$$C = \varepsilon_o k \frac{A}{d}$$

Where $\varepsilon_0$ is the permittivity of free space, k is the effective dielectric constant (this changes every time a droplet passes through), A is the area of the capacitor and d is the electrode separation. The current measured in the device is then plotted as a function of time.

Inlet Module

An "inlet module" is an area of a microfabricated device that receives molecules, cells, small molecules or particles for coalescence, detection and/or sorting. The inlet module can contain one or more inlet channels, wells or reservoirs, openings, and other features which facilitate the entry of molecules, cells, small molecules or particles into the device. A chip may contain more than one inlet module if desired. The inlet module is in fluid communication with the main channel. The inlet module can include a junction between an inlet channel and the main channel of a device of the invention. The junction can permit the introduction of a pressurized fluid to the main channel. The inlet channel can be at an angle perpendicular to the flow of fluid in the main channel. The fluid introduced to the main channel through the inlet module is "incompatible" (i.e., immiscible) with the fluid in the main channel so that droplets of the fluid introduced through the inlet module are formed in the stream of continuous fluid in the main channel.

Embodiments of the invention are also provided in which there are two or more inlet modules introducing droplets of samples into the main channel. For example, a first inlet module may introduce droplets of a first sample into a flow of fluid (e.g., oil) in the main channel and a second inlet module may introduce droplets of a second sample into the flow of fluid in main channel, and so forth. The second inlet module is preferably downstream from the first inlet module (e.g., about 30 μm). The fluids introduced into the two or more different inlet modules can comprise the same fluid or the same type of fluid (e.g., different aqueous solutions). For example, droplets of an aqueous solution containing an enzyme are introduced into the main channel at the first inlet module and droplets of aqueous solution containing a substrate for the enzyme are introduced into the main channel at the second inlet module. Alternatively, the droplets introduced at the different inlet modules may be droplets of different fluids which may be compatible or incompatible. For example, the different droplets may be different aqueous solutions, or droplets introduced at a first inlet module may be droplets of one fluid (e.g., an aqueous solution) whereas droplets introduced at a second inlet module may be another fluid (e.g., alcohol or oil).

To obtain one droplet comprising a single element of a specific biological/chemical material (e.g., a cell), separation of biological/chemical material, and uniformity of the number density of biological/chemical materials in a microfluidic channel is desirable. Accordingly, the microfluidic device can include an acoustic actuator. The loaded sample (biological/chemical material) can be well mixed and separated in a small chamber by acoustic wave before sending out to the nozzle region for encapsulation. The frequency of the acoustic wave should be fine tuned so as not to cause any damage to the cells. The biological effects of acoustic mixing have been well studied (e.g., in the ink-jet industry) and many published literatures also showed that piezoelectric microfluidic device can deliver intact biological payloads such as live microorganisms and DNA.

The design of the acoustic resonant can use a Piezoelectric bimorph flat plate located on the side of the carved resonant in the PDMS slab. The resonant inlet can connect to the cell flow input channel and the outlet can connect to the cell flow pinching channel. The piezoelectric driving waveform can be carefully optimized to select the critical frequencies that can separate cells in fluids. There are five parameters to optimize beyond the frequency parameter and Lab electronics can be used to optimize the piezoelectric driving waveform. Afterwards, a low cost circuit can be designed to generate only the optimized waveform in a preferred microfluidic device.

Coalescence Module

The device of the invention also comprises one or more coalescence modules. A "coalescence module" is within or coincident with at least a portion of the main channel at or downstream of the inlet module where molecules, cells, small molecules or particles comprised within droplets are brought within proximity of other droplets comprising molecules, cells, small molecules or particles and where the droplets in proximity coalesce or combine their contents. The coalescence module can also include an apparatus, preferably one or more electrodes or patterned electrically conductive layers for generating a dielectrophoretic force. The dielectrophoretic force generated by one or more electrodes or patterned electrically conductive layers can slow or stop the droplets within the main channel thereby facilitating their proximity and resulting coalescence or combination.

Two or more precursor droplets in one or more droplet streams can be coalesced into a larger droplet by applying a voltage to produce an electric field. The voltage can be alternating. The electric field can be an AC electric field, or a DC electric field.

Figure 15A:
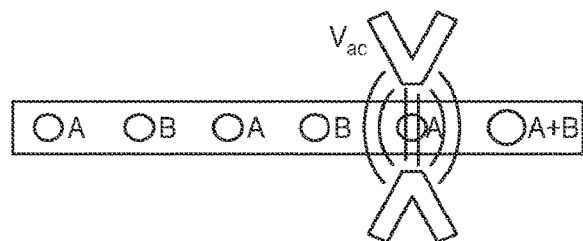
FIG. 15 (A) is a schematic illustrating dielectrophoretic stopping of droplet A allowing droplet B to contact A and coalesce. The dielectrophoretic force is not strong enough to stop the combined A+B and they move off in the stream. This is shown in the photomicrograph, FIG. 15 (B).
Figure 15B:
Figure 20D:
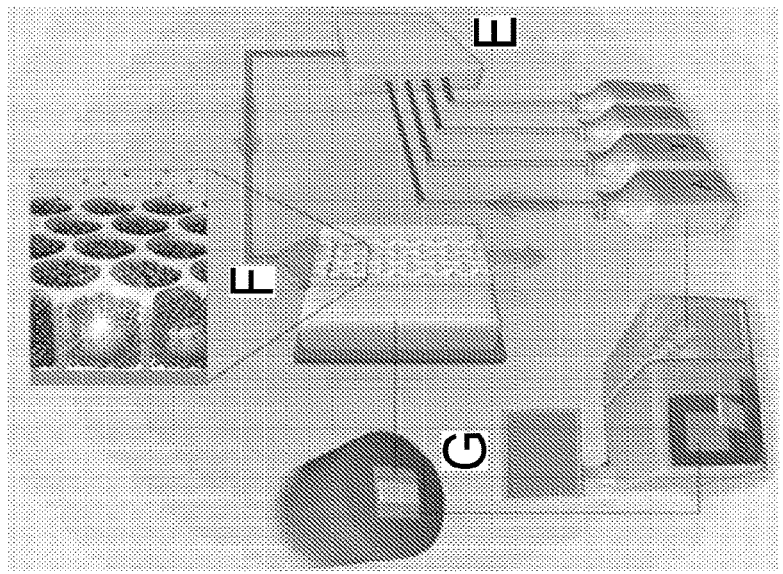
FIGS. 20A-D describe sample preparation and DNA sequencing on the 454 Instrument.
Figure 20A:
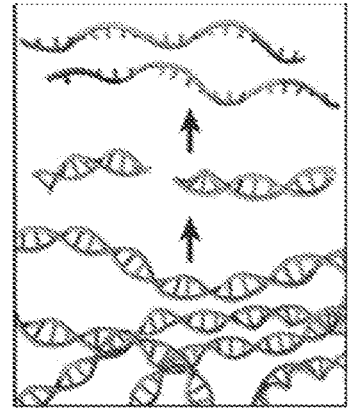
Figure 20C:
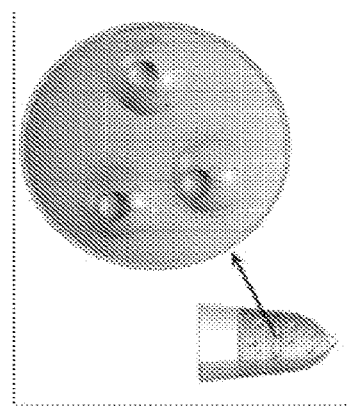
Figure 20C:
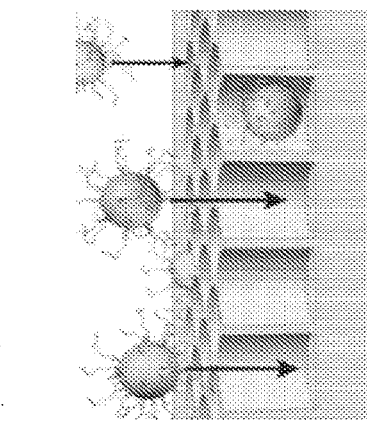
Figure 20C:
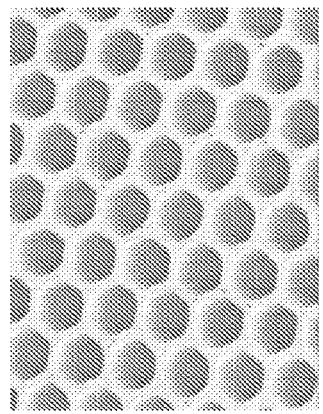
Figure 20B:
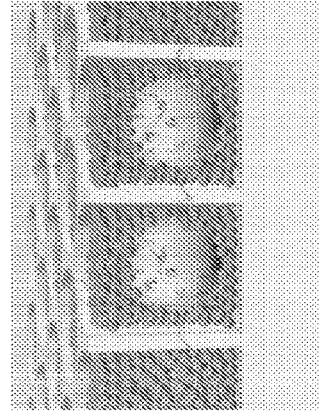
Figure 20B:
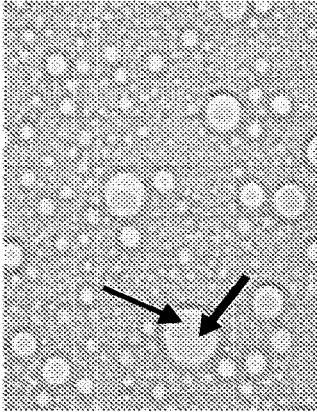

The coalescing influence can create a dielectrophoretic force that slows or stops a first precursor droplet relative to the velocity of the stream that carries the droplet. The first precursor droplet will remain slow or stopped until a second (or more) precursor droplet arrives and coalesces with the first precursor droplet due to interactions between the field induced dipoles in the droplets. The new droplet of increased volume is then too large to be held by the dielectric field and moves off under the influence of the flow of the continuous phase fluid. See FIGS. 15-17. No change in the applied voltage is required and the electric field remains constant. Both the trapping (slowing or stopping) of the precursor droplets and the release of the coalesced droplet can be passive. Once the new droplet of increased volume moves off, the next precursor droplet is then trapped in the field and the process repeated. The voltage can be tuned such that more than one droplet is coalesced with a trapped droplet. An advantage of coalescing more than one droplet with another is that it allows for pairwise combinations. Alternatively, a variation on this geometry will allow precise control of the droplet phase by temporarily shifting droplets to low velocity streamlines in the flow.

The precursor droplets can come at different times in the same fluid stream and subsequently coalesce. Alternatively, the precursor droplets can arrive together in different (e.g., two or more) fluid streams so that the droplets are in a substantially adjacent position with respect to each other when they come under the influence of the dielectrophoretic force and then subsequently coalesce due to the interactions between the field induced dipoles in the droplets. The different fluid streams can be substantially parallel.

The electric field gradient can be stronger for precursor droplets in a first parallel fluid stream than for precursor droplets in a second (or more) parallel fluid stream. Accordingly, it is only the precursor droplets from the first stream that are trapped, thereby preventing coalescence of precursor droplets in the other fluid stream(s) among each other in the case where the frequency of precursor droplets in the other stream(s) is greater than the frequency of precursor droplets in the first stream. In this manner the electric field can be changed to cause coalescence of only correct pairs of precursor droplets. Thus, in some embodiments the trapping and release of the droplets can be non-passive (i.e., based on whether the electric field is on or off).

The device can include channels for use in fluid control and other channels filled with a metal alloy for casting integrated metal alloy components (i.e., electrodes). Alternatively, the electrodes can be manufactured using other technologies (e.g., lithographically patterned electrodes made from indium tin oxide or a metal such as platinum). The microfluidic device can include metal alloy components useful for performing electrical functions on fluids, including but not limited to, coalescing droplets, charging droplets, sorting droplets, detecting droplets and shaking droplets to mix the contents of coalesced droplets. The device can contain more than one of the above mentioned components for more than one of the above mentioned functions.

The present invention also provides methods of manipulating biological/chemical material. In one embodiment, the first and second droplets can be brought into proximity prior to coalescence by slowing or stopping at least one droplet comprising a first biological/chemical material by exerting a dielectrophoretic force onto the droplet produced by an electric field gradient. In another embodiment, the first and second droplets can be brought into proximity prior to coalescence where the first and second droplet are of different size. In some embodiments, one of the first and second droplets can be the size of the channel width and the other droplet can be smaller than the channel width. In other embodiments, the larger droplet has enough volume so that it would have a diameter greater than the channel width if it were spherical. In a further embodiment, the first and second droplets can be brought into proximity prior to coalescence where the first and second droplet are of different viscosities and thus move at different velocities. Viscosity of a droplet can be changed by changing the content of the droplet. For example, glycerol can be added to a droplet to give it an increased viscosity.

In one embodiment, the method of manipulating biological and chemical material, further comprises coalescing at least one droplet with a droplet slowed or stopped under the influence of a dielectrophoretic force from an electric field gradient created within a coalescence module, thereby producing a nanoreactor.

The droplet size can be controlled such that the droplet formed from flowing a first dispersed phase fluid in a continuous phase fluid moves at a different velocity with respect to a droplet formed from flowing a second dispersed phase fluid in a continuous phase fluid, such that droplets arrive in pairs at a region where an electric field induces them to coalesce, thereby producing a nanoreactor. In some embodiments, greater than 50% of the droplets are paired. In other embodiments, greater than 75% of the droplets are paired.

The droplet viscosity can be controlled such that the droplet formed from flowing a first dispersed phase fluid in a continuous phase fluid moves at a different velocity with respect the droplet formed from flowing a second dispersed phase fluid in a continuous phase fluid, such that droplets arrive in pairs at a region where an electric field induces them to coalesce, thereby producing a nanoreactor. In some embodiments, greater than 50% of the droplets are paired. In other embodiments, greater than 75% of the droplets are paired.

The electrodes comprising metal alloy components may either terminate at fluid channels or be isolated from fluid channels. The electrodes can be constructed by filling the appropriate channels with metal alloy. One way this can be accomplished to use positive pressure injection of the metal alloy in a melted state, such as with a syringe, into the channels, and then cool the metal alloy to a solid form. Another example is to use negative pressure to suck the metal alloy in a melted state into the channels, and then cool the metal alloy to a solid form. This can be accomplished for example by use of capillary forces. Another method of construction can use any of the above mentioned embodiments, and then flush out the metal alloy in a melted state with another liquid to define the geometry of the metal alloy components. Another example is to use any of the above mentioned embodiments, and then use a localized cold probe to define a solid termination point for the metal alloy, and then cool the remaining metal alloy to a solid form. A further example is to use another material, such as microscopic solder spheres or UV curable conductive ink, to form a barrier between fluid and metal alloy channels, to define the geometry of the metal alloy components.

The device can include a combination of both integrated metal alloy components and a patterned electrically conductive layer. The patterned electrically conductive layer can have features patterned such that their boundaries are within a leak-proof seal. The device can have a patterned electrically conductive feature as one of two charging electrodes and one integrated metal alloy component as the other of two charging electrodes. Alternatively, the device can have metal alloy components as the two halves of a bowtie antenna and patterned electrically conductive features as the two halves of a pickup antenna for dielectric droplet detection.

The device can include a plurality of electrodes that are insulated from the fluid present in the device, and the method of operation including appropriate application of dielectrical signals and appropriate fluids. In known devices, the electrodes are typically in contact with the fluids in order to allow discharge of species that would otherwise screen the applied dielectric field. Whereas, in devices where the electrodes have been insulated from the fluid, this screening effect typically arises so quickly that the device is not useful for any significantly extended period of time. The drawbacks of electrodes in contact with the fluids vs. insulated electrodes are (a) degraded reliability against leaking (since the interface between the electrodes and the other components of the device may be more difficult to effect a leak-proof seal), and (b) degraded reliability against electrode corrosion (whose failure mode effects include failure of application of dielectric fields, and fluid channel contamination).

The device of the present invention comprising a plurality of electrodes that are insulated from the fluid present in the device counteracts this screening effect by extending the screening rise time and including a polarity switch for all of the different dielectric fields applied in the device. The screening rise time is extended by using fluids with dielectrical properties. A polarity switch for all of the different dielectric fields applied in the device is achieved by using an algorithm for dielectrical control, which switches the polarity of the dielectrical fields at a frequency sufficiently high to maintain proper dielectrical function of the device. This dielectrical control algorithm may also switch the polarity for the dielectric fields in a cascading, time controlled manner starting at the fluid origin point and progressing downstream, so that given fluid components experience one polarity at every point along their course. The device of the present invention can be used with metal alloy electrodes or using a combination of metal alloy electrodes and patterned conductive film electrodes.

In one embodiment, the invention provides a microfluidic device using injected electrodes. The interface between the microscopic electrode (typically 25 µm thick) and the macroscopic interconnect can easily fail if the joint between the two is flexed. The flexing of the joint can be eliminated by securing a firm material that serves to fasten, support, and reinforce the joint (i.e., a grommet) into the interface. In order to prevent flexing, the mating surface of the device can be manufactured from a hard material such as glass or plastic. The electrical connection with the external system can be made by securing the device such that it connects to a spring loaded contact, which is either offset from the grommet (thereby minimizing the force applied to the solder region), or centered on the grommet (as long as the contact does not touch the solder).

The metal alloy components are also useful for performing optical functions on fluids, including but not limited to, optical detection of droplets in a geometry which may include a mirror.

To prevent leakage of fluid out of electrodes placed within microfluidic channels, the microfluidic device can include a layer patterned with channels for fluid control, and another layer with patterned electrically conductive features, where the features are patterned such that their boundaries are within a leak-proof seal. The leak-proof seal can be achieved at the interface between the unpatterned areas of the fluid control layer and the unpatterned areas of the electrically conductive layer. The leak-proof seal can also be achieved by a third interfacial layer between the fluid control layer and the unpatterned areas of the electrically conductive layer. The third interfacial layer can or can not be perforated at specific locations to allow contact between the fluid and the electrically conductive layer. Electrical access ports can also be patterned in the fluid control layer.

The electrodes and patterned electrically conductive layers as described can be associated with any module of the device (inlet module, coalescence module, mixing module, delay module, detection module and sorting module) to generate dielectric or electric fields to manipulate and control the droplets and their contents.

The microfluidic device can combine dielectric or electric fields with droplet fission to separate ionic species during droplet breakup.

The present invention provides methods of controlling droplets using fringing fields. Effective control of uncharged droplets within microfluidic devices can require the generation of extremely strong dielectric field gradients. The fringe fields from the edges of a parallel plate capacitor can provide an excellent topology to form these gradients. The microfluidic device according to the present invention can include placing a fluidic channel between two parallel electrodes, which can result in a steep electric field gradient at the entrance to the electrodes due to edge effects at the ends of the electrode pair. Placing these pairs of electrodes at a symmetric channel split can allow precise bi-directional control of droplet within a device. Using the same principle, only with asymmetric splits, can allow single ended control of the droplet direction in the same manner. Alternatively, a variation on this geometry will allow precise control of the droplet phase by shifting.

A device of the invention can be used for the application of an electric field at a junction between two immiscible fluids. The electric field created charged droplets and large forces necessary for emulsification, while the junction stabilized droplet production even at high fields, when a Taylor cone was present. Applications of this technology include, but are not limited to, the generation of charged droplets with a narrow distribution in radius down to submicron sizes and controlled droplet coalescence by oppositely charged droplets.

The device of this embodiment can be created by patterning PDMS on a glass substrate having electrodes formed from indium tin oxide ("ITO"). A voltage difference can be applied to the electrodes to create an applied dielectric field. The device can include a two-fluid injection system where a conductive fluid can be injected into a non-conductive fluid in the presence of the electric field to generate droplets of the conductive fluid dispersed in the non-conductive fluid. Droplets can be created having diameters of less than about 1 micron to about 100 microns. These droplets can remain charged with the sign of the charge dependent on the sign of the dielectric field with respect to the direction of flow.

In the absence of an electric field, large droplets can be generated, while in the presence an electric field (E=2 V/micron), a Taylor cone can be stabilized with uniform submicron droplets being emitted from the tip. The droplets may also be discharged on a ground electrode located further downstream. Such a device can have many applications, for example, in generating well controlled nanoemulsions.

Oppositely oriented devices can also be used to generate droplets having opposite sign of charge. Using this charge, the droplets can coalesce at a precise or generally predetermined location. If there is no electric field applied, the droplets cannot coalesce. The electrostatic attraction can cause the drops to coalesce. The electric field, in some cases, can be used to control the phase between when the droplets are generated to ensure simultaneous arrival at a central location and subsequent coalescence, for example, through an auto feedback mechanism or a using an AC dither. The surface of the droplets can be deformed and electrostatic forces may overcome surface tension to produce a fluid bridge to coalesce and/or neutralize the droplets.

Interdigitation and Coalescence of Droplets

Particular design embodiments of the microfluidic device described herein allow for a more reproducible and controllable interdigitation of droplets of specific liquids followed by pair-wise coalescence of these droplets. The droplet pairs can contain liquids of different compositions and/or volumes, which would then combine to allow for a specific reaction to be investigated. The pair of droplets can come from any of the following: (i) two continuous aqueous streams and an oil stream; (ii) a continuous aqueous stream, an emulsion stream, and an oil stream, or (iii) two emulsion streams and an oil stream. FIG. 17 A-D.

The nozzle design enhances the interdigitation of droplets and further improves coalescence of droplets due to the better control of the interdigitation and smaller distance between pairs of droplets. The greater control over interdigitation allows for a perfect control over the frequency of either of the droplets. Coalescence can be accomplished by localized electric field application, as described above. Coalescence may also be accomplished by passive coalescence of droplets (i.e., without application of any external effects for the appropriate mix). Passive coalescence significantly simplifies the device operation and control, which is critical as the same procedure is repeated multiple times in a given process. To obtain the optimum operation, the spacing between droplets and coupling of the droplets can be adjusted by adjusting flow of any of the streams, viscosity of the streams, nozzle design (including orifice diameter, the channel angle, and post-orifice neck of the nozzle).

In one embodiment, passive coalescence of paired droplets can be achieved by passing the droplets through a narrowing of a channel (or a neck-down or a pinch). FIG. 18A-D. In such an embodiment, droplets passing through the pinch are touching while being elongated as they are passing through the channel. Due to the elongation and redistribution of surface activities at the elongated ends, the droplet pair coalesces spontaneously and passively.

Detection Module

A "detection module" is a location within the device, typically within the main channel where molecules, cells, small molecules or particles are to be detected, identified, measured or interrogated on the basis of at least one predetermined characteristic. The molecules, cells, small molecules or particles can be examined one at a time, and the characteristic is detected or measured optically, for example, by testing for the presence or amount of a reporter. For example, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at the sorting module.

A detection module is within, communicating or coincident with a portion of the main channel at or downstream of the inlet module and, in sorting embodiments, at, proximate to, or upstream of, the sorting module or branch point. Precise boundaries for the detection module are not required, but are preferred. The sorting module may be located immediately downstream of the detection module or it may be separated by a suitable distance consistent with the size of the molecules, the channel dimensions and the detection system. It will be appreciated that the channels may have any suitable shape or cross-section (for example, tubular or grooved), and can be arranged in any suitable manner so long as flow can be directed from inlet to outlet and from one channel into another.

The detection module can have features to detect the droplets, including but not limited to, integrated metal alloy components and/or features patterned in an electrically conductive layer, to broadcast a signal around a droplet and pick up an electrical signal in proximity to the droplet.

As each droplet passes into the detection module, it is examined for a predetermined characteristic (i.e., using the detector) and a corresponding signal is produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of a molecule, or the potency or amount of an enzyme expressed by a cell, or a positive or negative reaction such as binding or hybridization of one molecule to another, or a chemical reaction of a substrate catalyzed by an enzyme. In response to the signal, data can be collected and/or a control system in the sorting module, if present, can be activated to divert a droplet into one branch channel or another for delivery to the collection module or waste module. Thus, in sorting embodiments, molecules or cells within a droplet at a sorting module can be sorted into an appropriate branch channel according to a signal produced by the corresponding examination at a detection module. The detection can be optical detection of molecular, cellular or other characteristics, for example directly or by use of a reporter associated with a characteristic chosen for sorting. However, other detection techniques can also be employed.

The device can be used to generate droplets whose composition may vary from one to the next due to any number of reasons (chemical reaction, sample preparation, etc). Within the same device, the droplets are passed through a measurement volume in which the contents are interrogated using various means (optical or electrical). The result of the measurement is used to decide which flow path the droplets should take. The means of changing the flow path can be accomplished through mechanical, electrical, optical, or some other technique as described herein.

The device can provide an accurate means of precisely aligning optical waveguides and their associated optical elements (lenses, prisms, mirrors, interconnects, etc.) to the fluidic channels contained within the microfluidic device. Such waveguides can be used to provide well defined optical access to the fluidic channels to permit optical scattering, absorption, fluorescence, or any other optical measurement technique.

Channels within the device are typically made using semiconductor lithographic processes. In order to create the waveguides, a separate series of channels and useful shapes (lenses, mirrors, etc) can be created either simultaneously (i.e. in the same processing step) or in successive steps. The reusable master created in this way can then used to fabricate the waveguide components and fluid channels without the need for special fixturing or careful alignment in subsequent steps. The extra channels or shapes can then filled with a high index of refraction liquid (for waveguides) or reflective material (for mirrors) through injection into the channel or void. The liquid can either remain as a fluid or be allowed to solidify. UV cure epoxies used by the telecommunications industry are excellent choices for the waveguide materials. Possible waveguide geometry can include a focusing lens and a back-reflecting mirror.

The device of the present invention also comprises the use of beads and methods for analyzing and sorting beads (i.e, bead reader device). The device can read and either sort or not sort droplets containing one or more of a set of two or more beads. Each bead can be differentiated from each other bead within a set. Beads can be separated by several tags including, but not limited to, quantum dyes, fluorescent dyes, ratios of fluorescent dyes, radioactivity, radio-tags, etc. For example, a set of beads containing a ratio of two dyes in discrete amounts with an apparatus for detecting and differentiating beads containing one discrete ratio from the other beads in this set having a different ratio of the two dyes. The microfluidic device can include a paramagnetic beads. The paramagnetic beads can introduce and remove chemical components from droplets using droplet coalescence and breakup events. The paramagnetic beads can also be used for sorting droplets.

The present invention provides methods of screening molecular libraries on beads through limited-dilusion-loading and then chemical or optical release inside of droplets. Provided are methods for chemical synthesis on a bead and releasing said chemical attached to the bead using a releasing means (chemical, UV light, heat, etc) within a droplet, and then combining a second droplet to the first droplet for further manipulation. For example, tea-bag synthesis of chemicals on a bead simultaneously with a means for identifying said bead (using, for example, a mass spec tag). Using the resulting mixed-chemistry beads in a droplet within a fluid flow, and exposing the beads to UV light to release the chemical synthesized from the bead into the droplet environment. Combining the droplet containing the released chemical with a droplet containing a cell, and performing a cell-based assay. Sorting droplets having the desired characteristics (for example, turn on of a reporter gene), and then analyzing the sorted beads using mass spectroscopy.

The device of the present invention can comprise column separation prior to bead sorting. A device containing a channel loaded with a separating means for chromatographically sorting the sample prior to droplet formation. Such separating means could include size, charge, hydrophobicity, atomic mass, etc. The separating can be done isocratic or by use of a means for generating a gradient chemically, (for example using salt or hydrophobicity), electrically, by pressure, or etc. For example, a channel is preloaded with Sepharose size exclusion media. A sample is loaded at one end, and the droplets are formed at an opposing end. The sample separates by size prior to becoming incorporated within a droplet.

The detector can be any device or method for interrogating a molecule, a cell or particle as it passes through the detection module. Typically, molecules, cells or particles (or droplets containing molecules, cells or particles) are to be analyzed or sorted according to a predetermined characteristic that is directly or indirectly detectable, and the detector is selected or adapted to detect that characteristic. A preferred detector is an optical detector, such as a microscope, which may be coupled with a computer and/or other image processing or enhancement devices to process images or information produced by the microscope using known techniques. For example, molecules can be analyzed and/or sorted by size or molecular weight. Enzymes can be analyzed and/or sorted by the extent to which they catalyze chemical reaction of a substrate (conversely, substrate can be analyzed and/or sorted by the level of chemical reactivity catalyzed by an enzyme). Cells can be sorted according to whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for analyzing and/or sorting molecules or cells, i.e. detecting molecules or cells to be collected.

The molecules or cells or particles (or droplets containing them) are analyzed and/or separated based on the intensity of a signal from an optically-detectable reporter bound to or associated with them as they pass through a detection module in the device. Molecules or cells or particles having an amount or level of the reporter at a selected threshold or within a selected range are diverted into a predetermined outlet or branch channel of the device. The reporter signal may be collected by a microscope and measured by a photo multiplier tube (PMT). A computer digitizes the PMT signal and controls the flow via valve action or electro-osmotic potentials. Alternatively, the signal can be recorded or quantified as a measure of the reporter and/or its corresponding characteristic or marker, e.g., for the purpose of evaluation and without necessarily proceeding to sort the molecules or cells.

The chip can be mounted on an inverted optical microscope. Fluorescence produced by a reporter is excited using a laser beam focused on molecules (e.g., DNA, protein, enzyme or substrate) or cells passing through a detection region. Fluorescent reporters can include, but are not limited to, rhodamine, fluorescein, Texas red, Cy 3, Cy 5, pliycobiliprotein (e.g., phycoerythrin), green fluorescent protein (GFP), YOYO-I and PicoGreen. In molecular fingerprinting applications, the reporter labels can be fiuorescently labeled single nucleotides, such as fluorescein-dNTP, rhodamine-dNTP, Cy3-dNTP, etc.; where dNTP represents dATP, dTTP, dUTP or dCTP. The reporter can also be chemically-modified single nucleotides, such as biotin-dNTP. The reporter can be fluorescently or chemically labeled amino acids or antibodies (which bind to a particular antigen, or fragment thereof, when expressed or displayed by a cell or virus).

The device can analyze and/or sort cells based on the level of expression of selected cell markers, such as cell surface markers, which have a detectable reporter bound thereto, in a manner similar to that currently employed using fluorescence-activated cell sorting (SACS) machines. Proteins or other characteristics within a cell, and which do not necessarily appear on the cell surface, can also be identified and used as a basis for sorting. The device can also determine the size or molecular weight of molecules such as polynucleotides or polypeptides (including enzymes and other proteins) or fragments thereof passing through the detection module. Alternatively, the device can determine the presence or degree of some other characteristic indicated by a reporter. If desired, the cells, particles or molecules can be sorted based on this analysis. The sorted cells, particles or molecules can be collected from the outlet channels in collection modules (or discarded in wasted modules) and used as needed. The collected cells, particles or molecules can be removed from the device or reintroduced to the device for additional coalescence, analysis and sorting.

To detect a reporter or determine whether a molecule, cell or particle has a desired characteristic, the detection module may include an apparatus for stimulating a reporter for that characteristic to emit measurable light energy, e.g., a light source such as a laser, laser diode, light emitting diode (LED), high-intensity lamp, (e.g., mercury lamp), and the like. Where a lamp is used, the channels are preferably shielded from light in all regions except the detection module. Where a laser is used, the laser can be set to scan across a set of detection modules from different analysis units. In addition, laser diodes or LED's may be microfabricated into the same chip that contains the analysis units. Alternatively, laser diodes or LED's may be incorporated into a second chip (i.e., a laser diode chip) that is placed adjacent to the microfabricated analysis or sorter chip such that the laser light from the diodes shines on the detection module(s).

An integrated semiconductor laser and/or an integrated photodiode detector can be included on the silicon wafer in the vicinity of the detection module. This design provides the advantages of compactness and a shorter optical path for exciting and/or emitted radiation, thus minimizing distortion and losses.

The present invention provides methods of droplet detection using electrical signal broadcasting. The device of the present invention can comprise features, such as integrated metal alloy components and/or features patterned in an electrically conductive layer, for detecting droplets by broadcasting a signal around a droplet and picking up an electrical signal in proximity to the droplet.

The present invention provides self-aligning optical waveguides and optical elements for detection and control of droplets. The device of the present invention can comprise an accurate means of precisely aligning optical waveguides and their associated optical elements (lenses, prisms, mirrors, interconnects, etc.) to the fluidic channels contained within the device. Such waveguides can be used to provide well defined optical access to the fluidic channels to permit optical scattering, absorption, fluorescence, or any other optical measurement technique.

Fluidic channels within a microfluidic device are typically made using semiconductor lithographic processes. In order to create the waveguides, a separate series of channels and useful shapes (lenses, mirrors, etc) can be created either simultaneously (i.e. in the same processing step) or in successive steps. The reusable master created in this way can then used to fabricate the waveguide components and fluid channels without the need for special fixturing or careful alignment in subsequent steps. The extra channels or shapes can then filled with a high index of refraction liquid (for waveguides) or reflective material (for mirrors) through injection into the channel or void. The liquid can either remain as a fluid or be allowed to solidify. UV cure epoxies used by the telecommunications industry are excellent choices for the waveguide materials. Possible waveguide geometries can include a focusing lens and a back-reflecting mirror.

The dimensions of the detection module are influenced by the nature of the sample under study and, in particular, by the size of the droplets, beads, particles, molecules or cells (including virions) under study. For example, mammalian cells can have a diameter of about 1 to 50 microns, more typically 10 to 30 microns, although some mammalian cells (e.g., fat cells) can be larger than 120 microns. Plant cells are generally 10 to 100 microns. However, other molecules or particles can be smaller with a diameter from about 20 nm to about 500 nm.

Detection modules used for detecting molecules and cells have a cross-sectional area large enough to allow a desired molecule, cells, bead, or particles to pass through without being substantially slowed down relative to the flow carrying it.

In another embodiment, the droplet content detection can be achieved by simultaneous detection of contents of multiple droplets in parallel using spectroscopic fluorescence imaging with sensitivity as high as single-molecule limit. In this embodiment, one can spatially distribute droplets containing fluorescent entities such as Fluorophore biological markers and/or quantum dots in a two-dimensional sheet in a microscopic field-of-view. The filed-of-view of those droplets can then be illuminated by a fluorescence excitation source and the resulting fluorescence can be spectroscopically imaged. Therefore, for a given fluorescence detection sensitivity, the throughput of fluorescence detection compared to a single-drop fluorescence detection method can be increased by a factor of a/b for a given sensitivity, where a is the number of droplets that can be imaged within a given field-of-view, and b is the ratio of the fluorescence sensitivity of a single-drop fluorescence detector compared to that of the multiple drop fluorescence detector. Furthermore, unlike the prior art single-drop fluorescent detection method where the drops are flowed through a detection volume so that their residence time in the detection volume, and hence the signal integration time and sensitivity, is limited, the residence time of the droplet in the field-of-view can be unlimited, thereby allowing sensitivity as high as the single-molecule limit.

Sorting Module

The device of the present invention can further include one or more sorting modules. A "sorting module" is a junction of a channel where the flow of molecules, cells, small molecules or particles can change direction to enter one or more other channels, e.g., a branch channel for delivery to an outlet module (i.e., collection or waste module), depending on a signal received in connection with an examination in the detection module. Typically, a sorting module is monitored and/or under the control of a detection module, and therefore a sorting module may "correspond" to such detection module. The sorting region is in communication with and is influenced by one or more sorting apparatuses. A sorting apparatus comprises techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A "branch channel" is a channel which is in communication with a sorting region and a main channel. Typically, a branch channel receives molecules, cells, small molecules or particles depending on the molecule, cells, small molecules or particles characteristic of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

The device of the present invention can further include one or more outlet modules. An "outlet module" is an area of a microfabricated device that collects or dispenses molecules, cells, small molecules or particles after coalescence, detection and/or sorting. The outlet module can include a collection module and/or a waste module. The collection module can be connected to a means for storing a sample. The collection module can be a well or reservoir for collecting and containing droplets detected to have a specific predetermined characteristic in the detection module. The collection module can be temperature controlled. The waste module can be connected to a means for discarding a sample. The waste module can be a well or reservoir for collecting and containing droplets detected to not have a specific predetermined characteristic in the detection module. The outlet module is downstream from a sorting module, if present, or downstream from the detection module if a sorting module is not present. The outlet module may contain branch channels or outlet channels for connection to a collection module or waste module. A device can contain more than one outlet module.

Mixing Module

Although coalescence of one or more droplets in one or more coalescence modules can be sufficient to mix the contents of the coalesced droplets (e.g., through rotating vortexes existing within the droplet), the device of the present invention can further include one or more mixing modules. A "mixing module" can comprise features for shaking or otherwise manipulate droplets so as to mix their contents. The mixing module is preferably downstream from the coalescing module and upstream from the detection module. The mixing module can include, but is not limited to, the use of metal alloy component electrodes or electrically conductive patterned electrodes to mix the contents of droplets and to reduce mixing times for fluids combined into a single droplet in the microfluidic device.

The device of the present invention can comprise features, such as, acoustic actuators, metal alloy component electrodes or electrically conductive patterned electrodes, for shaking droplets to reduce mixing times for fluids combined into a single droplet.

For acoustic manipulation, the frequency of the acoustic wave should be fine tuned so as not to cause any damage to the cells. The biological effects of acoustic mixing have been well studied (e.g., in the ink-jet industry) and many published literatures also showed that piezoelectric microfluidic device can deliver intact biological payloads such as live microorganisms and DNA. In an exemplary embodiment, the design of the acoustic resonant uses a Piezoelectric bimorph flat plate located on the side of the carved resonant in the PDMS slab. The piezoelectric driving waveform is carefully optimized to select the critical frequencies that can separate cells in fluids. There are five parameters to optimize beyond the frequency parameter. Lab electronics is used to optimize the piezoelectric driving waveform. Afterwards, a low cost circuit can be designed to generate only the optimized waveform in a preferred microfluidic device.

Delay Module

The device of the present invention can further include one or more delay modules. The "delay module" can be a delay line. The operation of a microfluidics device where a reaction within a droplet is allowed to occur for a non-trivial length of time requires a delay line to increase the residence time within the device. For reactions demanding extensive residence time, longer or larger delay lines are required. Accordingly, the invention provides methods to increase residence times within microfluidic devices.

The delay module is in fluid communication with the main channel. The delay module can be located downstream of the coalescence module and upstream of the detection module. The delay module can be a serpentine channel or a buoyant hourglass. The delay module can further comprise heating and cooling regions. The heating and cooling regions can be used for performing on-chip, flow-through PCR with the devices described herein.

The channel dimensions and configurations can be designed to accommodate the required residence time with minimum pressure drops across the device. For example, to accommodate very long delay lines within the microfluidic device, the device can comprise a multilayered PDMS slab which is composed of several patterned PDMS slabs.

The channel dimensions can also be designed so as to allow for required flow, residence time and pressure drop. Some channels may be required to be very large in width and height. In order to avoid collapse of the channels, the device includes support posts within the channel design. In order to reduce dead volume behind posts and further improve droplet stability, the support posts are designed to optimize a streamlined flow within the channel. These designs can include curved features as opposed to sharp edges.

To allow for longer period of device operation, delay lines can also be extended to the outside of the chip. The off-chip delay lines can be tubes within micron-sized internal diameter.

In order to allow more efficient use of available space and faster operation, in methods where droplets are charged, after charging, asymmetric splitting of oil and drops can be accommodated by siphoning off oil from channels after droplets are charged. The delay lines can be in the form of a tower (i.e., a structure which is vertical with respect to the ambient gravitational field) as to allow buoyant forces to assist controlled droplet transport. Known delay lines involve transporting droplets by emulsifying them in a carrier fluid flowing in a channel and/or tube. Because the velocity profile of the carrier fluid through the cross-section of the channel and/or tube is not uniform, the velocity distribution of the droplets will not be narrow, which causes the delay time distribution of the droplets to not be narrow (i.e., some droplets will be delayed more or less than others).

The devices of the present invention can also include buoyancy-assisted microfluidic delay lines. In buoyancy-assisted microfluidic delay lines, buoyant forces act on droplets emulsified in a fluid in one or more towers. This can include allowing the tower to fill for the desired delay time, and then releasing the droplets. The tower can or cannot continue to fill and release droplets as needed. In this example, one may desire to have a cylindrical tower section that is capped by a pyramidal funnel section. The tower can effectively functions as an hourglass. Droplets that have a density less than their carrier fluid are fed into the base of the tower, buoyantly rise to the top of the tower with a substantially uniform velocity distribution, and are funneled into a functional component of the microfluidic device (such as a y-branch). Carrier fluid is exhausted at the base of the tower at the same rate as it is introduced at the apex so that the net flow of carrier fluid through the delay line is zero. The tower and funnel sections can have any cross-sectional shape, such as circular, elliptical, or polygonal. The microfluidic device can include a tower with adjustable length.

The device can also include a switching network of twenty towers to guarantee a delay time dispersion of 5% (because 1/20=0.05). The capacity of each tower is 0.05*T, where T is the delay time. The concept includes, for example: (a) upon device start-up, filling the first tower for 0.05*T, but stop-cock its exhaust, and also have the other nineteen towers closed; (b) after 0.05*T, closing the first tower and filling the second between 0.05*T and 0.10*T; (c) repeating step (b) for the remaining eighteen towers; (d) at time T, allowing the first tower to exhaust; (e) at time 1.05*T, stop-cocking the exhaust of the first tower, allowing the second tower to exhaust, and allowing the first tower to fill; (f) at time 1.10*T, stop-cocking the exhaust of the second tower, allowing the third tower to exhaust, closing the first tower, and allowing the second tower to fill; and (g) repeating step (f) ad infinitum. More than twenty towers may provide an even tighter control over the width of the delay time dispersion. This scheme may require a valve network. This network of towers can be outside the microfluidic device.

UV-Release Module

The device of the present invention can further include one or more UV-release modules. The "UV-release module" is in fluid communication with the main channel. The UV-release module is located downstream of the inlet module and upstream of the coalescence module. The UV-module can be a used in bead assays. Compounds from encapsulated beads can be cleaved in a UV-releasing module using UV light. Photolabile linkers can be broken down on demand after a single bead has been encapsulated thus releasing multiple copies of a single compound into solution. In the cell based assay disclosed herein the chemical compound assayed is desired to be in solution in order to penetrate the cell membrane. Furthermore, to ensure compartmentalization of a single compound with a cell the cleavage of the compound from the solid support can only be done after the bead has been encapsulated. Photocleavable linkers can be utilized to cleave the compounds of the bead after drop formation by passing the drop through a UV-release module (i.e., laser of the appropriate wavelength).

The present invention also provides methods for chemical synthesis on a bead and releasing said chemical attached to the bead using a releasing means (chemical, UV light, heat, etc) within a droplet, and then combining a second droplet to the first droplet for further manipulation. Preferably, the releasing means is a UV-module. For example, tea-bag synthesis of chemicals on a bead simultaneously with a means for identifying said bead (using, for example, a mass spec tag). Using the resulting mixed-chemistry beads in a droplet within a fluid flow, and exposing the beads to UV light to release the chemical synthesized from the bead into the droplet environment. Combining the droplet containing the released chemical with a droplet containing a cell, and performing a cell-based assay. Sorting droplets having the desired characteristics (for example, turn on of a reporter gene), and then analyzing the sorted beads using mass spectroscopy.

Kits

As a matter of convenience, predetermined amounts of the reagents, compound libraries, and/or emulsions described herein and employed in the present invention can be optionally provided in a kit in packaged combination to facilitate the application of the various assays and methods described herein. Such kits also typically include instructions for carrying out the subject assay, and may optionally include the fluid receptacle, e.g., the cuvette, multiwell plate, microfluidic device, etc. in which the reaction is to be carried out.

Typically, reagents included within the kit are uniquely labeled emulsions containing tissues, cells, particles, proteins, antibodies, amino acids, nucleotides, small molecules, substrates, and/or pharmaceuticals. These reagents may be provided in pre-measured container (e.g., vials or ampoules) which are co-packaged in a single box, pouch or the like that is ready for use. The container holding the reagents can be configured so as to readily attach to the fluid receptacle of the device in which the reaction is to be carried out (e.g., the inlet module of the microfluidic device as described herein). In one embodiment, the kit can include an RNAi kit. In another embodiment, the kit can include a chemical synthesis kit. It will be appreciated by persons of ordinary skill in the art that these embodiments are merely illustrative and that other kits are also within the scope of the present invention.

Definitions

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them. It will be appreciated that the same thing can typically be described in more than one way. Consequently, alternative language and synonyms may be used for any one or more of the terms discussed herein. Synonyms for certain terms are provided. However, a recital of one or more synonyms does not exclude the use of other synonyms, nor is any special significance to be placed upon whether or not a term is elaborated or discussed herein. AU publications, patent applications, patents, and other references mentioned herein are incorporated by reference. In the case of conflict, the present specification, including definitions, will control. In addition, the materials, methods, and examples are illustrative only and are not intended to be limiting.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

As used herein, "about" or "approximately" shall generally mean within 20 percent, preferably within 10 percent, and more preferably within 5 percent of a given value or range.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded KNA and DNA, and backbone modifications thereof, for example, methylphosphonate linkages.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "interdigitation" as used herein means pairing of droplets from separate aqueous streams, or from two separate inlet nozzles, for eventual coalescence.

The term "dielectrophoretic force gradient'*means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" (one or more peptides) is a chain of chemical building blocks called amino acids that are linked together by chemical bonds called peptide bonds. A "protein" is a polypeptide produced by a living organism. A protein or polypeptide may be "native" or "wild-type", meaning that it occurs in nature; or it may be a "mutant", "variant" or "modified", meaning that it has been made, altered, derived, or is in some way different or changed from a native protein, or from another mutant.

An "enzyme" is a polypeptide molecule, usually a protein produced by a living organism, that catalyzes chemical reactions of other substances. The enzyme is not itself altered or destroyed upon completion of the reaction, and can therefore be used repeatedly to catalyze reactions. A "substrate" refers to any substance upon which an enzyme acts.

As used herein, "particles" means any substance that may be encapsulated within a droplet for analysis, reaction, sorting, or any operation according to the invention. Particles are not only objects such as microscopic beads (e.g., chromatographic and fluorescent beads), latex, glass, silica or paramagnetic beads, but also includes other encapsulating porous and/or biomaterials such as liposomes, vesicles and other emulsions. Beads ranging in size from 0.1 micron to 1 mm can be used in the devices and methods of the invention and are therefore encompassed with the term "particle" as used herein. The term particle also encompasses biological cells, as well as beads and other microscopic objects of similar size (e.g., from about 0.1 to 120 microns, and typically from about 1 to 50 microns) or smaller (e.g., from about 0.1 to 150 nm). The devices and methods of the invention are also directed to sorting and/or analyzing molecules of any kind, including polynucleotides, polypeptides and proteins (including enzymes) and their substrates and small molecules (organic or inorganic). Thus, the term particle further encompasses these materials.

The particles (including, e.g., cells and molecules) are sorted and/or analyzed by encapsulating the particles into individual droplets (e.g., droplets of aqueous solution in oil), and these droplets are then sorted, combined and/or analyzed in a microfabricated device. Accordingly, the term "droplet" generally includes anything that is or can be contained within a droplet.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art.

As used herein, "cell" means any cell or cells, as well as viruses or any other particles having a microscopic size, e.g. a size that is similar to or smaller than that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) or smaller (e.g., about 0.1 to 150 nm) any material having a size similar to or smaller than a biological cell can be characterized and sorted using the microfabricated device of the invention. Thus, the term cell shall further include microscopic beads (such as chromatographic and fluorescent beads), liposomes, emulsions, or any other encapsulating biomaterials and porous materials. Non-limiting examples include latex, glass, orparamagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). The term cell further encompasses "virions", whether or not virions are expressly mentioned.

A "virion", "virus particle" is the complete particle of a virus. Viruses typically comprise a nucleic acid core (comprising DNA or RNA) and, in certain viruses, a protein coat or "capsid". Certain viruses may have an outer protein covering called an "envelope". A virion may be either living (i.e., "viable") or dead (i.e., "non-viable"). A living or "viable" virus is one capable of infecting a living cell. Viruses are generally smaller than biological cells and typically range in size from about 20-25 nm diameter or less (parvoviridae, picornoviridae) to approximately 200-450 nm (poxviridae). However, some filamentous viruses may reach lengths of 2000 nm (closterviruses) and are therefore larger than some bacterial cells. Since the microfabricated device of the invention is particularly suited for sorting materials having a size similar to a virus (i.e., about 0.1 to 150 nm), any material having a size similar to a virion can be characterized and sorted using the microfabricated device of the invention. Non-limiting examples include latex, glass or paramagnetic beads; vesicles such as emulsions and liposomes; and other porous materials such as silica beads. Beads ranging in size from 0.1 to 150 nm can also be used, for example, in sorting a library of compounds produced by combinatorial chemistry. As used herein, a virion may be charged or uncharged. For example, charged beads may be used to facilitate flow or detection, or as a reporter. Biological viruses, whether viable or non-viable, may be charged, for example, by using a surfactant, such as SDS.

A "reporter" is any molecule, or a portion thereof, that is detectable, or measurable, for example, by optical detection. In addition, the reporter associates with a molecule, cell or virion or with a particular marker or characteristic of the molecule, cell or virion, or is itself detectable to permit identification of the molecule, cell or virion's, or the presence or absence of a characteristic of the molecule, cell or virion. In the case of molecules such as polynucleotides such characteristics include size, molecular weight, the presence or absence of particular constituents or moieties (such as particular nucleotide sequences or restrictions sites). In the case of cells, characteristics which may be marked by a reporter includes antibodies, proteins and sugar moieties, receptors, polynucleotides, and fragments thereof. The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. In one embodiment, the reporter is a protein that is optically detectable without a device, e.g. a laser, to stimulate the reporter, such as horseradish peroxidase (HRP). A protein reporter can be expressed in the cell that is to be detected, and such expression may be indicative of the presence of the protein or it can indicate the presence of another protein that may or may not be coexpressed with the reporter. A reporter may also include any substance on or in a cell that causes a detectable reaction, for example by acting as a starting material, reactant or a catalyst for a reaction which produces a detectable product. Cells may be sorted, for example, based on the presence of the substance, or on the ability of the cell to produce the detectable product when the reporter substance is provided.

A "marker" is a characteristic of a molecule, cell or virion that is detectable or is made detectable by a reporter, or which may be coexpressed with a reporter. For molecules, a marker can be particular constituents or moieties, such as restrictions sites or particular nucleic acid sequences in the case of polynucleotides. For cells and virions, characteristics may include a protein, including enzyme, receptor and ligand proteins, saccharides, polynucleotides, and combinations thereof, or any biological material associated with a cell or virion. The product of an enzymatic reaction may also be used as a marker. The marker may be directly or indirectly associated with the reporter or can itself be a reporter. Thus, a marker is generally a distinguishing feature of a molecule, cell or virion, and a reporter is generally an agent which directly or indirectly identifies or permits measurement of a marker. These terms may, however, be used interchangeably.

The invention is further described below, by way of the following examples. The examples include descriptions of particular, exemplary embodiments of the devices and methods of the present invention, including particular embodiments of channel architectures, valves, switching and flow control devices and methods which may be implemented as part of the devices and methods of the invention. The examples are provided, for illustrative purposes only and are not limiting of the above-described invention in any way. For example, many of these specific embodiments are described and discussed primarily in terms of detecting and sorting cells suspended directly in the fluid that flows through a main channel of the device. Nevertheless, it will be appreciated by persons of ordinary skill in the art that these preferred embodiments are merely illustrative and that the invention may be practiced in a variety of embodiments that share the same inventive concept. In particular, the devices and methods described in this example (including the channel architectures, valves, switching and flow control devices and methods) may be readily adapted to a multi-phased device so that droplets which contain, e.g., molecules, cells or virions may be analyzed and/or sorted as desired by a user.

EXAMPLES

Example 1

The device of the present invention can be used for Live/Dead Cell Based Assays. In one example, the assay uses two fluorophores; one is permeable across cell membranes, and a second dye binds DNA and can enter the cell only if the membrane is compromised. Similar Live/Dead assays exist for bacteria and yeast. Tagged chemical libraries and pliotocleavable linkers can be used in such assays. Combinatorial one-bead-one-compound libraries obtained through split-bead synthesis require a tag which describes their synthetic history in order to identify the compound reliably. Several encoding technologies for microcarriers such as beads, rods and crowns have been developed over the last decade to address this need. A simple and effective method relies on spectrometric chemical tags which are generated in parallel to the chemical entity of interested utilizing orthogonal chemistry. Alternatives include the use of nucleic acids such as DNA, followed by the use of the polymerase chain reaction (PCR) to decode the encoded beads.

In the cell based assay disclosed herein the chemical compound assayed is desired to be in solution in order to penetrate the cell membrane. Furthermore, to ensure compartmentalization of a single compound with a cell the cleavage of the compound from the solid support can only be done after the bead has been encapsulated. Photocleavable linkers can be utilized to cleave the compounds of the bead after drop formation by passing the drop through a UV-release module (i.e., laser of the appropriate wavelength).

To evaluate the effect of individual components contained in the molecular library, a two color fluorescence detection for standard cytotoxicity assays can be used [available from Invitrogen (Carlsbad, Calif.) or Cell Technology]. While any cells can be used, for illustrative purposes, the Invitrogen LIVE/DEAD Viability/Cytotoxicity Kit # L3224 for animal cells are used here. This kit contains two probes that measure two recognized parameters of cell viability: intracellular esterase activity and plasma membrane integrity. Live cells are identified by the presence of intracellular esterase activity, detected by the enzymatic conversion of the almost nonfluorescent cell-permeant calcein AM to the extremely fluorescent calcein. The calcein is retained within live cells, producing an intense uniform green fluorescence. EtliD-1 enters cells with damaged membranes and undergoes a 40-fold enhancement of fluorescence upon binding to nucleic acids, thereby producing a bright red fluorescence in dead cells. EthD-1 is excluded by the intact plasma membrane of live cells. The determination of cell viability depends on these physical and biochemical properties of cells. Background fluorescence levels are inherently low with this assay technique because the dyes are essentially non-fluorescent before interacting with cells.

Figure 2:
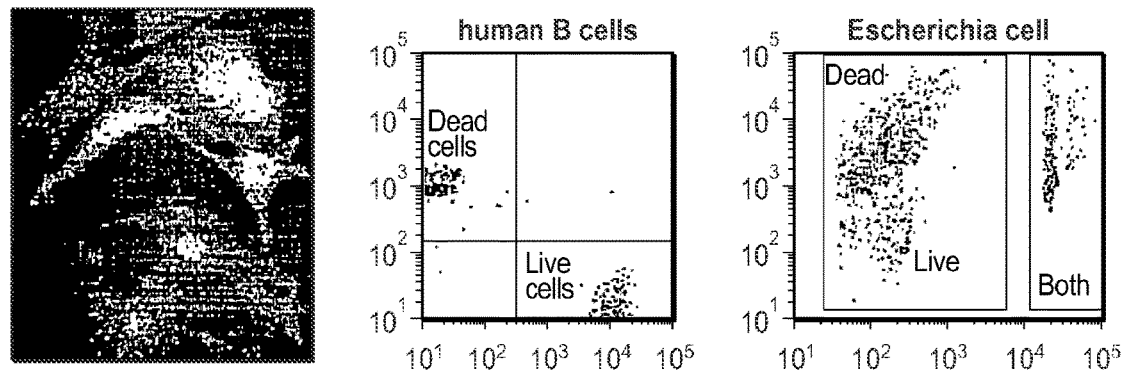
FIG. 2 is a photograph and accompanying graphs showing the flow cytometric-cell-based assay for human and bacterial cells.
Figure 3:
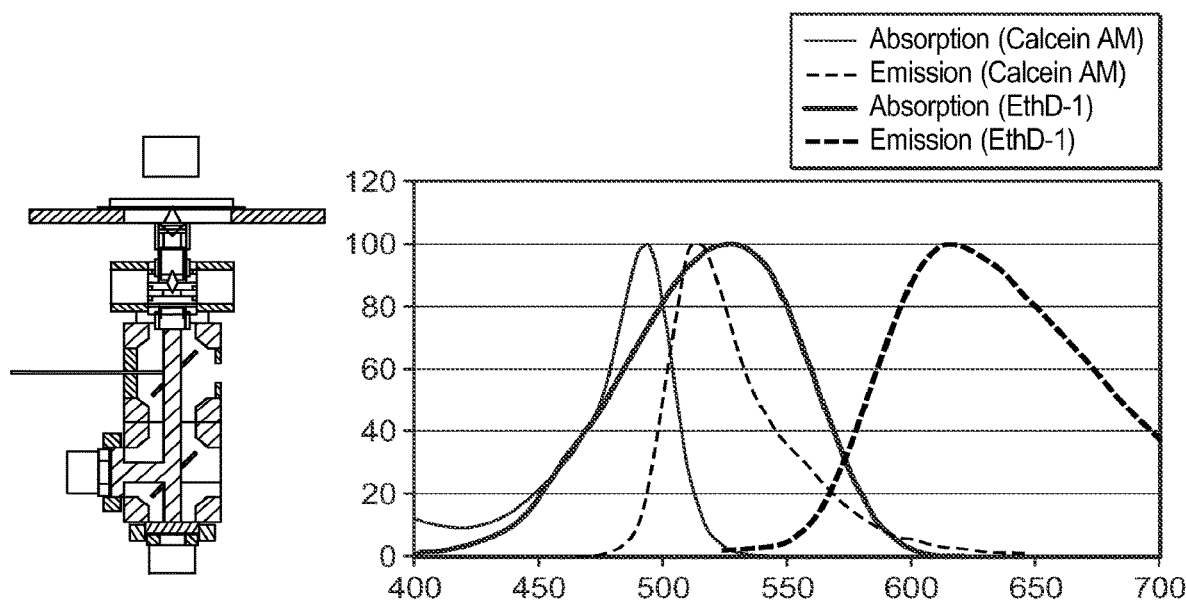
FIG. 3 is a schematic and graph showing simultaneous two color fluorescence detection.

The spectral absorption and emission characteristics for both the calcein and EthD-1 are presented in FIG. 3, while FIG. 2 plots results presented by Molecular probes when a 50/50 mix of live and dead cells are run through a flow cytometer. The absorption characteristics of both dyes makes it possible to excite fluorescence using the existing 488 nm excitation source. FIG. 2, left panel, shows a mixture of live and ethanol-killed bovine pulmonary artery epithelial cells stained with the reagents in Molecular Probes Live/Dead Cell Viability/Cytotoxicity Assay Kit (L3224). Live cells fluoresce bright green, whereas dead cells with compromised membranes fluoresce red-orange. (Molecular Probes). The middle panel shows a viability assay using Molecular Probes' LIVE/DEAD Viability/Cytotoxicity Kit on a flow cytometer. A 1:1 mixture of live and ethanol-fixed human B cells was stained with calcein AM and ethidium homodimer-1, flow cytometric analysis was carried out with excitation at 488 nm. The right panel shows analysis of bacterial cultures using the Live/Dead BacLight Bacterial Viability and Counting Kit available from www.molecular probes.com. As shown in FIG. 3, left panel, the present invention further provides a fluorescence detection system comprising a fluorescence detection stand capable of measuring green fluorophores within microfluidic channels while simultaneously permitting visual monitoring via a high speed video microscope. The optical components of this system are commercially available. The modular layout of this system permits straightforward modification of the excitation and detection wavelengths. This modularity also makes it possible to upgrade the system to multi-wavelength excitation, multi wavelength detection, and detection of orthogonal polarization states. Currently, the 488 nm transition of a multiline Argon-Ion Laser is used as the excitation source for Fluorescein (FITC). The laser provides between 3 and 20 milliwatts of power and is focused to a spot approximately 17 microns in diameter (full width half maximum, FWHM). When the stand is configured to use a photomultiplier tube, it is able to detect less than 10,000 FITC molecules at a 10 IcHz droplet rate. The sensitivity of this system is limited by fluorescence interference generated by the microfluidic device itself. The right panel of FIG. 3 shows excitation and emission spectra for calcein AM and EthD-1 dyes. Normal cytometry protocol excites both at 488 nm. FIG. 3 indicated the changes required to convert the single flurophore station to a two color fluorescence station. The calcein fluorescence can be collected using filters designed for fluorescein detection, while the EthD-1 can be monitored using filters designed for propidium iodide or Texas Red.

Using water droplets doped with fluorscien and propidium iodide over a range of concentrations from $1\times10^{-3}$ M to $1\times10^{-8}$ M, both dyes have similar absorption and fluorescence properties to calcein and Ethd-1. In seventeen micron droplets, this corresponds to a range of $1.5\times10^{9}$ to $1.5\times10^{4}$ molecules within the measurement volume. Once the baseline performance has been verified, tests can begin on droplets containing live cells, dead cells, and mixtures of the two. This establishes selectivity and detection limits on the two types of cells.

The dyes selected have been used extensively in flow cytometry and are commonly used in most cell-based assays. They are designed not to overlap significantly with each other and can be evaluated both independently and together to assess the cross-talk. The status of (potentially) many cells within one drop can thus be determined. The use of inexpensive optics on our instrument will be more than compensated for by the theoretical increase of dye molecules in the nanoreactor. Optics with higher efficiencies can be used.

Compounds from encapsulated beads can be cleaved in a UV-releasing module using UV light. Photolabile linkers can be broken down on demand after a single bead has been encapsulated thus releasing multiple copies of a single compound into solution.

Synthetic chemistry relies on the differential activity of chemical groups in order to control bond breaking and forming processes. Photolabile protecting groups form a fourth orthogonal type of functionality which survive reaction conditions capable of cleaving protective groups of the other types. Several of these photolabile protecting groups have been used to link organic molecules to solid support and their use as linkers has been reviewed. This allows the synthesis of solid supported molecules with the option of releasing the final product by irradiation with the appropriate wavelength. The repertoire of chemical groups for which photocleavalbe protecting groups have been devised is extensive, which allows the synthesis of diverse combinatorial libraries.

In lieu of the high sample rate a triazene-based photolabile linker, which is cleaved by irradiation with a 355 nm 3w Nd-YAG laser, can be used. This linker is stable under a wide range of reaction conditions with the exception of strong acids lending itself to solid supported split-bead synthesis.

If the residence time of the bead inside the UV laser is insufficient to cleave all of the compound off the substrate bead, the residence time can be increased by slowing down the flow of the bead containing drops by widening the channel. Alternatively the intensity of laser beam can be increased to ensure complete cleavage.

As previously discussed, long incubation times are desirable for cytotoxicity studies, but cannot be easily achieved in known micofulidic channel layouts. Accordingly, one embodiment of the device used in the live/dead cell-based assay disclosed herein uses a passive means to achieve uniform droplet residency times exceeding one hour in a delay line module located directly before the sorting module. It is possible to achieve a delay time of one hour between droplet generation and detection without stopping droplet generation.

In one example, a "buoyancy hourglass" delay line can be used, wherein, similar to sands in an hourglass which depend on gravity, the droplets will rise from a large reservoir to an exhaust port due to their density mismatch with the carrier oil. Microfluidic modules (e.g., inlet module, UV-releasing module, coalescence module, and mixing module) which are utilized before the delay module can be patterned at the bottom of the stack, and microfluidic modules which are utilized after the delay module (e.g., detection module and sorting module) can be patterned at the top of the stack. Upon start-up, the hourglass will be stop-cocked to allow droplets to fill until the desired delay time is reached and then droplet will be removed from the device at the same rate that they enter, thereby ensuring essentially the same residency time for all droplets. Spontaneous droplet coalescence in the hourglass can be prevented by using one or more surfactants to stabilize the droplets.

The shape and timing of electric field gradients through the use of computer modeling can be optimized by tailoring the geometry of the electrodes and the fluid channels and the synchronization of the applied voltages to the droplets.

The FEMLAB (COMSOL, Inc.) partial differential equation solver software can be used to model the combination of fluid dynamics and electrostatics. The model can include "still-frame captures" of the trajectory of droplets through bifurcations, and can optimize the electrode geometry, the fluid channel geometry, and the distribution of applied voltages as a function of the incremental droplet trajectory. Further, a high-speed digital camera and driving electronics can be used to acquire "still-frame captures" of the actual droplet trajectories and comparing those captures to those produced by the model. The model and the electrode and fluid channel geometries can be iterarively optimized using inexpensive rapid prototyping capability (24 hours from design to test-results). Finally, the electric field gradients can be satisfactorily optimized when bidirectional sorting at rates of 1000 droplets/second or greater, without breaking the droplets and with an acceptably low error rate for the given application, is achieved. If the electromechanical relay network is not fast enough to operate with the optimized timing parameters, a solid-state relay network (e.g., using Behlke electronic relays) can be used to increase the speed of the driving electronics.

Droplets containing beads can be sorted using dielectrophoretic and electrostrictive forces based on a fluorescence probe at rates of 1000 droplets/s or greater. A fluorescence detection system and Electrical Control System can be used to trigger the optimal "pulse" (i.e., distribution of applied voltages as a function of time) to sort neutral droplets based on the fluorescence probe. Dielectrophoretic/electrostrictive sorting of droplets containing fluorescent dye can be performed, wherein the sorting is triggered by the droplet number (e.g., every nth droplet is sorted in one direction, or every nth or mth droplet is sorted in one direction, etc.). Fluorescent dye can be used to perform dielectrophoretic sorting of droplets because it is convenient and inexpensive; the trigger signal for the dielectrophoretic/electrostrictive sorting can be exactly the same as was used for electrophoretic sorting. This process is the direct logical consequence of optimizing the electric field gradients.

Additionally, dielectrophoretic/electrostrictive sorting of droplets containing fluorescent beads can be performed. This step is intermediate between droplets containing fluorescent dye and droplets containing cells and beads laden with chemical libraries. Finally, dielectrophoretic/electrostrictive sorting of droplets containing fluorescent cells can be performed. This step is intermediate between droplets containing fluorescent dye and droplets containing cells and beads laden with chemical libraries.

In the event that the solutions containing the beads or cells have dielectric properties so different than the solution containing fluorescent dye that the dielectric field gradients are not optimal, the dielectric field gradients can be optimized separately for each solution. The fluorescent dye solution can be modified to better resemble the bead or cell solutions in order to continue to take advantage of the convenience of the fluorescent dye for the development of the sorting parameters.

Droplets sorted based on a particular phenotype (for example, dead cells) will be decoded (by using a decoding scheme) to identify the compound added in that droplet.

In some embodiments, the assay can be based on a nucleic-acid based encoded bead system. Two types of beads can be used for example—one contains a cytotoxic compound and oligonucleotide tag, and a second bead contains only a different oligonucleotide tag. The two types of beads may (optionally) also be encoded by a different fluorescent tag (i.e., other than the ones being used for the cell-based assays, as an example, two different Q-dots) so that the beads can be examined under a fluorescent microscope after sorting to determine the sorting efficiency.

The sorted beads from dead-cell containing nanoreactors can then be taken, and using the polymerase chain reaction (PCR), the tags on the beads can be amplified using PCR primers. These tags can be 'hard-copied' by cloning them into a plasmid vector, transforming them into E. coli, and the tag sequence of 100 different E. coli transformants determined by DNA sequencing.

Additionally, more complex libraries using T-bag synthesis on beads, can be constructed, wherein oligonucleotide tags are specific for each round of synthesis for a monomer. The same monomer used in two different rounds can have two separate tags. As a non-limiting example, if 30 monomers in a bead-based T-bag synthesis were used for 5 rounds, 5×30, or 150 different tags will be required. The complexity of a library of 30 monomers after 5 rounds is $30^5$, or nearly 25 million compounds. The beads in a specific T-bag after each round of monomer synthesis can have a specific oligonucleotide tag ligated, using T4 DNA ligase, onto the beads. These tags, from sorted beads, can be amplified, cloned and sequenced. By knowing what tags were used in which round of synthesis, an internal check of validation of the bead that was positive in that droplet is achieved. The sequencing reaction can be eliminated by using a hybridization chip containing the 150 tags.

Example 2

The present invention provides methods for performing polymerase chain reaction in nanoreactors of the present invention as described. PCR can be performed on a drop-by-drop basis in a microfluidic device according to the present invention. A monolithic chip can be provided wherein the heating and cooling lines are built into the chip and a sorting means is provided. Advantages of performing PCR in droplets on such a chip are that the chip is disposable and the reaction can be repeated without cleaning the device between reactions. Furthermore, the chip provides a convenient way of getting all the components to perform PCR in the droplets in the right concentration. Additionally, the PCR is more efficient because the heat transfer is more efficient due to the small volume. This provides for shorter incubation/residence times. Droplets containing the nucleic acids, all PCR primers, and, if present, beads are generated one at a time at rates between 100 and 20,000 droplets per second. The droplets can then be sent through a serpentine path between heating and cooling lines to amplify the genetic material inside the droplets. Upon exiting the device the droplets may be sent for further on-chip or off-chip processing, directed into another chip, or the emulsion may be broken to release the PCR product. If present, beads may be harvested by passing' the emulsion through a filtration device, sedimentation, or centrifugation.

The width and depth of the channel can be adjusted to set the residence time at each temperature, which can be controlled to anywhere between less than a second and minutes. At a typical rate of 1000 drops per second, 1 million strands of DNA can be amplified in approximately 20 minutes on one device. A typical flow rate of 250 µL/hour would correspond to 1000 drops of 50 microns in diameter being generated every second. Flow rates and droplet sizes can be adjusted as needed by controlling the nozzle geometry.

In an example bead based application, the purpose is to amplify at most one DNA fragment in a droplet containing a single micro-bead (1 to 100 microns in diameter) and then separate and collect only the beads coated with DNA. This is achieved by starting with a dilute mixture of DNA fragments and beads in a solution containing the appropriate PCR primers. Droplets are then made in the limited dilution regime where most of the droplets are empty, but some droplets have a DNA strand in them and some droplets have beads in them. The target droplets have both a single DNA fragment and a single bead. After PCR amplification of the DNA on the surface of the beads a fluorescence activated sorting module (NanoFACS) can be added to the end of the device to separate the droplets into two populations, one containing amplified DNA and one without amplified DNA. The beads are then removed from the emulsion where the droplets all contain DNA to achieve a collection of beads where essentially all beads are coated with only one type of DNA fragment.

The quality of the collection of beads where each fragment is amplified in the presence of only one bead can be enhanced by ensuring that each droplet contains at most one bead. Droplets containing more than one bead can be removed using a fluorescence-based sorting step.

Along with PCR, nucleic acid based signal methods such as tyramide assays using an appropriate enzyme reaction, oligonucleotides decorated with two or more detecting groups, or other amplification means, for example, rolling circle amplification, ligase chain reaction, and NASBA can be used to increase the signal within a droplet.

Example 3

The device of the present invention can be used to screen chemical libraries composed of at least $10^6$ molecules against an established cell line. In this manner, positive and negative nanoreactors can be tracked and sorted using either a nucleic-acid based, or multicolored bead-based encoding scheme For example, a control library with known hits can be screened against a human cancer cell line.

Figure 4:
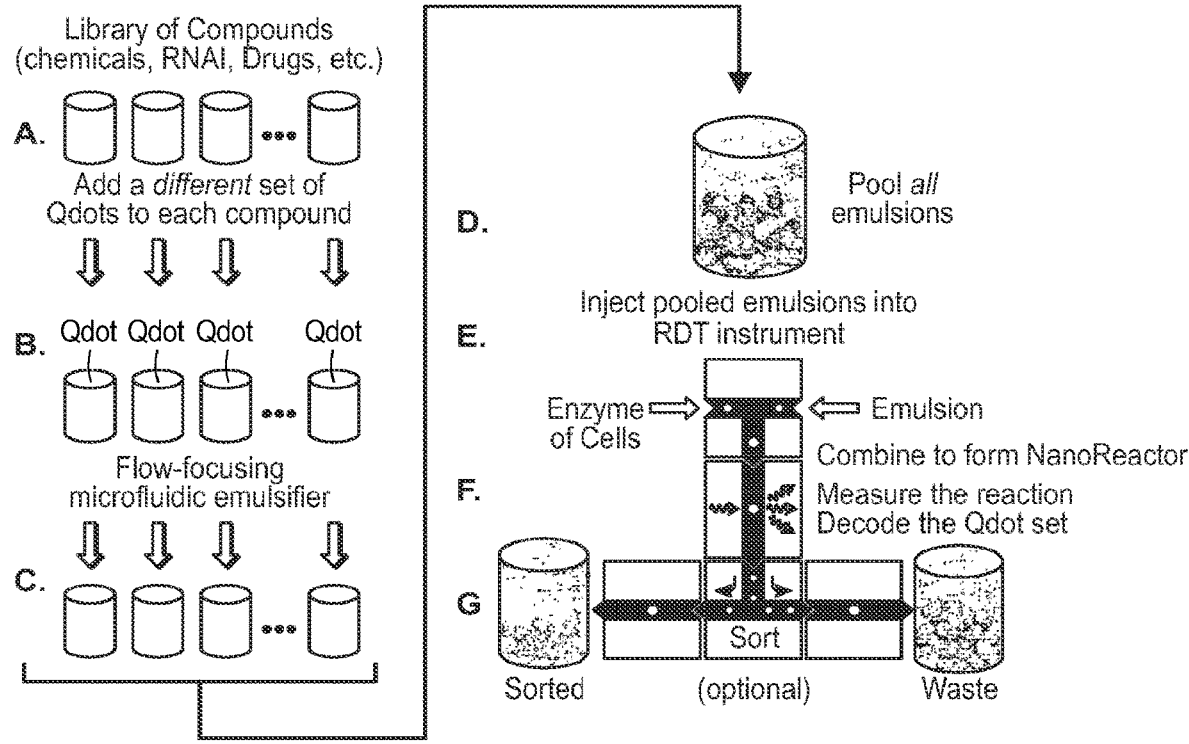
FIG. 4 is a schematic illustrating chemical library screening using a nanoreactor of the present invention.
Figure 5:
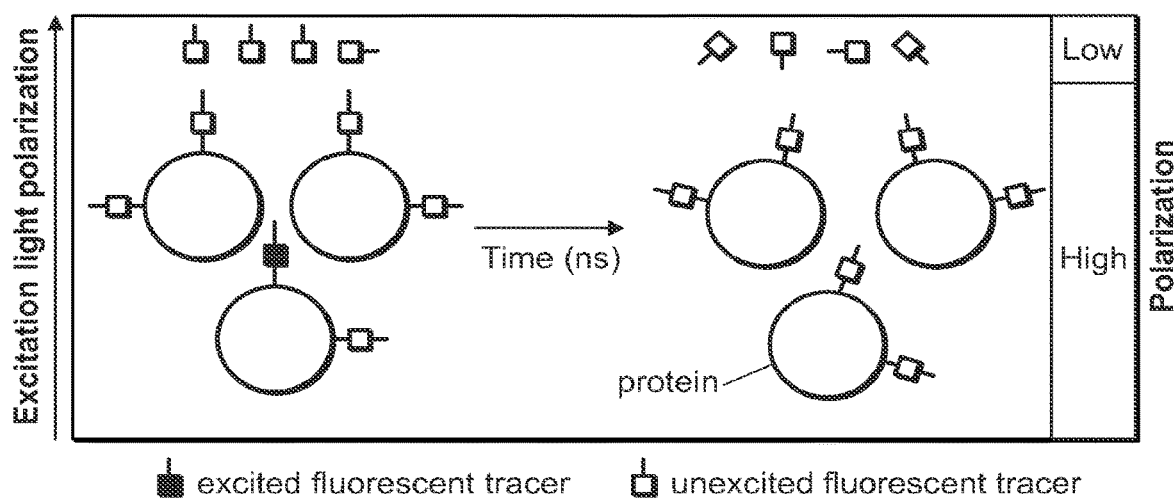
FIG. 5 is a schematic illustrating the physical basis of fluorescence polarization assays.

In one embodiment, a chemical library can be screened using a nanoreactor as described in detail herein. The power of the present invention comes from a combination of compartmentalization and electrical manipulation that enables multi-step chemical processing, including analysis and sorting, to be initiated in confinement with exquisite timing and metering precision. This multi-step processing of isolated components is essential for searching through molecular libraries for rare interactions with cells, nucleic acids, enzymes, coded microbeads, and other biomaterials. For example, a set of encoding nucleic acids, (i.e., DNA tags) can be combined into solutions of unique chemical compounds such that the DNA tags and chemicals are emulsified together. In one embodiment, the DNA tag acts as a surrogate identifier to track the associated chemical compound in droplets sorted by a nanoreator described herein. After sorting, the emulsion can be broken and the nucleic acids can be decoded (FIG. 4). As shown in FIG. 4 (Left panel), (A) An individual compound from a library of compounds will each be combined (B) with a unique, differentiatable set of q-dots. The combined mixture will each (C) be separately emulsified off-line using a flow-focusing microfluidics emulsifier to synthesize individual droplets containing both a specific compound and a unique set of q-dots. As shown in FIG. 4 (Right panel), the set of individually-emulsified encoded compounds will be (D) pooled together and injected, along with either cells or enzymes, into the RDT instrument and (E) the two droplets combined to than individual NanoReactors. Depending on the reaction being monitored, a separate combining (not shown in the figure) of these nanoreactors with droplets containing assay components may be needed. In addition, a delay loop may be placed between these combinings and the detector (F) to allow sufficient time to occur in the droplet as to allow any potential chemical/cellular/enzymatic reaction to occur. The nanoreactors are next sent past a detector to both monitor the reaction and decode the q-dots contained within it. The nanoreactors can be further sorted (G) if necessary. In designing the device to be placed on the Instrument, individual modules are strung together in a sequence of droplet operations. Operations can be used to encapsulate cells or enzyme, inject the labeled preformed compound library emulsion, coalesce pairs of droplets, mix the contents of droplets, incubate reactions over time, detect fluorescence, decode the liquid label, sort (if needed) based on the detected signal, and transport droplets to collection and waste streams. The individual modules operate independently, much like resisters and capacitors in an electrical circuit, to collectively perform complex fluid processing operations. Several methods encompassing various chemical library screening embodiments of the invention as described. In one example, a kinase enzyme assay is used as an enzyme model, three different quantum dots (q-dots) for the liquid label, and a set of 96 different chemical compounds (in which 1-2 will be preferred kinase substrates) as the library. Fluorescence polarization is preferred since the argument can be made that it can be adapted to many different types of assays. In one example, water-soluble q-dots that emit at 620 nm, 650 nm and 680 nm are used. These emission bands are well outside of spectral region where the target enzyme assays emit (below 580 nm), so these q-dots are an excellent choice for In another example, near-IR q-dots are used to enhance their water solubility for the purpose of expanding the non-overlapping spectral region of the target assays. Moving the q-dot readout to this "unused" wavelength band can permit virtually any fluorescence assay of interest to be adapted to the nanoreactors of the present invention without modification, tremendously expanding the application space immediately available.

The nucleic acid can be a linear molecule wherein the ends can be used as priming sites for PCR, and the middle sequence is unique to each chemical compound; it is this middle sequence that is used as the encode. The nucleic acid and chemical compound are together combined into one droplet by pre-emulsifying the nucleic acid and chemical together and then adding them to a microfluidic device as described herein, as a pre-made, compound droplet. The compound droplet can be combined with a another droplet on the instrument. This other droplet can contain an item under investigation (including for example, but not limited to, a cell or enzyme), which, when combined with the compound droplet forms an 'assay' droplet. The assay droplets having a desired detected property (for example, inhibition of enzyme activity through the use of a fluorescent substrate added to the compound microdrop) can then be sorted. The sorted assay droplets can be collected, the emulsion broken, and the nucleic acid sequence can be decoded. The decoding can be performed by emulsion PCR (as described in U.S. Application Publication No. 2005-0227264) and sequencing on a sequencing instrument. Alternatively, the decoding can be performed by cloning the PCR product into an appropriate host (for example, $E.$ $coli$), and the resultant clones subjected to DNA sequencing.

The nucleic acid can be a linear molecule having a region of uniqueness, and the decoding can be performed by cloning and subsequently transforming the DNA obtained from sorted assay droplets into an appropriate host {e.g., $E.$ $coli$). The resultant clones can then be subjected to decoding by hybridizing a PCR product containing the unique identifier to a complementary strand of nucleic acid fixed to a solid support (for example a chip, wafer, or bead).

The nucleic acid can be a plasmid having a region of uniqueness, and the decoding can be performed by transforming the DNA obtained from sorted assay droplets into an appropriate host {e.g., $E.$ $coli$). The resultant clones can then be subjected to DNA sequencing to identify the encoded sequence. The nucleic acid can be a plasmid having a region of uniqueness, and the decoding can be performed by transforming the DNA obtained from sorted assay droplets into an appropriate host (e.g., $E.$ $coli$). The resultant clones can then be subjected to decoding by hybridizing a labeled-PCR product containing the unique identifier to a complementary strand of nucleic acid fixed to a solid support (for example a chip, wafer, or bead).

The nucleic acid can be either a plasmid or linear fragment having a region of uniqueness, and the decoding can be performed by transforming the DNA obtained from sorted assay droplets into an appropriate host (e.g., $E.$ $coli$). The resultant clones can then be subjected to decoding by hybridizing a labeled-PCR product containing the unique identifier to a complementary strand of nucleic acid fixed to a solid support (for example a chip, wafer, or bead). Preferably, the bead can be encoded with dyes or Qdots, and the decoding can be performed on a microfluidic device according to the present invention, or on a Qdot or Luminex installment.

A set of unique nucleic acids can be added to a set of unique chemical entities, wherein each combined set is separately emulsified. The separately emulsified combined set can be further combined to generate an emulsified mixed solution of droplets, wherein each droplet can contain both a nucleic acid and a unique chemical entity. This combined mixed solution can be injected into a microfluidic device according to the present invention for use in various assays contemplated by one of ordinary skill in the art.

The nucleic acid containing unique identifiers can be generated by PCR of an antibiotic resistance or other selectable gene with a set of the forward and reverse PCR primers each containing a 5' nucleotide sequence common to each other, forward and downstream primers, respectively, a unique sequence 3' to the common sequence, and a region of the antibiotic or other selectable gene. Said primers can be used in a PCR reaction to generate an antibiotic resistance or other selectable gene bracketed by unique identifiers which in turn can be bracketed by either a forward or reverse common sequence. The PCR product can then be cloned into a vector having a second antibiotic resistance or other selectable gene, and the vector can be cloned into an appropriate host (e.g., E. coli), thereby selecting for antibiotic resistance and another selectable gene simultaneously.

The label can also be a solution containing a dye such as an organic dye (for example cy3, cy5, flourescein) or inorganic label such as a quantum dot. The dot can be further coated or encapsulated by hydrophobic residues. More than one dye can be added to a solution prior to emulsification and the ratio of one or more dyes can be used to decode the droplet.

Additionally, many bead-encoded assays have already been developed for microspheres that should be directly ported to the devices and systems disclosed herein. Such assays include, for example: allergy testing, disease markers (including, autoimmune, cancer and cardiac), cytokine, genotyping, gene expression, infectious disease, kinase/phosphorylated proteins, metabolic markers, tissue typing, transcription factors/nuclear receptors and others.

The present invention also provides methods of using a drop-washer for combinatorial chemistry/biology. A device of the present invention capable of exchanging constituents within a droplet through the use of fluid flow in such a way that the microdrop, while in a first immiscible fluid, is exposed to a second immiscible fluid such that constituents within the droplet that are immiscible in the first immiscible fluid are soluble in the second immiscible fluid.

For example, an aqueous droplet containing a chemical reaction produces by-products that are soluble in a lipid solvent. The chemical reaction is performed in a water-environment in a silicon-based solvent. After the chemical reaction occurs, the droplet is exposed to an organic-oil based solvent where the chemical byproducts are allowed to diffuse out of the droplet. The resulting droplet is then assayed for cell-killing activity by combining the droplet with live cells.

Similar to the preceding example, but the change in the, non-aqueous fluid flow is used to add a particular constituent from the second immiscible fluid to diffuse into the aqueous drop before the droplet is returned to the 100% first immiscible fluid flow.

Example 4

The present invention also provides methods of performing biological assays in nanoreactors using fluorescence polarization (FP). Fluorescence polarization technology has been used in basic research and commercial diagnostic assays for many decades, but has begun to be widely used in drug discovery only in the past six years. Originally, FP assays for drug discovery were developed for single-tube analytical instruments, but the technology was rapidly converted to high-throughput screening assays when commercial plate readers with equivalent sensitivity became available. These assays include such well-known pharmaceutical targets such as kinases, phosphatases, proteases, G-protein coupled receptors, and nuclear receptors.

Nuclear Receptors;

FP has been used to develop high throughput screening (HTS) assays for nuclear receptor-ligand displacement (Parker G J, et al, Development of high throughput screening assays using fluorescence polarization: nuclear receptor-ligand-binding and kinase/phosphatase assays.). The FP-based estrogen receptor (ER) assay is based on the competition of fluorescein-labeled estradiol and estrogen-like compounds for binding to ER. In a screen of 50 lead compounds from a transcriptional activation screen, 21 compounds had IC50 values below 10 microM, with one exhibiting roughly a 100-fold higher affinity for ERbeta over ERalpha. An FP-based competitive binding assay can be used to screen diverse compounds with a broad range of binding affinities for ERs.

Phosphatases and Kinases;

A nonradioactive, simple, sensitive fluorescence polarization assay has been developed to assay protein tyrosine kinase activity (Seethala R.; Menzel R. A Homogeneous, Fluorescence Polarization Assay for Src-Family Tyrosine Kinases. Analytical Biochemistry, November 1997, vol. 253, no. 2, pp. 210-218(9)). This assay involves incubation of a fluorescenylated peptide substrate with the kinase, ATP, and anti-phosphotyrosine antibody. The phosphorylated peptide product is immunocomplexed with the anti-phosphotyrosine antibody resulting in an increase in the polarization signal as measured in a fluorescence polarization analyzer. These results show that the fluorescence polarization assay can detect inhibitors and is comparable to the 32 PO 4 transfer assay. The fluorescence polarization method is advantageous compared to the 32 PO 4 transfer assay or ELISA or DELFIA because it is a one-step assay that does not involve several washings, liquid transfer, and sample preparation steps. It has the added advantage of using nonisotopic substrates. The fluorescence polarization assay thus is environmentally safe and minimizes handling problems.

G-Protein Coupled Receptors;

High-throughput fluorescence polarization (FP) assays offer a nonradioactive, homogeneous, and low-cost alternative to radioligand binding assays for cell surface receptors (G protein-coupled receptors and ligand-gated ion channels) (Allen M, Reeves J, Mellor G. High throughput fluorescence polarization: a homogeneous alternative to radioligand binding for cell surface receptors. J Biomol Screen. 2000 April; 5(2):63-9.). FP assays were shown to work across a range of both peptide (vasopressin V1a and delta-opioid) and non-peptide (beta 1-adrenoceptor, 5-hydroxytryptamme3) receptors. Assays could be run in 384-well plates with little loss of signal window or sensitivity compared to 96-well plate assays. New advances in FP measurement have therefore enabled FP to offer a high throughput alternative to radioligand binding for cell surface receptors.

GTPases;

A 30,000-member compound library was screened using filter binding [FB (33 P)] and FP detection systems, and compounds that were active in either assay were retested in 5-point curve confirmation assays (C L. Hubert et al. Data Concordance from a Comparison between Filter Binding and Fluorescence Polarization Assay Formats for Identification of ROCK-II Inhibitors). Analysis of these data showed an approximate 95% agreement of compounds identified as active in both assay formats. Also, compound potency determinations from FB and FP had a high degree of correlation and were considered equivalent. These data suggest that the assay methodology has little impact on the quality and productivity of the screen, provided that the assays are developed to standardize kinetic conditions.

Diagnostics using Antibodies;

The control of equine infectious anemia virus (EIAV) infections of horses has been over the past 20 years based primarily on the identification and elimination of seropositive horses, predominantly by a standardized agar gel immunodiffusion (AGID) assay in centralized reference laboratories. Peptides derived from antigenic regions of EIAV core and envelope proteins were initially screened for their utility as probes in an FP assay to select the best peptide antigen candidates (S. B. Tencza, et al. Development of a Fluorescence Polarization-Based Diagnostic Assay for Equine Infectious Anemia Virus. Journal of Clinical Microbiology, May 2000, p. 1854-1859, Vol. 38, No. 5). The FP assay was optimized to detect the presence of EIAV-specific antibodies by a change in the FP of a fluorescein-labeled immunoreactive peptide diagnostic antigen. The most sensitive and specific peptide probe was a peptide corresponding to the immunodominant region of the EIAV transmembrane protein, gp45. This probe was tested for its reactivity in the optimized FP assay with 151 AGID-positive horse sera and 106 AGID-negative serum samples. The results of these studies demonstrated that the FP assay reactivity correlated with reported AGID results in 106 of 106 negative serum samples (100% specificity) and in 135 of 151 positive serum samples (89.4% sensitivity). The FP assay was also found to have a very low background reactivity and to readily detect antibodies produced early in infection (<3 weeks postinfection).

FP is a homogeneous technology with very rapid reactions; seconds to minutes suffice to reach equilibrium. As the reagents are stable, large highly reproducible batches may be prepared. Because of these properties, FP has proven to be highly automatable, often performed with a single incubation with a single, premixed, tracer-receptor reagent. The fact that there are no washing steps increases the precision and speed over heterogeneous technologies and dramatically reduces waste.

Other homogeneous technologies based on fluorescence intensity have been developed. These include energy transfer, quenching, and enhancement assays. FP offers several advantages over these. The assays are usually easier to construct, since the tracers do not have to respond to binding by intensity changes. In addition, only one tracer is required and crude receptor preparations may be utilized. Furthermore, since FP is independent of intensity, it is relatively immune to colored solutions and cloudy suspensions. FP offers several advantages in the area of instrumentation. Because FP is a fundamental property of the molecule, and the reagents are stable, little or no standardization is required. FP is relatively insensitive to drift in detector gain settings and laser power.

The concept of molecular movement and rotation is the basis of fluorescence polarization. By using a fluorescent dye to label a small molecule, its binding to another molecule of equal or greater size can be monitored through its speed of rotation. As shown in FIG. 5, dye molecules with their absorption transition vectors (arrows) aligned parallel to the electric vector of linearly polarized light (along the vertical page axis) are selectively excited. For dyes attached to small, rapidly rotating molecules, the initially photoselected orientational distribution becomes randomized prior to emission, resulting in low fluorescence polarization. Conversely, binding of the low molecular weight tracer to a large, slowly rotating molecule results in high fluorescence polarization. Fluorescence polarization therefore provides a direct readout of the extent of tracer binding to proteins, nucleic acids and other biopolymers.

Fluorescence polarization, first described in 1926 by Perrin, has a long history. FP theory and the first instrument for measuring was developed by Weber. This work was expanded to biological systems, such as antigen-antibody reactions and hormone-receptor interactions by Dandliker. The first commercial systems, aimed at monitoring drugs in body fluids come from Jolley and co-workers.

Fluorescence polarization is defined by the following equation: $P=(V-H)/(V+H)$ where P is the polarization unit, V is the intensity of the vertical component of the emitted light, and H is the intensity of horizontal component of the emitted light of a fluorophore excited by vertical plane polarized light. The "polarization unit" P is a dimensionless entity and is not dependent on the intensity of the emitted light or on the concentration of the fluorophore. This is the fundamental power of FP. The term "mP" is now in general use, where 1 mP equals one thousandth of a P.

The excitation dipole is the direction in which the molecule prefers to absorb light. The emission dipole is the direction in which a molecule prefers to emit light. This assumed (for the sake of simplicity) that these directions are parallel. In one experiment, if the fluorescent molecules are fixed so that all excitation dipoles are aligned in the vertical plane and assume there is only fluoresces with a polarization along the emission dipole then a maximum polarization unit of 1000 mP is observed. If, however, the excitation dipoles were randomly oriented this maximum polarization unit is reduced to 500 mP. In another experiment, if the requirement that the dipoles are fixed was removed and they are allowed to reorient between the time when they are excited and the time when they fluoresce the polarization unit falls below 500 mP.

In another experiment, a collection of randomly oriented transition moments are free to rotate. In this case, the polarization unit is between 0 and 500 mP and is dependent on how far the molecule has rotated during the fluorescence lifetime of the excited state. The smaller the molecule, the faster it rotates, and so the lower the FP will be. The rate of rotation of a molecule is described by the Stokes equation: $\rho=(3\eta V)/(RT)$ where $\rho$ is the rotational relaxation time (the time required to rotate through an angle whose cosine is 1/e, or approximately 68.5°), $\eta$ is the viscosity of the medium, V is the molecular volume of the molecule, R is the gas constant, and T is the temperature in degrees Kelvin. From the previous equations we can see that the higher the molecular weight of a molecule, the higher the rotational relaxation time will be; $V=vM$ where M (Perrin equation) is the molecular weight of the molecule in Daltons and v is its partial specific volume ($cm^3\ g^{-1}$). The Perrin equation was first described in 1926, and describes the relationship between the observed FP, the limiting polarization, the fluorescence lifetime of the fluorophore ($\tau$), and its rotational relaxation time. $((1/P)-(1/3))=((1/P_o)-(1/3))\times((1+(3\tau/P))$.

The shorter the fluorescence lifetime, the higher the FP will be. Conversely, the shorter the rotational relaxation time, the smaller the FP will be. Combining the Stokes equation and the Perrin equation, and substituting M for V and rearranging, we get the relationship between the molecular weight of a molecule and its FP (1/P is proportional to 1/M); $(1/P)=(1/P_o)+((1/Po)-(1/3))\times(RT/vM)\times(\tau/q)$. From this equation we can see that P equals Po in the limiting cases of high molecular weight, high viscosity, and short lifetime. In fact, $P_o$ can be determined by measuring FP at various viscosities, plotting P against $1/\eta$, and determining the intercept on the ordinate.

Organic fluorophores have characteristics, such as narrow excitation bands and broad red-tailing emission band. FIG.

Figure 6:
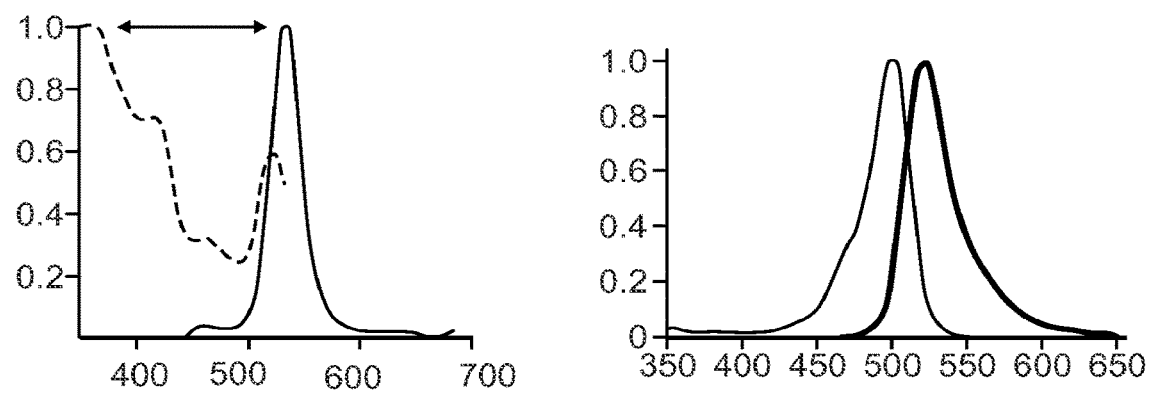
FIG. 6 is several graphs showing the absorption and emission spectra of q-dots and organic dye.
Figure 6:
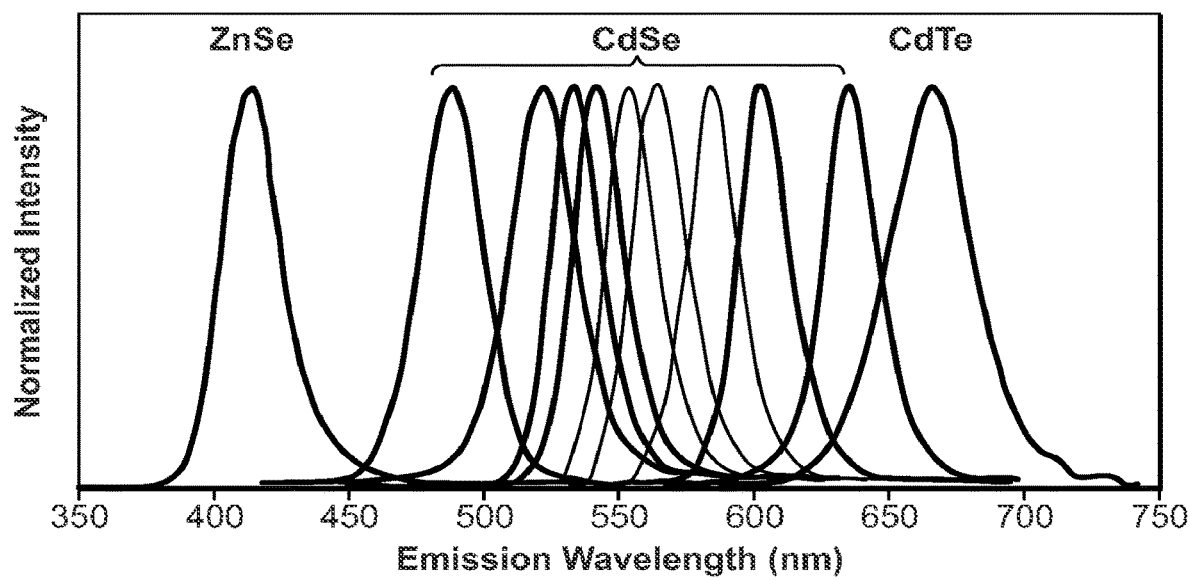

6 (Left, Center Panel) shows the absorption and emission spectra of q-dot 535 nanocrystals and fluorescein, respectively. FIG. 6 (Right panel) shows the emission spectra of a several sizes of CdSe—ZnS quantum dots, with excitation of ZhSe at 290 nm, all others at 365 mi. nm in all cases. These bands often limit their effectiveness. This makes concurrent resolution of multiple light-emitting probes problematic due to spectral overlap. Also, many organic dyes exhibit low resistance to photodegradation.

Luminescent colloidal semiconductor nanocrystals called quantum dots or q-dots (QD) are inorganic fluorophores that have the potential to circumvent some of the functional limitations encountered by organic dyes. In particular, CdSe—ZnS core-shell QDs exhibit size-dependent tunable photoluminescence (PL) with narrow emission bandwidths (FWHM~30 to 45 nm) that span the visible spectrum and broad absorption bands. These allow simultaneous excitation of several particle sizes (colors) at a common wavelength. This, in turn, allows simultaneous resolution of several colors using standard instrumentation (FIG. 6, right panel). CdSe—ZnS QDs also have high quantum yields, are resistant to photodegradation, and can be detected optically at concentrations comparable to organic dyes.

Quantum dots are nano-scale semiconductors typically consisting of materials such as crystalline cadmium selenide. The term 'q-dot' emphasizes the quantum confinement effect of these materials, and typically refers to fluorescent nanocrystals in the quantum confined size range. Quantum confinement refers to the light emission from bulk (macroscopic) semiconductors such as LEDs which results from exciting the semiconductor either electrically or by shining light on it, creating electron-hole pairs which, when they recombine, emit light. The energy, and therefore the wavelength, of the emitted light is governed by the composition of the semiconductor material. If, however, the physical size of the semiconductor is considerably reduced to be much smaller than the natural radius of the electron-hole pair (Bohr radius), additional energy is required to "confine" this excitation within the nanoscopic semiconductor structure leading to a shift in the emission to shorter wavelengths.

Figure 7:
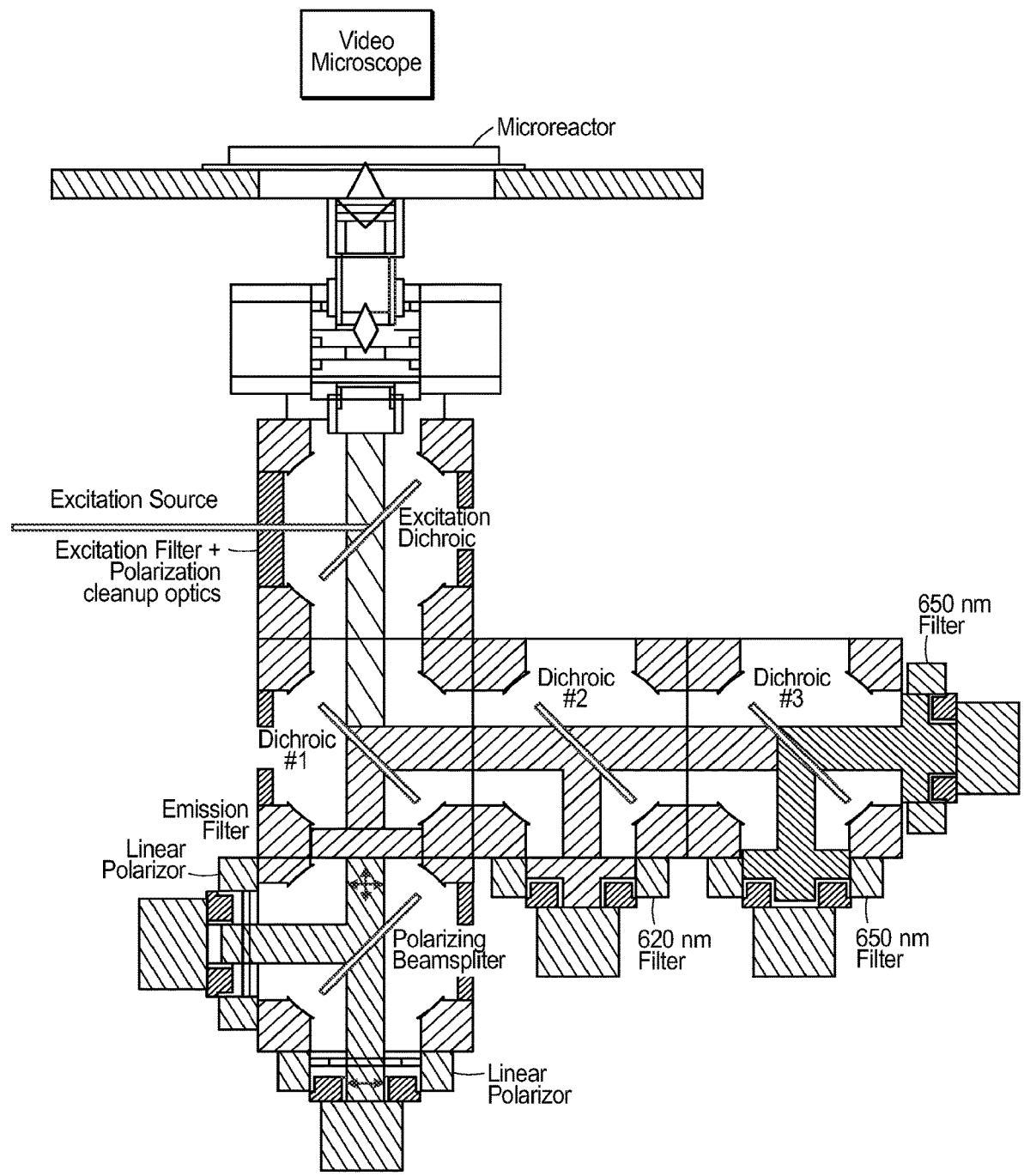
FIG. 7 is a schematic showing the extension to the fluorescence test station required to perform polarization fluorescence measurements simultaneously with q-dot readout.

Fluorescence polarization assays can be used in a microfluidics device to monitor the activity of kinase enzymes, phosphatases, proteases, ligand-ligand binding, and others. Extension of the existing fluorescence detection system to perform fluorescence polarization measurements requires the incorporation of a linearly polarized laser and polarizing optics into the design. As shown in FIG. 7, linearly polarized laser and polarizing optics is incorporated into the design. A linearly polarized frequency doubled diode laser operating at 488 nm passes through a ½ waveplate and linear polarizer (Meadowlark Optics, >2000:1 contrast ratio). This makes it possible to orient and lock the exciting laser polarization as required for FP. The laser is reflected and focused into the sample using a dichroic beamsplitter and anti-reflection coated lenses. Fluorescence from the sample is transmitted back through the lenses and dichroic beamsplitter and isolated using the emission filter. This fluorescence signal is then split into orthogonal polarizations using a polarizing beamsplitter (Meadowlark Optics polarizing cube beamsplitter, contrast ratio >500:1 transmitted, >20:1 reflected). Contrast is further enhanced with linear polarizers (Meadowlark Optics, >2000:1 contrast ratio). Finally, each polarization signal is measured using a pair of photomultiplier tubes (Hamamastsu H5789), digitized and analyzed by computer. A linearly polarized (>200:1) frequency doubled diode laser operating at 488 nm from Picarro is used for this purpose. As seen in the figure, the laser passes through a Vt waveplate and linear polarizer (Meadowlark Optics, >2000:1 contrast ratio). This makes it possible to orient and lock the exciting laser polarization as required for FP. As with the standard station, the laser is reflected and focused into the sample using a dichroic beamsplitter and anti-reflection coated lenses. Fluorescence from the sample is transmitted back through the lenses and dichroic beamsplitter and isolated using the emission filter. This fluorescence signal is then split into orthogonal polarizations using a polarizing beamsplitter (Meadowlark Optics polarizing cube beamsplitter, contrast ratio >500:1 transmitted, >20:1 reflected) and contrast is further enhanced with linear polarizers (Meadowlark Optics, >2000:1 contrast ratio). Finally, each polarization signal is measured using a pair of photomultiplier tubes (Hamamastsu H5789), digitized and analyzed on the computer. It is expected that these optics will permit better than mP sensitivity.

Figure 8:
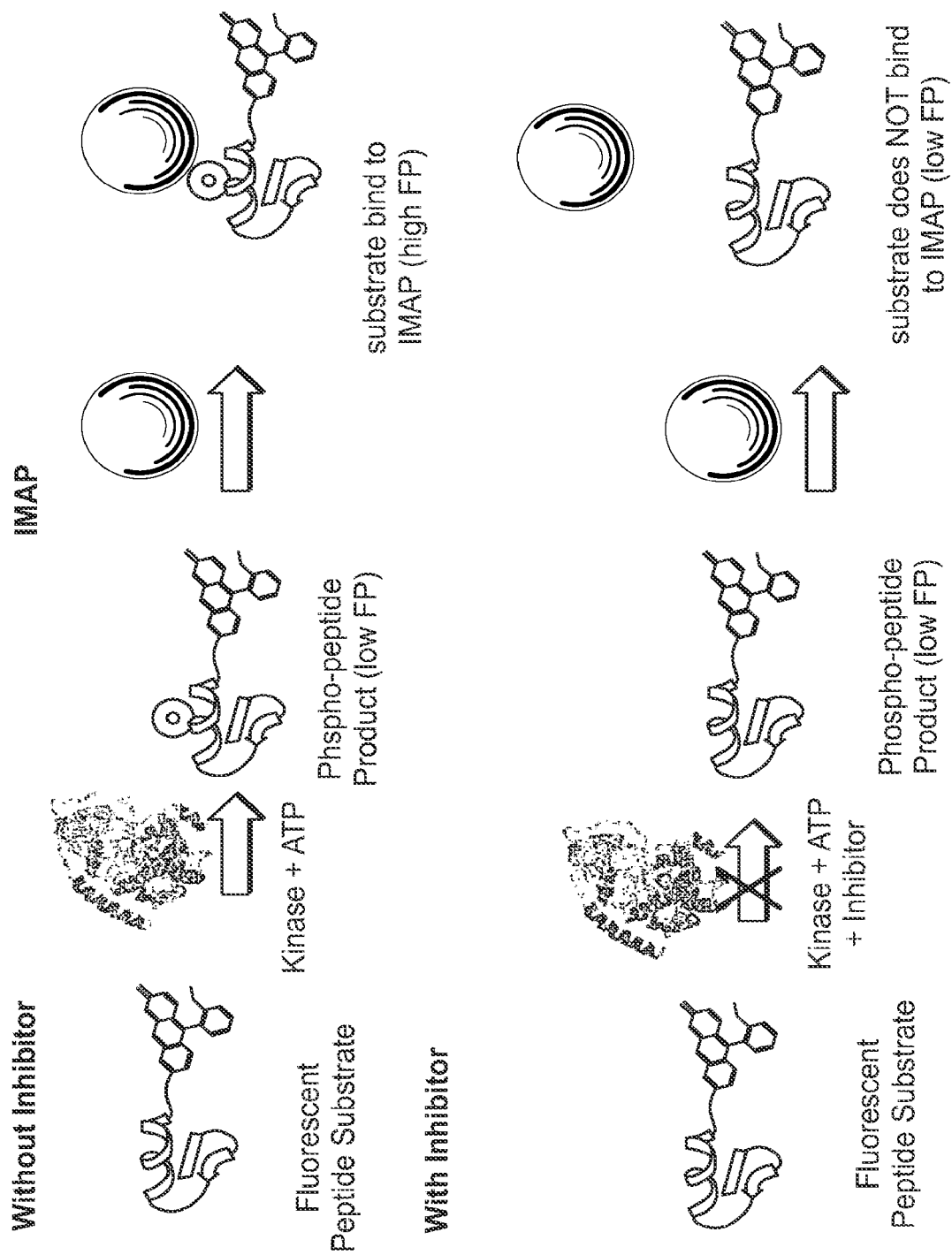
FIG. 8 is a schematic and accompany graphs showing a fluorescence polarization based kinase assay.

These fluorescence polarization systems were tested using a model enzyme system; Src-family tyrosine ldnase. A nonradioactive, simple, sensitive fluorescence polarization assay has been developed to assay protein tyrosine kinase activity (Seethala R.; Menzel R. A Homogeneous, Fluorescence Polarization Assay for Src-Family Tyrosine Kinases. Analytical Biochemistry, November 1997, vol. 253, no. 2, pp. 210-218(9)). This assay involves incubation of a fluorescenylated peptide substrate with the kinase, ATP, and anti-phosphotyrosine antibody. As shown in FIG. 8, the phosphorylated peptide product is immunocomplexed with the anti-phosphotyrosine antibody resulting in an increase in the polarization signal as measured in a fluorescence polarization analyzer. FIG. 8, left panel, shows the IMAP principle of operation. When a fluorescent substrate is phosphorylated by a ldnase, it can bind to the IMAP binding reagent, whose molecular size is large relative to the substrate. This gives a large increase in the polarization of the fluorescence. FIG. 8, middle panel, shows the IMAP assay of MAPKAP-K2, a serine/threonine kinase. MAPKAP-K2, from Upstate, was assayed in a volume of 20 μL using the amounts of enzyme indicated. Concentrations of ATP and substrate were 5.0 and 0.5 μM, respectively. Incubation was 60 minutes at room temperature, followed by the addition of 60 μL IMAP binding reagent. FP was read on an Analyst system 30 minutes later. FIG. 8, right panel, shows the IMAP quantification of kinase inhibition. MAPKAP-K2 (0.25 units/mL) was incubated using the amounts of enzyme shown for 15 minutes. The activity of the enzyme was then assessed as described in above. These results show that the fluorescence polarization assay can detect inhibitors and is comparable to the $^{32}PO_4$ transfer assay. The fluorescence polarization method is advantageous compared to the $^{32}PO_4$ transfer assay or ELISA or DELFIA because it is a one-step assay that does not involve several washings, liquid transfer, and sample preparation steps. It has the added advantage of using nonisotopic substrates. The fluorescence polarization assay thus is environmentally safe and minimizes handling problems.

The dyes that are chosen are used extensively in flow cytometry and in our instrument will be determining the status of (potentially) many dyes within one drop. The use of inexpensive optics on our instrument will be more than compensated for by the theoretical increase of dye molecules in the nanoreactor.

FP assays have been shown to tolerate up to 5% DMSO with no loss in sensitivity or signal window. From a random set of 1,280 compounds, Allen et al found that 1.9% significantly interfere with FP measurement (J Biomol Screen. 2000 April; 5(2):63-9. High throughput fluorescence polarization: a homogeneous alternative to radioligand binding for cell surface receptors. Allen M, Reeves J, Mellor G. Receptor & Enzyme Screening Technologies, Glaxo Wellcome Medicines Research Centre, Stevenage, Herts, UK.). If fluorescent or quenching compounds were eliminated (3% of all compounds), less than 0.4% of compounds were found to interfere with FP measurement. Compounds are assayed a priori and those that have these undesirable characteristics are eliminated.

In some enzymatic assays, a delay module (i.e., delay line) will be utilized. This is less true for enzyme reaction mechanisms in a small volume. And even many cell-based assays can be measured within 5 minutes. Longer assay times can be accomplished by collecting the droplets, incubating them for an appropriate amount of time, and then re-injecting them into the device.

Three different q-dots in several concentrations each can be placed in a microdroplet, and can then be used with the device of the present invention to decode what is in the drop. In one experiment, the initial labeling scheme used three colors of q-dots having emission wavelengths of 620 run (CdSe/ZnS), 650 nm (InGaP/ZnS), and 680 nm (InGaP/ZnS) (excitation at 488 nm is appropriate for all). In one specific example, one q-dot was maintained at a constant concentration and varying the second and third q-dots at least 10 different concentrations giving 100 different encodes (1×10×10). Decoding will be computed by referencing the intensity of the second and third q-dots relative to the first q-dot. Other labeling schemes can be used during the course of these experiments.

The Q-dot readout extension to the fluorescence station is described herein and is easily incorporated into the design due to the modular layout developed. As seen, a series of dichroic beamsplitters, emission filters, and detectors are stacked onto the system, allowing measurement of the required five emission channels (two fluorescence polarization signals and three q-dot bands). Dichroic beamsplitters and emission filters capable of separating the q-dot wavelength bands from each other are readily available, so it is a straightforward process to configure the station appropriately.

The residence time can be increased by slowing down the flow of drops by widening the channel. Alternatively the intensity of the laser beam can be increased to compensate or increase the concentration of the q-dots within the droplet.

As described herein, the dyes chosen for FP are commonly used in most cell- and enzyme-based assays and are designed not to overlap significantly with the q-dots. The dyes are evaluated both independently and together with the q-dots (at first off-instrument) to assess the cross-talk. Preferably, the liquid q-dot labels are read outside a spectral wavelength band currently used in FACS analysis and sorting (i.e., the dyes flourescein, Cy3, Cy5, etc). This permits the use of currently-available assays (dependent on these dyes). Using specific q-dots, crosstalk is minimized. Several commercial entities sell q-dots that can be read by the optics being designed. The three colors of q-dots used currently are the non-functionalized T2 EviTags having emission wavelengths of 620 nm (CdSe/ZnS), 650 nm (InGaP/ZnS), and 680 nm (InGaP/ZnS) (excitation at 488 nm is appropriate for all).

It is possible to generate 96 types of droplets, each droplet containing both a unique set of q-dot labels and a chemical compound, and as the droplet flows through the device of the present invention kinase enzyme activity can be analyzed using FP and the q-dot label can be decoded. This method allows for scaling to more complex and interesting libraries.

FP assays have been shown to tolerate up to 5% DMSO with no loss in sensitivity or signal window. From a random set of 1,280 compounds, Allen et al. found that 1.9% significantly interfere with FP measurement (J Biomol Screen. 2000 April; 5 (2): 63-9. High-throughput fluorescence polarization: a homogeneous alternative to radioligand binding for cell surface receptors. Allen M, et al. Receptor & Enzyme Screening Technologies, Glaxo Wellcome Medicines Research Centre, Stevenage, Herts, UK.). If fluorescent or quenching compounds are eliminated (3% of all compounds) then less than 0.4% of compounds are found to interfere with FP measurements. Compounds are assayed a priori and those that quench FP are eliminated.

The three colors of q-dots we will use are the non-functionalized T2 EviTags having emission wavelengths of 620 nm, 650 nm, and 680 nm; excitation at 488 nm is appropriate for all. The >620 nm liquid labeling emission band was chosen not to interfere with the FP assay band found between 488 and 620 nm. These q-dots are commercially-available, stable in some buffers and remain suspended in aqueous solution.

A mixture of two types of droplets, buffer-only and fluorescein-containing, are stable for at least 1 month without any detectable diffusion of the organic dye into the buffer-only droplets. Other surfactants may be substituted for different kinds of compounds. For other compound testing, i) similar mixtures of compound-containing and buffer-only droplets can be created, ii) they can be sorted based on their q-dot labels, and iii) Mass Spectrometry can be used on the buffer-only droplets to quantitatively detect the presence of other chemicals compounds.

In some embodiments, a delay module (i.e., delay line) can be utilized. This will be true for enzyme reaction mechanisms in a small volume. But even many cell-based assays can be measured within 5 minutes. Droplets can also be taken off-line and stored for at least a month a month before re-injection into the device of the present invention with no apparent change in the droplets. Longer delay times can be achieved by taking mixed droplets offline, and then re-injected them.

Example 5

The present invention provides methods for performing condensation chemistry in nanoreactors of the present invention as described to synthesize libraries of drug-like molecules in a highly convergent manner.

All life processes can be reduced to chemical reactions that take place in aqueous media. Hence water is considered to be the universal ultimate solvent and inevitably biological experiments are performed in aqueous media. Furthermore, organic solvents of all types are detrimental to biochemical reactions limiting their use to small percentages of water miscible solvents such as dimethyl sulfoxide and ethylene glycol. On chip synthesis in our system therefore requires that all chemical reactions are performed in biologically compatible aqueous media. In contrast, conventional synthetic organic chemistry relies on highly activated substrates and highly reactive reagents to conduct bond forming processes. Typically these substrates and/or reagents are unstable in the presence of and react with water rendering them useless. An ever increasing effort to reduce cost, enhance safety and to address environmental concerns w.f.t. solvent choice has driven the development of synthetic methods that utilize water as the primary and in many cases the only solvent (Li). In the case in which water is not the only solvent, water miscible organic solvents are used to aid the dissolution of substrates.

While material can be removed from NanoReactors by breaking them in a controlled way, it is preferable to avoid having to do so. To eliminate the requirements of removing material from doplests, we have identified 5 reaction types, which can be performed in aqueous media, that can be used to "stitch" drug-like molecules together from a highly diverse library of sub-structural components. These reactions generate commonly occurring functional groups in drug-like molecules and include: i) N-Acylation ii) N-Sulfonylation iii) Cycloadditions iv) Reductive alkylation of amines and v) SNAr reactions (Morgan). Random combination of sub-structures will yield a library of all possible combinations. The reactions are sufficiently orthogonal to perform multi-step reactions. Furthermore, simple protection and deprotection schemes can be used to increase the number of condensations. A sufficient number excess of component nanoreactors will yield a library of all possible combinations with multiple copies of each combination for testing in a biomolecular assay. This redundancy is required to reduce the impact of false positive sorting events.

Figure 9:
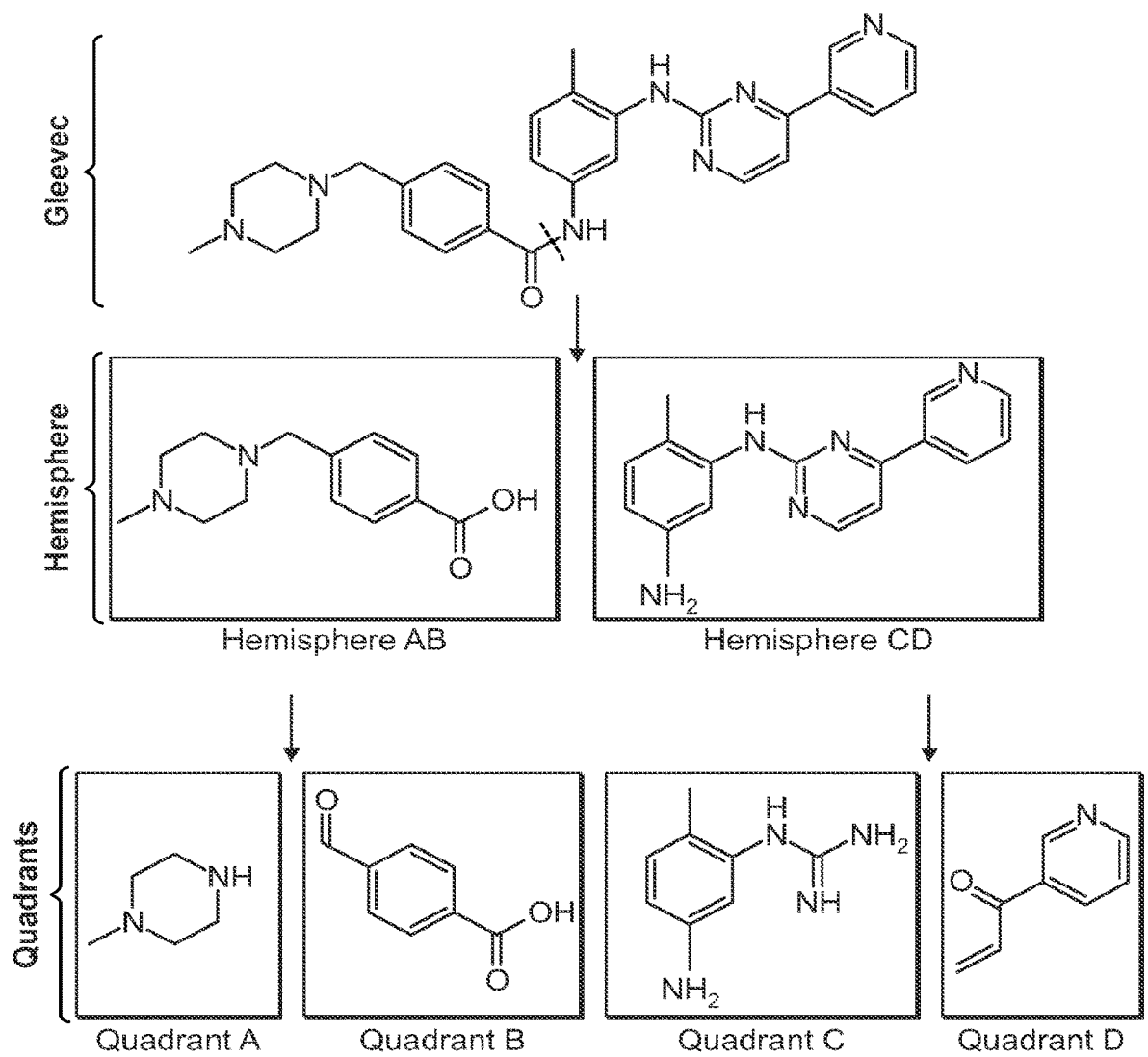
FIG. 9 is a schematic illustrating the retrosynthetic analysis of Gleevec.

This technology is based on the assembly of drug-like chemical entities by two or more step convergent syntheses from diverse sub-structural components. A two step process would assemble the final chemical species from four sub-structures. An example of such a synthesis is the construction of the kinase inhibitor Gleevec from relatively simple building blocks. Gleevec is the first of a class of kinase inhibitors which targets the chimeric tyrosine kinase bcr-abl. Bcr-abl is constitutively active causing a rare life-threatening form of cancer called chronic myeloid leukemia (CML). Gleevec was given FDA approval in a record breaking three months in May of 2001. Analogues to a sphere, the three dimensional structure can be broken down into hemispheres and quadrant by the appropriate disconnections. FIG. 9 shows that Quadrants A and B are combined utilizing a reductive alkylation. Quadrant C and D are combined utilizing a 1,3 dipolar cycloaddition. The Hemisphere AB and CD are combined utilizing an N-acylation Chemical Diversity is achieved by varying the sub-structural units (Quadrants) and randomly combining to achieve all possible combinations. Table 1 shows the theoretical diversity for number of each quadrant (e.g. 4 different Quadrants A, with 4 different Quadrants B, with 4 different Quadrants C and 4 different Quadrants D yield 256 unique products after two steps as described above.

TABLE 1

| Diversity of quadrants (equal number of diverse members for each quadrant) | Number of Unique solutions |
|---|---|
| 1 | 1 |
| 2 | 16 |
| 3 | 81 |
| 4 | 256 |
| 5 | 625 |
| 6 | 1,295 |
| 7 | 2,401 |
| 8 | 4,096 |
| 9 | 6,561 |
| 10 | 10,000 |

Sufficiently diverse condensation chemistry in aqueous media exists to synthesize diverse-libraries of drug-like molecules in a highly convergent manner.

The majority of synthetic reactions routinely used in the synthesis of complex drug-like molecules rely on reagents and substrates which are sensitive to hydrolysis in the presence of water and hence require stringent exclusion of water from the reaction vessel. Furthermore, condensation reaction often require the equivalent of a dehydration to proceed, with one or both of the condensation substrates being sensitive to degradation by water. The pursuit of "greener" chemistry, using benign and environmentally friendly solvents such as water, has resulted in the development of several condensation reactions which take place in the presence of water. Aqueous organic chemistry has been extensively reviewed in the primary literature and books.

The encapsulation technology of the present invention which relies on the addition of reagents and/or substrates to nanoreactors without the option for reaction work-up (i.e. purification of product). This precludes the use of reactions which have side products which could potentially interfere with subsequent steps or the biological assay intended to be performed on the final product. Furthermore, in multistep reactions, the two steps will have to be orthogonal with respect to their coupling chemistry, i.e. the functional groups for consecutive reactions may not interfere with each other. Five reaction types have been identified which can be performed in aqueous media and which do not require purification of the product prior to the next synthetic step or testing in biological assays. These reactions include: i) N-Acylation ii) N-Sulfonylation iii) Cycloadditions iv) reductive alkylation of amines and v) SNAr reactions.

The present invention provides methods of performing these condensation reactions in a highly convergent, "one pot" synthesis to stitch together complex drug-like molecules from at least 2-16 substructures.

The solubility of organic compounds in aqueous media is strongly dependent on their structure. To enhance solubility of the library compounds in aqueous media, it is common in the biomolecular screening community to dissolve library compounds in DMSO and subsequently dilute the DMSO solution with water. DMSO is compatible with the nanoreactors described herein.

A fluorescent product resulting from the condensation of two suitable fragments can be distinguished from droplets that have components which did not react to form the fluorescent product thus enabling the optical readout to distinguish between the two cases and sort the droplets accordingly. The components able to form the fluorescent product would contain a different tag from the components which are not able to form a fluorescent product. Hence this system can be used to test the tagging strategy chosen to identify the composition of the final product.

Traditional combinatorial chemistry relies on complex deconvolution methods to determine the structural identity of the final product once it has been determined to be active in any particular biomolecular assay. Massively parallel synthetic approaches use encoding technologies to infer the structure of any particular product from the tag associated with it which typically identifies the reaction history of that particular compound. In one example, the reagent droplets are encoded with nucleic acids tag which will provide a unique PCR signature for the final product from which the reactant composition and hence structure can be inferred.

Figure 10:
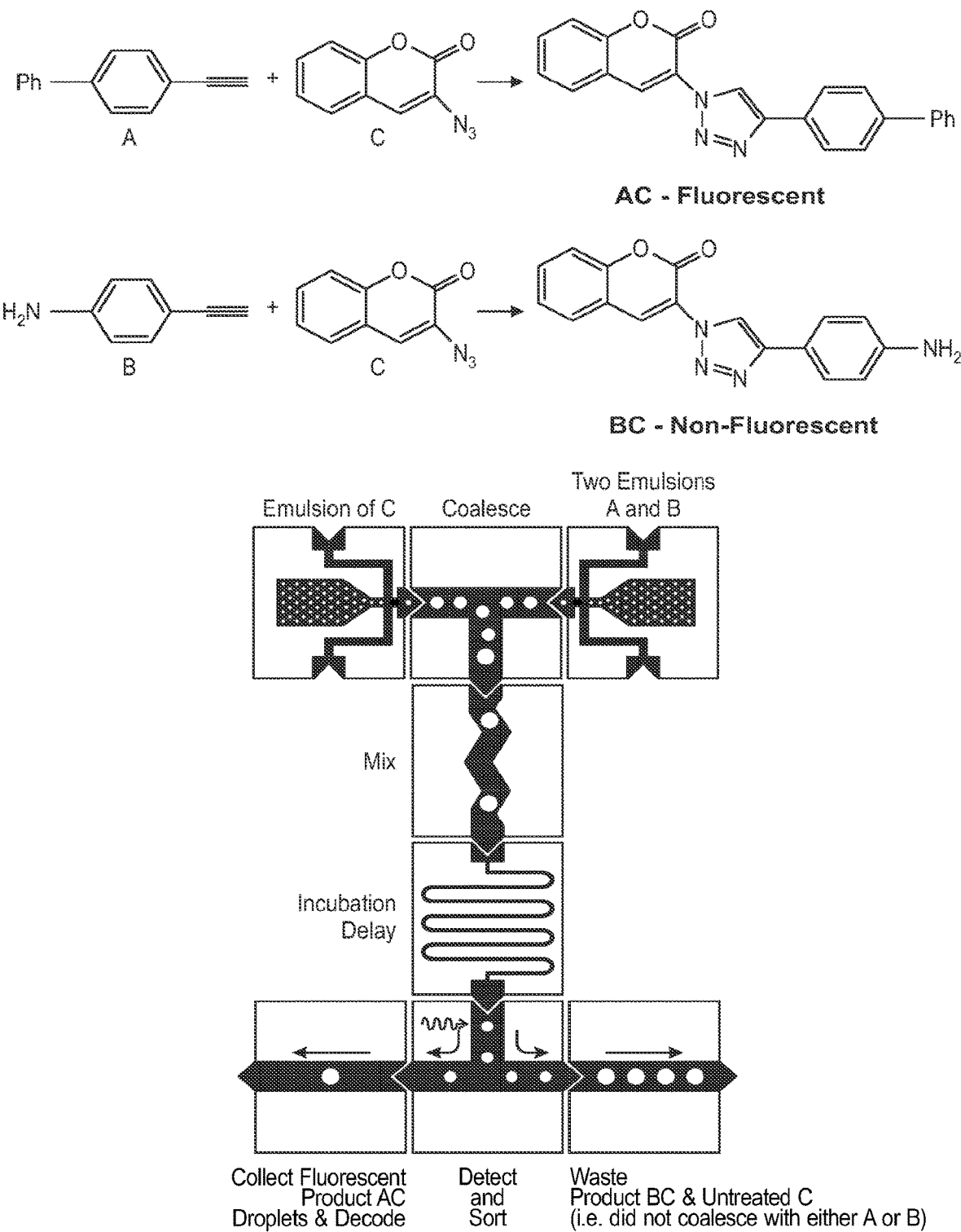
FIG. 10 is a schematic illustrating the synthesis of a fluorescent and non-fluorescent product from the same precursor.

The synthesis of a fluorescent molecule which will be the product of one particular component with a common reaction partner will be used to test the tagging technology. FIG. 10 shows three tags denoted A, B and C label one of each of the following unique components: A is a fragment which if combined with C will yield a fluorescent molecule. B is a fragment which if combined with C will yield a non-fluorescent molecule. The fluorescence detector will be able to distinguish between drops that contain A 5 B, C or the mixture BC and between the drops which contain the mixture AC (if the reaction has taken place and the fluorescent product is formed). The fluorescence based sorting will yield a population of AC tags which are completely devoid of B. The second (waste) population of drops may contain B, C and A tag if not every drop containing the tag A has been fused to a drop containing C.

Multistep convergent syntheses of drug-like compounds can be performed in nano-reactors by the selective fusion of droplets. These compounds can then be tested in a biomolecular screen immediately after being synthesized on chip.

The synthesis of the bcr-abl kinase inhibitor Gleevec has been described herein. The synthesis of this inhibitor from four sub-structural units followed by an assay determining its ability to inhibit the bcr-abl kinase in a fluorescence polarization based assay would serve as proof of principle for this technology.

Two different sub-structures will be used for each quadrant such that at least 16 possible products can be formed of which one is Gleevec. Although some of the other products will have sub-structural elements of Gleevec, the "alternative" quadrants will be considerably different to ensure that a completely non-active product will be amongst the possible combinations. Each unique quadrant will be tagged with a suitable nuclei acid oligomer.

The products will be tested in a fluorescence polarization based kinase assay with the expectation that Gleevec will strongly inhibit the activity of bcr-abl. Based on the assay readout, the drops containing Gleevec will be sorted and collected separately. Analysis of the nucleic acid tags of those drops can reveal the composition of the hit compound.

Figure 11:
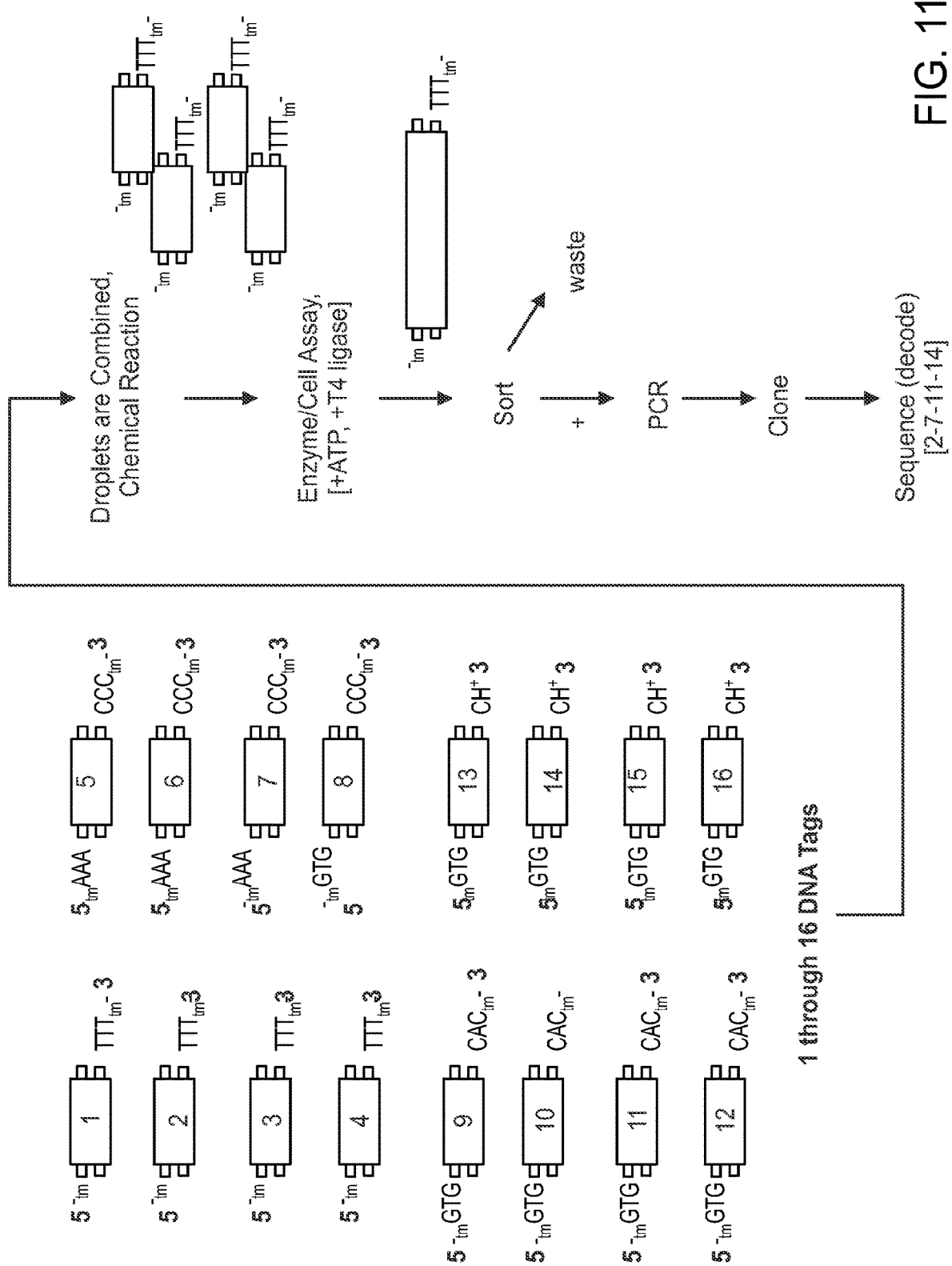
FIG. 11 is schematic showing the use of nucleic acids for chemical encoding and decoding tagging of chemical reactions.

The present invention also provides methods of using nucleic acids for chemical encoding and decoding tagging of chemical reactions Current technology exists for the tagging of beads with chemical tags which "record" the synthetic history of any particular bead thereby allowing the deconvolution of the active small molecule's structure. The encapsulation of the reagents used to assemble the library members enables the use of homogeneous nucleic acid based tags to determine the structure of any particular quaternary reaction combination. Positive hits from the biomolecular screen would be cloned into E. coli and decoded using polymerase chain reaction (PCR) to determine the composition of quadrants used to assemble the bio-active molecule. FIG. 11 (left panel) shows four groups of DNA tags. One of sixteen double-stranded oligodeoxynucleotide 'surrogate' tags will be added to each of four 'groups' of the sixteen different chemicals being used for chemical synthesis (see text for details). Each group of tags will have unique overlapping 5' and 3' ends that are the same for each member of the group, but complementary between adjacent groups. The tags within the groups are designed with asymmetric 5' overhangs such that they can ligate once with a member of an adjacent group. The first and fourth groups will additionally contain 5' and 3' sequences (respectively) that can be used as priming sites to PCR up final products containing all four groups. The top-strand in groups 2, 3 and 4 will contain a 5' phosphate needed for DNA ligation. FIG. 11 (right panel) shows the tags in each reaction are sorted based on the enzyme assay. In the example shown, chemical synthesis is allowed to occur (see text for details) and droplets (in this example) containing tags 2, 7, 11 and 14 have within them a synthesized compound that reacts positively in an enzyme/cell-based assay. The positive droplets are then subjected to a polymerase chain reaction (PCR) using primers complementary to the ends of groups 1 and 4. The resulting PCR product will next be cloned into an appropriate DNA vector. Finally, colonies of transformed E. coli containing the catenated tags will be DNA-sequenced to decode the synthesis history of the compound associated with positively-sorted droplets.

Alternatively soluble quantum dot dyes can be used to encode the input emulsions which can identify the chemical composition of a positive hit by measuring relative fluorescence signals of multicolored quantum dots eliminating the need for sorting. An assay point with appropriate signal from a fluorescent marker (in the case of the kinase assay proposed here we would measure changes in fluorescence polarization) the synthetic history of the molecule responsible for this signal would be read out by determining relative levels of dyes. This tagging technology is limited by the number of unique combinations that can be discerned with appropriate confidence and hence would be applied to smaller, more focused libraries typically used to explore a sub-set of chemical space surrounding an early lead.

Example 6

The present invention provides methods of isolating self-antigens. A first sample droplet set consisting of a tumor obtained from a multicellular organism treated in such a way as to create single cells that are then each separately or multiply contained within said first droplet set are combined with a second set of droplets consisting of one or more t-cells isolated from the organism, and the resulting combined droplets are analyzed for t-cell killing of the tumor cells contained within the combined droplets using a detecting means. The detecting means can include analysis for cytoplasmic enzymes that would be released to the droplet environment upon cell lysis. The droplets can be either sorted or not sorted and then further analyzed for identification of tumor cell epitopes recognized by the t-cell.

Example 7

The present invention provides methods of matrix screening using a phased-drop approach or derivatives thereof. A device composed of a multitude of samples each separately contained within sample wells connected to one or more inlet channels such that that can be operated in such a way that each sample can be encapsulated within a droplet within a fluid-flow and be both sequentially and separately combined with each of the other samples by varying the phase of the combining of the separate, sequential droplets.

For example, by changing the phase of the combining of the drops it is possible to have, for example, with five separate samples each combine with the other samples, in this example in pairs, to yield drops containing a mixture of all possible pairs of compounds 1+2, 2+3, 3+4, 4+5, 5+1, . . . 1+4. The phasing can be by one of several means, including channel length, valves, pressure, etc.

In another example, a matrix of 100 chemical compounds are loaded into 100 separate wells and are each combined in separate pairs to yield $100^2$ different pairwise combinations. These $10^3$ combinations are each separately used in a cell-based assay to determine their combined effects on cell survival.

The devices and systems disclosed herein have several distinct advantages over current devices and methods for analyzing samples. These advantages include, for example:

reliability and reproducibility, flexibility (the ability to 'swap out'), the greatly reduced cost of an assay, speed and handling, reduced skill-level required needed to perform the an analysis, scalability of assays from one to many nanoreactors, automatable with current liquid-handling robotics, multiple sort capability and previously unachievable assay architecture enabled by NanoRector confinement and manipulation The enhanced functionality that electrostatic charge brings to droplets in microfluidic devices has the potential to enable an expansive list of microfluidics applications. This toolkit of techniques for manipulating droplets described herein can enable modular integration of systems for transporting and reacting small numbers of molecules. High throughput screening, combinatorial chemistry, and the search for rare biological function in libraries of biomolecules all benefit from electrostatic manipulation of droplets in microchannels. Droplet-based microfluidic technology can also be used to develop a chip-scale fluorescence activated cell sorter (FACS) with enhanced activation functionality that goes beyond fluorescence to include multiple reagent-based assays between the droplet formation and sorting steps. Moreover by using femtoliter droplets, which are a few microns in diameter, even a single biomolecule represents concentrations of >>1 nM, sufficient for efficient chemical reactivity and single-molecule assays.

Many of the potential uses of droplet-based microfluidic devices are driven by a need to encapsulate a varied population or library of molecules, cells or particles into microreactors, perform an assay on the contents, perhaps through the addition of reagents, and then, finally, to selectively remove specific microreactors from the collection in a search for rare events. This requires a processing rates of 10 3 per second to sort through the smallest libraries in a reasonable time while rates on the order 10 5 per second are desirable for larger libraries. These rates are feasible using the charged droplet paradigm. Moreover, because the microfluidic devices are stamped, parallel flow streams can be fabricated, further enhancing the total throughput. Combined, the advantages of droplets and high throughput manipulation provide significant opportunity for widespread application. The inventions presented and described in detail herein will facilitate the application of droplet-based microfluidic technology.

Example 8

The present invention also provides adaptations of known assays for use on the microfluidic device according to the present invention. For example, fluorescence polarization, molecular beacons, and taqman assays can be adapted for use in SNP, DGE, and nucleic acid identification. In a high-throughput mode the individual droplets can be labeled with either organic or inorganic dyes, or colored beads. A distinct advantage is that beads are not required and the entire assay can be performed in solution. Some exemplary assays are described.

The present invention can be used to identify CDRs in a pre-defined CDR library. In one example, there can be 100 pre-defined CDRs for each of the 6 CDRs in an scFv (i.e., 3 in VH, and 3 in VL). 600 molecular beacons can be created, each beacon separately emulsified with a different (for example, q-dot) LiquidLabel. The 600 separate emulsions can be pooled to create one emulsion library mixture (composed of 600 different types of droplets, and as stated each droplet containing both a molecular beacon specific to a specific CDR, and a LiquidLabel specific to droplets containing that molecular beacon). scFv Ab genes from antigen-interacting antibodies isolated by either phage display or yeast two-hybrid can be amplified by PCR using 5' and 3' flanking primers. The PCR product of the Ab gene can be either emulsified on the RDT Instrument prior to combining with the library mixture, or, in a separate example, combined with it's own unique LiquidLabel off-line, and mixed with several (other) amplified Ab fragments, thereby allowing several PCR fragments to be analyzed simultaneously. The amplified fragment will then be combined with the library mixture, and run past the detector. The detector will identify the molecular beacon within the droplet using the LiquidLabel and further detect whether hybridization has occurred by examining the status of the fluorophore relative to the probe-containing quencher.

An oligonucleotide assay can be used to generate a product against which an fluorescence polarization (FP) organic-dye type tag, molecular beacon or taqman oligonucleotide can be used in an assay as described above. Other assays are also possible.

The present invention can also be utilized in differential gene expression. Taqman or molecular beacons can be used in a modification of the methods as described herein.

Figure 12:
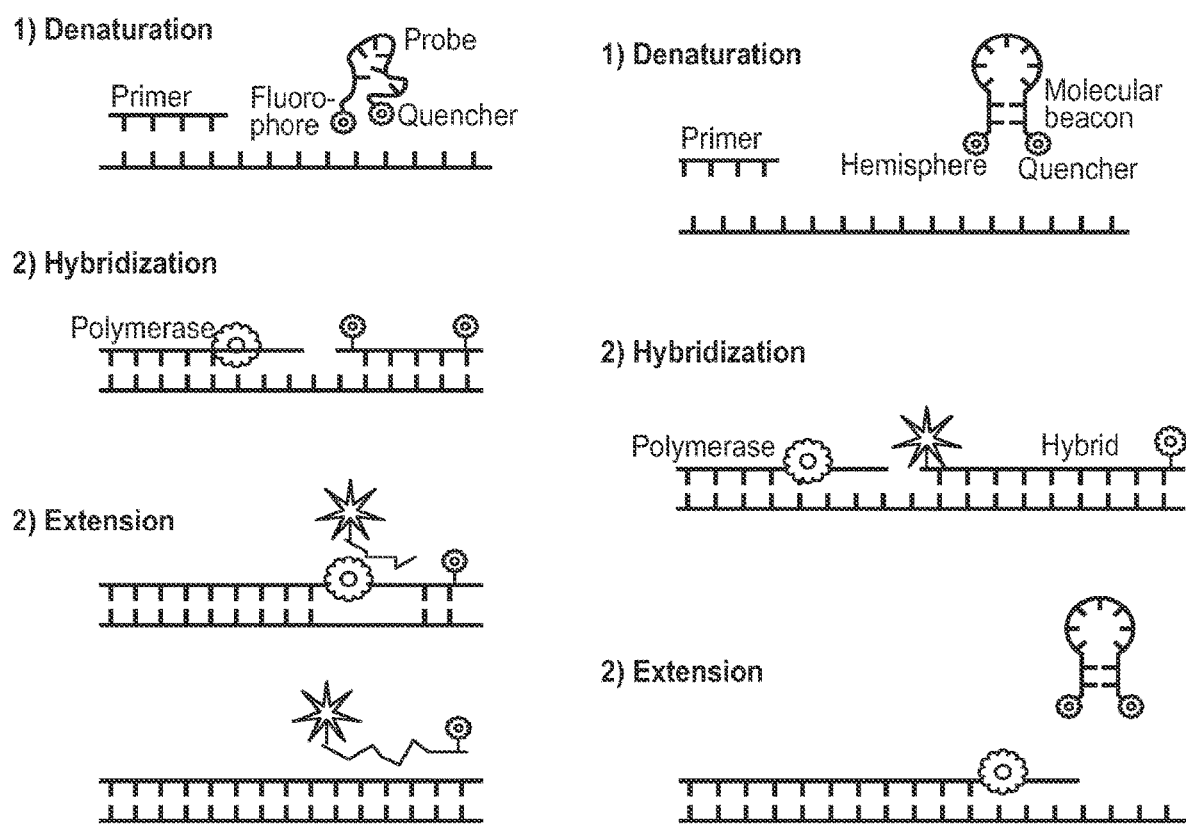
FIG. 12 is a schematic illustrating a taqman assay and molecular beacon probes.

The TaqMan system requires the use of a polymerase with 5' to 3' nuclease activity, such as Taq DNA polymerase, and a short oligonucleotide probe labeled with a reporter dye and a quencher dye that anneals to the target downstream from one of the primers (See, FIG. 12, left panel). If the probe is hybridized to the target, the polymerase cleaves the hybridized probe, separating the reporter from the quencher, which results in a higher fluorescent signal. The fluorescent signal increases proportionally to the number of amplicons generated during the log-linear phase of amplification. It is important that the probe hybridizes before the primers so the polymerase can cleave the probe and release the reporter dye as primers are extended. Otherwise, amplification occurs but is not monitored because the probe is not cleaved.

Molecular beacon probes are hairpin-shaped oligonucleotide molecules that have a fluorophore and a non-fluorescent quencher dye attached to the 5' and 3' ends (See, FIG. 12, right panel). Generally, DABCYL is the non-fluorescent universal quencher and the other dye is a reporter fluorophore such as, FAM, TET, TAMRA or ROX. The molecular beacon is in a hairpin configuration when it is not hybridized to the target site. It is designed to have two "arms" with complementary sequences that form a very stable hybrid or stem. The close proximity of the quencher and reporter suppresses reporter fluorescence when the beacon is in a hairpin configuration. When the beacon hybridizes to the target during the annealing step the reporter dye is separated from the quencher, which allows the reporter to fluoresce. In order for the beacon to anneal to the target sequence, it must form a hybrid that is even more stable than the hairpin to remain in the hybridized conformation. Therefore, the probe is less likely to form a hybrid with the target if there are mismatched base pairs.

In addition to molecular beacons and Taqman, the devices of the present invention can be used to carry out fluorescence polarization as described herein. Most SNP assays can be adapted for both mini-sequencing and gene expression analysis. A series of fluorescence polarization measurements have been made inside a microfluidic device according to the present invention while looking at droplets containing Fluorescein, Fluorescein bound to biotin, and Fluorescein bound to biotin+Steptaviden. The fluorescence signal was split into two orthogonal polarizations: one parallel to the laser excitation polarization, and one perpendicular to the polarization. These signal were collected and analyzed to determine the change in polarization of the fluorescence for each of these binding conditions.

The Polarization is calculated from:

$$P = \frac{(V - H)}{(V + H)}$$

Where V=fluorescence signal polarized parallel to laser excitation polarization, and H=fluorescence signal polarized perpendicular. A mP ("milli-P") is 1000*P. The Polarization is equal to zero when the fluorescence is completely depolarized, and has a maximum of 500 mP when the fluorescent molecule is "frozen" (i.e. bound to a large molecule that does not rotate between excitation and emission).

The fluorescence station was modified to include cleanup polarizer for the laser and a polarizing beamsplitter with cleanup polarizers for collection. The two resulting fluorescence channels collect light with orthogonal polarizations ("Vertical" is parallel to the laser polarization, "Horizontal" is perpendicular to the laser polarization). The device used to generate alternating droplets is built from RDT Master #257 (50 um deep channels). Table 2 lists the fluids used for these tests.

TABLE 2

Fluids ran through the double nozzle device.

| Fluid name | Composition |
| --- | --- |
| Oil | FC3283 + 10% "Avocado" |
| BTFC | 1 × $10^{-6}$ Molar Biotinylated Fluorescein in 10 mM Borate pH 9 |
| BTFC + SA | 1 × $10^{-6}$ Molar Biotinylated Fluorescein in 10 mM Borate pH 9 + 0.5 × $10^{-6}$ Molar Steptaviden (4 binding sites per molecule) |

Figure 13:
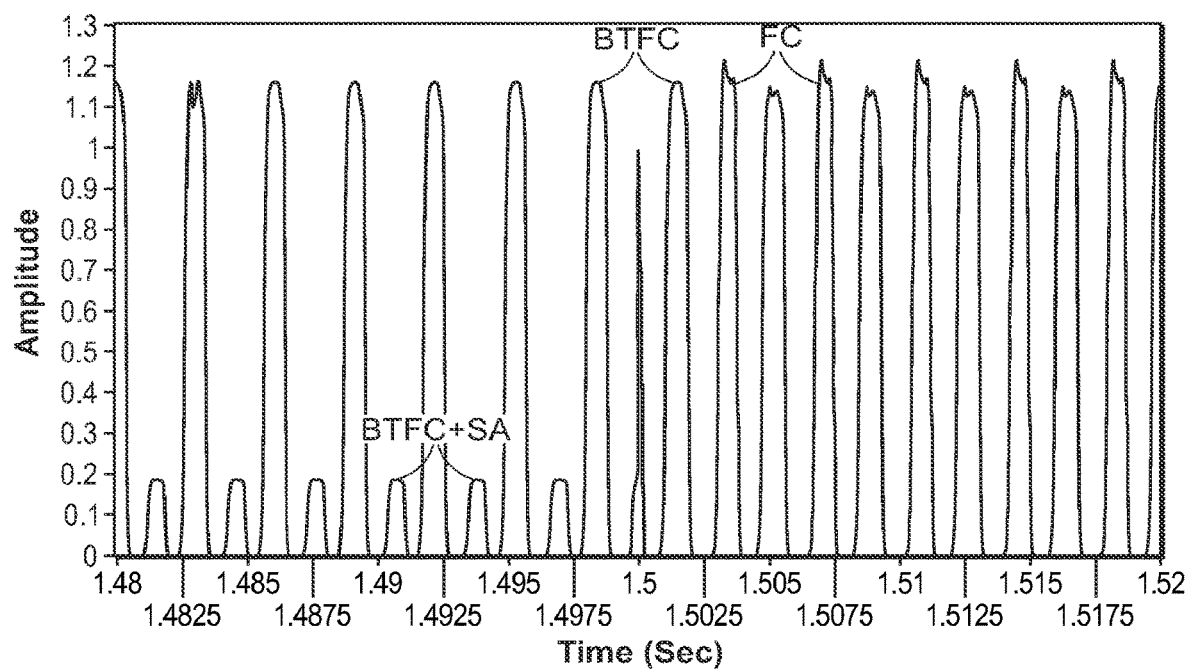
FIG. 13 is a graph showing polarized fluorescence signals.
Figure 13:
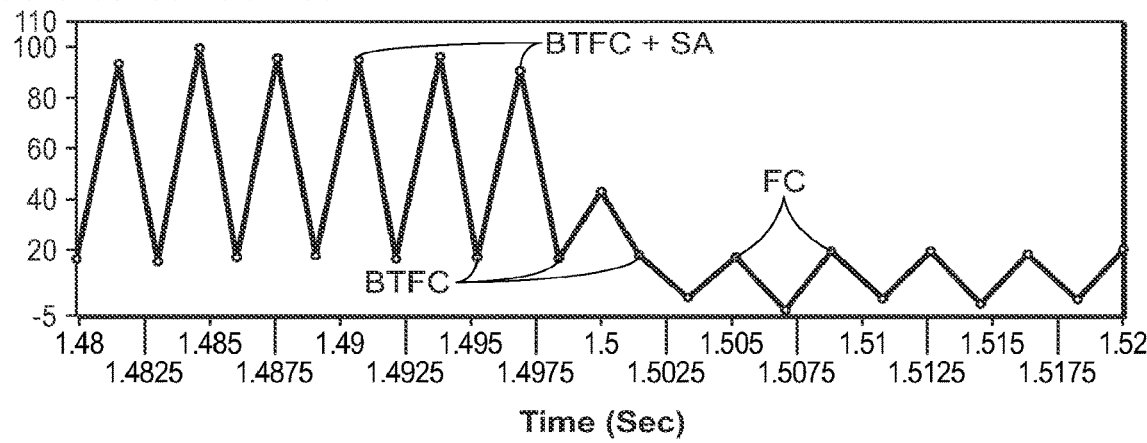
Figure 14:
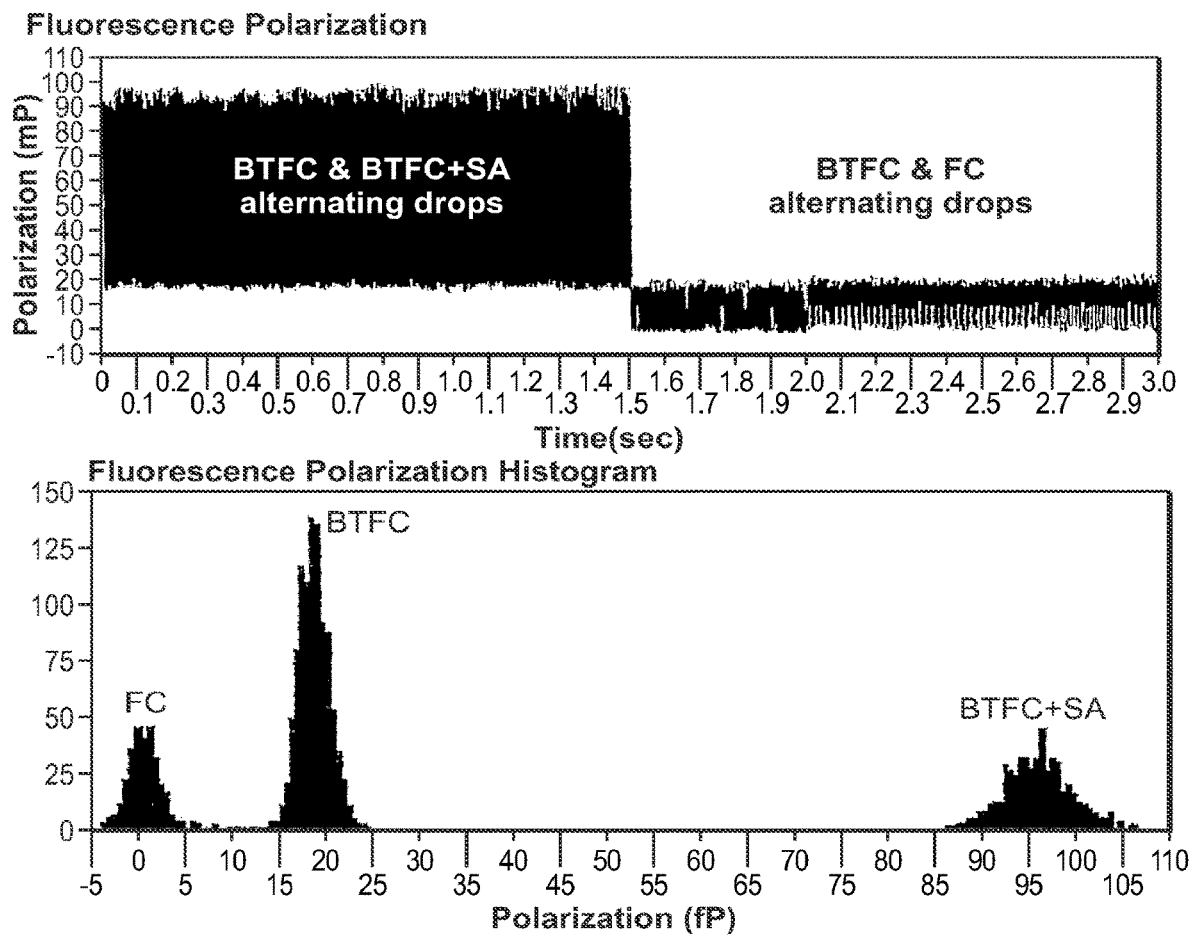
FIG. 14 is a graph showing a time trace and histogram of fluorescence polarization calculated from analyzed droplets.

During these experiments, the fluid flow rates were 200 ul/hr for FC, BTFC, and BTFC+SA, and 600 ul/hr for the oil (FC3283+10% "Avacado"). Droplets ranged in size from 65 to 75 um in diameter, depending on which water solution was used. Time between droplets varied from 1300 us to 2200 us, again depending on which fluid was used. Fluorescence polarization measurements were made by injecting BTFC in one nozzle, and BTFC+SA in the other. Once these measurements were completed, the BTFC+SA was replaced with FC and a second series of data was collected. FIG. 13 plots typical fluorescence data collected from both these runs, as well as the calculated Polarization for each of the droplets shown. FIG. 13 (top panel) shows raw polarized fluorescence signals collected on the test station when measuring BTFC and BTFC+SA, then BTFC and FC (the data is normalized so P(Fluorescein)=0.0). FIG. 13 (bottom panel) shows polarization calculated from each droplet in the top plot. The transition at t=1.5 sec is a mathematical artifact where the data collected for the two conditions were concatenated in software (the data after t=1.5 was collected approximately 30 minutes after the data collected before t=1.5). In this data, Vertical is fluorescence parallel to laser polarization, Horizontal is polarization perpendicular. In this data, the "horizontal" polarization has been normalized such that the Polarization is equal to zero for Fluorescein. The Polarization was calculated by integrating the fluorescence signal across the droplet for each polarization, then plugging the results into Equation 1. FIG. 14 plots the Polarization measured for a longer number of droplets, along with the histogram created from this data. FIG. 14 (top panel) shows polarization calculated from each droplet for a longer time period than in FIG. 3. FIG. 14 (bottom panel) shows histogram generated from the data in the top figure. The data after t=1.5 was collected approximately 30 minutes after the data collected before t=1.5.

As seen in the histograms of the Polarization, the polarization clusters tightly around three different mean values. The zero-centered mean ($\sigma$=1.7) corresponds to Fluorescein, while the 18.4 mP ($\sigma$=1.6) grouping corresponds to Biotinalated Fluorescein and the 96 mP ($\sigma$=3.46) grouping corresponds to Biotinalated Fluorescein bound to Steptaviden.

Example 9

Fluorosurfactants are synthesized by reacting Krytox 157 FSL, FSM, or FSH with aqueous ammonium hydroxide in a volatile fluorinated solvent. The solvent and residual water and ammonia are removed with a rotary evaporator. The surfactant can then be dissolved in a fluorinated oil (e.g., FC-3283 from 3M), which can then be used as the continuous phase of the emulsion. A typical concentration is 2.5 wt % of surfactant dissolved in the oil.

The channels of the microfluidic device are also coated with a fluorinated surface product. For example, the coating is applied from a 0.1-0.5 wt % solution of Cytop CTL-809M in CT-Solv 180. This solution is injected into the channels of a microfluidic device via a plastic syringe. The device is then heated to 90° C. for two hours, followed by 200° C. for an additional two hours. These surfactants in the fluorinated oil stabilize the aqueous droplets from spontaneously coalescing. By fluorinating the channel surfaces, the oil phase preferentially wets the channels and allows for the stable generation and movement of droplets through the device, the low surface tension of the channel walls minimizes the accumulation of channel clogging particulates.

Example 10

The quality of libraries of emulsified compounds can also be controlled so as to eliminate from the library those compounds that cross between droplets. By emulsifying a q-dot encoded, buffer-only droplet and allowing it to incubate with 1-1000 separately emulsified compounds quality control of libraries can be achieved. After incubation, the uniquely encoded q-dot droplet is sorted away from the compound-containing droplets and analyzed (e.g., by mass spec) for the presence of any of the compounds emulsified in the other 1-1000 types of droplets. Compounds that cross between droplets are identified and eliminated from the library.

Example 11

The present invention also enables the user to sort cells based on binding of an affinity-reagent attached to a means for signal amplification. As a non-limiting example, an antibody fused to an enzyme (e.g., alk/phos, β-gal, horseradish peroxidase, etc.) is added to a mix of cells and incubated. The antibody can be against a particular cell-surface marker, for example, such as a cancer marker. The cell suspension can be washed or unwashed (if the antibody is in low concentration, i.e., less than 1 antibody per droplet, and the antibody has good binding properties).

The cells that have antibodies attached to them are then emulsified into droplets and an appropriate enzyme-substrate is added. The presence of a fluorogenic substrate product is amplified from one to many copies by the enzyme turning-over the substrate. Multiple enzymes and multiple substrates can be used to allow analysis of multiple samples with multiple fluorophores at the same time or sequentially. The affinity-reagent can be a protein, nucleic acid, or other molecule to which an enzyme (or portion thereof that when brought together becomes active) can be attached either covalently or through a reasonably strong interaction.

Example 12

The device of the present invention can also be used to sequence individual exons from individual chromosomes or tumor cells. A schematic diagram for performing this method is provided in FIG. 19. Individual specific primer-pairs to different exons (e.g., epidermal growth factor receptor (EGFR) exon-specific primer pairs) along with a primer-bound bead (e.g., a Dynal strepavidin bead) are each emulsified and then pooled to create a library emulsion (in FIG. 19 a set of 96 exon primer pairs are shown for illustrative purposes). Separately, a chromosomal DNA solution is diluted in an aqueous buffer such that upon emulsification on a microfluidic device described herein, a 30-50 micron droplet contains, on average, slightly less than a half-genome's concentration of DNA. Droplets from the pooled emulsion library set of exon-specific primers are coalesced with droplets containing the diluted solution of chromosomal DNA on a microfluidic device as described herein, and used in a bead-based DNA amplification reaction (i.e., PCR). The microfluidic device as described herein collects $1 \times 10^9$ of these droplets in 24 hours, which results in an emulsion of droplets, some of which contain beads with amplified exon-DNA attached. After PCR, the emulsions are broken by centrifugation, the beads are isolated, washed, and then enriched for DNA-containing beads on a microfluidic device as described herein. The exon- and chromosome-specific DNA-containing beads are randomly placed into a picotiter plate (454 Corp.) and sequenced using a Life Sciences DNA sequencing instrument (as provided by 454 Corp. and described in any of U.S. application Ser. No. 09/814,338, filed Mar. 21, 2001; U.S. application Ser. No. 10/104,280, filed Mar. 21, 2002; U.S. application Ser. No. 10/767,899, filed Jan. 28, 2004; U.S. application Ser. No. 11/045,678, filed Jan. 28, 2005; or U.S. application Ser. No. 11/195,254, filed Aug. 1, 2005, each of which are incorporated herein by reference in their entirety). A summary of this process is provided by FIG. 20. The emulsion PCR amplification reaction can be performed off-chip using control chromosomal DNA as template and a single set of exon-specific primers, or on-chip (i.e., on the microfluidic devices of the present invention as described herein).

In a more specific example, the microfluidic devices and methods of the present invention have been used to develop individual exon-, and chromosome-specific sequencing methods with off-line emulsion PCR using chromosomal DNA as template and a single set of exon-specific primers.

The ability to combine (i.e., coalesce) two droplets together can be used to amplify an exon from an individual chromosome.

a. PCR Amplification of DNA within a Droplet.

454 Life Sciences has previously demonstrated emulsion solid-phase PCR in droplets of a size range anticipated for the microfluidic devices according to the present invention. Successful DNA amplification using an emulsion of a PCR with the perfluorocarbon oils and surfactants used to generate and manipulate droplets on microfluidic devices of the present invention have also been demonstrated. Several polymerases (notably those from archea, e.g., Thermal Ace DNA Pol; Pfu Turbo Pol; Advantage 2-CG Taq Pol; and Advantage Taq Pol) work well in the buffers and oils used in the devices described herein.

b. Setting Up the Exon-Specific PCR Reactions.

In the first set of experiments, robust bulk conditions for the droplet-based exon amplification are developed. Primers within an exon in the EGFR gene can be used. Approximately 10% of patients with non-small-cell lung cancer (NSCLC) show responsiveness to targeted tyrosine kinase inhibitor (TKI) chemotherapy regimens. Response in patients has been strongly associated with somatic heterozygous mutations in the ATP cleft of the EGFR gene.

Wild-type and mutant chromosomal DNAs containing an 18 base pair (bp) deletion in an EGFR exon encoding this ATP cleft are used. Initial experiments can be performed in a bulk (i.e., off-instrument) solution using the perfluorocarbon oils and surfactants as described herein. Once conditions have been established with limiting chromosomal DNA these amplification experiments in mono-dispersed droplets formulated on-instrument are repeated. These droplets are collected and the DNA contained within amplified. The emulsion containing the amplified droplets are broken, and the aqueous phase analyzed by gel electrophoresis.

c. Measurement of Solid Phase Amplification.

Once the exon PCR reactions are working in solution from droplets formed on the instrument, these experiments will be repeated with droplets containing both primers and beads. The beads are emulsified with the exon primer pairs. One of the primers is attached to the bead using standard oligonucleotide coupling chemistry. Both primers will also be in solution (those skilled in the art will appreciate that the goal of solid-phase amplification is to generate enough amplified product in solution such that some of it is driven to the oligonucleotide primer attached to the bead). A serial dilution of chromosomal DNA in several trials is then added to the primer-bead solution. Droplets are formulated at a concentration of less than one bead per droplet. The DNA/primer/bead solution is gently shaken to keep the beads in suspension as the droplets are being formed on the microfluidic devices of the present invention. The droplets are collected from the instrument and the DNA within them is amplified by PCR off-line.

d. Measurement of Single-Chromosome PCR.

On-bead hybridization of two separately-labeled cy3- and cy 5-containing oligonucleotide probes is used to measure amplified-DNA attachment efficiency. A cy3-labeled probe is synthesized complementary to the sequence within the 18 bp deletion region, and a second cy5-labeled oligonucleotide probe is synthesized that will span this deletion (with complementarity to both 5' and 3' sides). The probes are designed such that at 30° C. they do not cross-hybridize. The quantitation and ratio of cy3:cy5 dyes on the bead is a measure of the amount of each specific allele of the DNA present on the bead.

Figure 21:
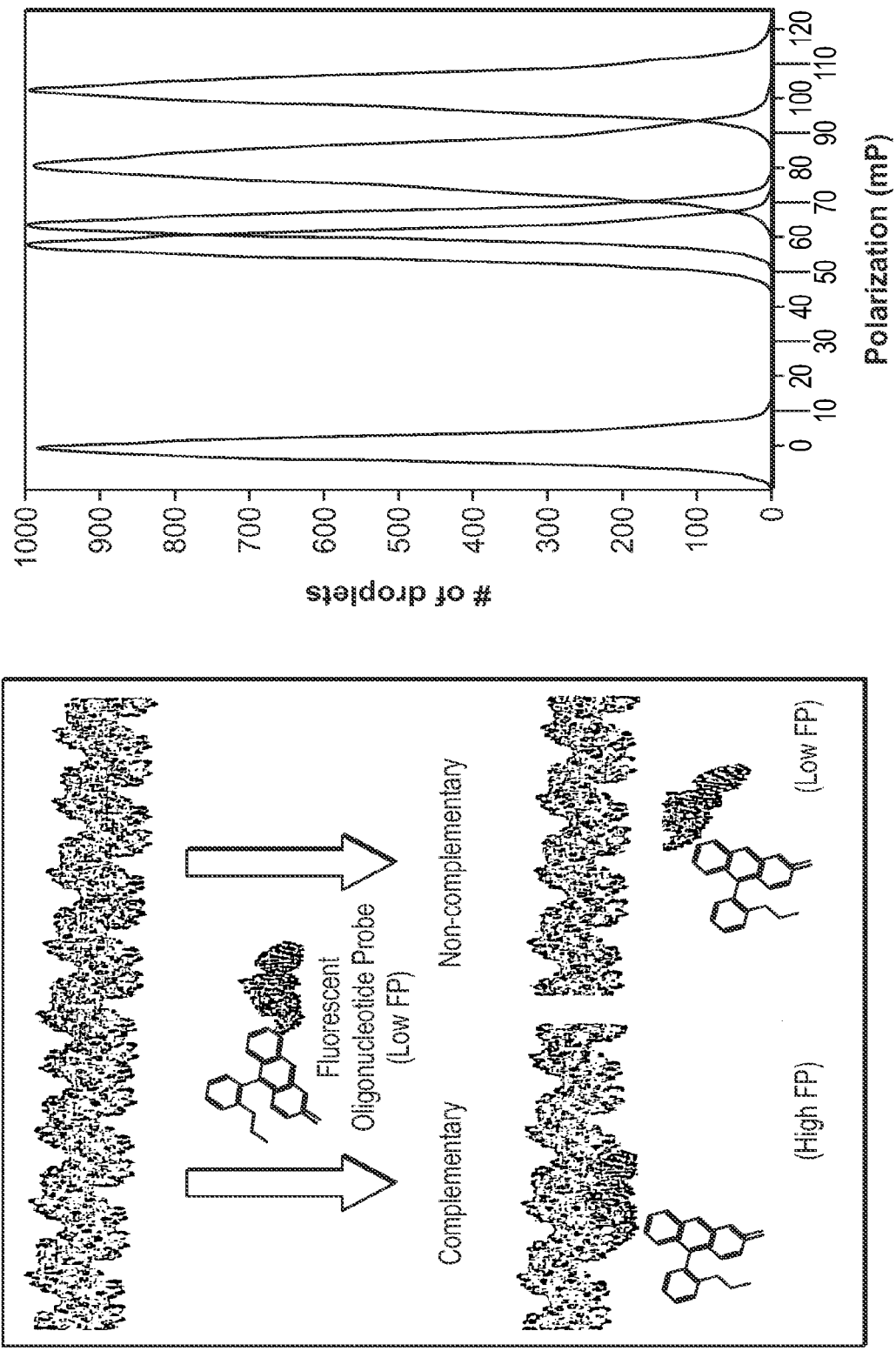
FIG. 21 shows measurement of DNA hybridization using fluorescence polarization (FP) on the microfluidic device described herein. (A) FP can be used to measure the binding of 2 DNA molecules on the microfluidic device. (B) Oligonucleotide 102 is complement to both 101 and 103. The addition of either oligonucleotide to the labeled 102 shifts the mP value, indicative of binding. Addition of 102 to non-complementing oligos does not change its mP (data not shown). Oligonucleotides; #101:5' Biotin-ATCCGCCCCA-GCA GCTGCCAGGCACAGCCCCTAAACTCCTGATT-TATGCTGCATCCATTTTGC 3'(SEQ ID NO: 1); #102: 5' Fluorescein-GCAAAATGGATGCAGCATAAATCAG-GAGTTTAG 3'(SEQ ID NO: 2); #103: 5' Fluorescein-CTAAACTCCTGATTTA TGCTGCATCCATTTTGC-3' (SEQ ID NO: 3).

As a control, a fluorescein-labeled oligonucleotide complementary to the oligonucleotide attached to the bead is used. This control oligonucleotide is used to estimate the maximum amount of cy3 or cy5-labeled probe that can attach to the bead. The hybridized beads are washed to remove un-hybridized probe and the amount of fluorescein still attached to individual beads is compared to fluorescein-standard concentrations. Other methods and controls for estimating attached DNA (such as fluorescence polarization) can be used in conjunction with the microfluidic devices according to the present invention. FIG. 21. The chromosomal DNAs are diluted and added to exon-primer containing droplets on the microfluidic devices of the present invention using conditions established in the bulk emulsions. After PCR amplification, the beads are isolated, washed, and hybridized in solution to the cy3-, cy5-labeled probes. The hybridized beads are washed to remove unhybridized and non-specifically-bound labeled nucleotide and the amount of dye still attached to individual beads is determined using a fluorescent microscope. The % synthesized is estimated from the maximum estimated to be able to be synthesized. The 454 instrument requires $1 \times 10^7$ copies of DNA per bead for accurate reads. Using the methods described herein, more than $1 \times 10^7$ DNA molecules per bead can be attached.

PCR is a typical temperature-controlled and enzyme catalyzed biochemical reaction that consists of the periodical repetition of three different temperatures (melting, annealing and extension temperature). Alternatively, two temperatures can be applied by combining the annealing and extension temperatures, thus further reducing the complexity of the thermal cycling profile and increasing the speed and efficiency of the PCR reaction. Because of the temperature-sensitivity of the PCR system a minor temperature difference may significantly affect the efficiency of DNA amplification, especially in emulsion PCR microfluidic systems.

Accordingly, the effects of temperature on enzyme kinetics, heating and temperature-measuring methods in emulsion PCR microfluidics are critical in order to gain a better understanding of PCR kinetics in microfluidics.

Several thermostable polymerases that work well in oils used in the microfluidic devices have been identified herein. A syringe pump attached to a microfluidic device of the present invention with appropriate sensors and heating elements (described below) can be used to model the ability of the polymerases to generate PCR product off-instrument.

The choice of a heating method for PCR microfluidics is of importance for achieving faster temperature ramping rates. In one embodiment, a contact-heating method (e.g., the use of hot air) can be used. Contact-heating methods utilize electrothermal conversion to heat the PCR solution, in which the thermal components embedding the heating element are in direct contact with the components of the PCR amplification. To date, along with the thin film heaters, metallic heating blocks and Peltier-effect-based thermoelectric ceramic heating blocks have been widely applied in temperature control of PCR.

In one embodiment, 2 Kaptan Thermofoil heaters from Minco and a two-step PCR cycling method can be used. Thermofoil heaters are thin, flexible heating elements consisting of an etched foil resistive element laminated between layers of flexible insulation. Thermofoil heaters are applied to the surface of the part to be heated. Their thin profile gives close thermal coupling between the heater and heat sink. The flat foil element of Thermofoil heaters transfers heat more efficiently and over a larger surface area than round wire. Thermofoil heaters, therefore, develop less thermal gradient between the resistive element and heat sink.

Methods of Temperature Measurement for PCR Microfluidics.

In emulsion PCR microfluidics, it is critical to select methods for temperature measurement to accurately control temperature during PCR cycling. Temperature measurement methods are usually divided into two categories: contact and non-contact temperature measurement. The former includes thin-film type temperature sensing and non-thin-film-type temperature sensing.

In one embodiment, temperature measurement can be performed by using the Minco Non-Invasive Sensors Design Kit. This kit comes with thermal-ribbon, thermal-tab, and bolt-on resistance temperature detectors that will allow us to accurately sense temperature without having to drill or tap into the chip. The detectors are accurate to +/−0.25° C. In another embodiment, temperature measurements using a temperature dependent fluorescent dye (e.g., a dilute fluorophore such as rhodamine B or rhodamine 3B) can constitute a second technique for measuring temperature in microfluidic structures.

The methods discussed above can be repeated with a second primer set, which consists of 96 different exons. Primers can be designed and tested on an MJ Research PCR instrument a priori to establish suitability to the two-step PCR conditions to be used on-chip.

All exons to be amplified are first sequenced by traditional Sanger methods to establish a base-line read. Where possible, exons with known polymorphisms within the to-be-sequenced DNA (i.e., the individual will be polymorphic at a site within the exon) are selected. We expect 50:50 for each polymorphism, this analysis will enable us to gather information about the bias in sequencing during the on-chip amplification reactions. The controls for attachment are the same as that described above.

A pool of primer sets are tested on a diluted genomic DNA solution whereby the genomic DNA is at several concentrations.

Once the ideal amount and quality of DNA attached to the beads is achieved, the 454 instrument will be used to sequence the beads. DNA-containing beads are enriched for on microfluidic devices according to the present invention either using a DNA staining agent (ex, Syber green) or by hybridization to a fluorescent oligonucleotide probe. Appropriate controls are used to estimate the number of exon copies per bead.

The invention claimed is:

1. A method for detecting a polymerase chain reaction (PCR) product in an aqueous droplet, the method comprising:
   providing a repertoire of barcoded compounds attached to beads in an aqueous fluid;
   emulsifying the aqueous fluid to generate a plurality of aqueous droplets, each aqueous droplet comprising one of the beads;
   conducting inside the plurality of aqueous droplets an amplification reaction involving one or more of the repertoire of barcoded compounds, wherein the conducting step results in barcoded amplicons that are released from the beads;
   breaking the plurality of aqueous droplets to pool the barcoded amplicons; and
   analyzing the barcoded amplicons.

2. The method of claim 1, wherein the aqueous droplets are surrounded by the immiscible carrier fluid.

3. The method of claim 2, wherein emulsifying comprises flowing the aqueous fluid through a channel into an immiscible carrier fluid that is injected from a direction substantially perpendicular to the channel.

4. The method of claim 2, wherein the immiscible carrier fluid is an oil.

5. The method of claim 1, wherein analyzing comprises sorting the barcoded amplicons based on a presence of a plurality of fluorescent reporter molecules.

6. The method of claim 1, wherein the at least one of the aqueous droplets further comprises a label.

7. The method of claim 6, wherein the label is an organic dye.

8. The method of claim 6, wherein the barcoded amplicons of the amplification reaction comprise the label.

9. The method of claim 1, wherein the amplicons are released from the beads by heating.

10. The method of claim 9, wherein heating occurs during the amplification reaction.

11. The method of claim 1, wherein the amplification reaction involves thermocycling.

12. The method of claim 1, wherein the repertoire of compounds comprise nucleic acids.

13. The method of claim 12, wherein the nucleic acids comprise genomic DNA, cDNA, or RNA.

14. The method of claim 1, wherein the amplicons comprise DNA or cDNA.

15. The method of claim 1, wherein each aqueous droplet comprises a primer pair.

16. The method of claim 15, wherein the primer pairs are different between each aqueous droplet.

17. The method of claim 1, wherein the aqueous fluid further comprises a polymerase and a plurality of deoxynucleotides.

18. The method of claim 6, wherein the label is a fluorescent label.

* * * * *